US012420099B2

(12) United States Patent
Gole et al.

(10) Patent No.: US 12,420,099 B2
(45) Date of Patent: Sep. 23, 2025

(54) SYSTEMS, APPARATUSES, AND METHODS FOR FACILITATING ELECTRODE PLACEMENT FOR SPINAL CORD STIMULATION

(71) Applicant: Cartis Neuro, Inc., Wilmington, DE (US)

(72) Inventors: Rahul Gole, Plainsboro, NJ (US); Sam Perlmutter, McMurray, PA (US); Karthik Seshan, Ossining, NY (US)

(73) Assignee: Cartis Neuro, Inc., Wilmington, DE (US)

( * ) Notice: Subject to any disclaimer, the term of this patent is extended or adjusted under 35 U.S.C. 154(b) by 0 days.

(21) Appl. No.: 18/921,893

(22) Filed: Oct. 21, 2024

(65) Prior Publication Data
US 2025/0128071 A1    Apr. 24, 2025

Related U.S. Application Data

(60) Provisional application No. 63/545,132, filed on Oct. 20, 2023.

(51) Int. Cl.
*A61N 1/372*    (2006.01)
*A61N 1/05*    (2006.01)
*A61N 1/36*    (2006.01)

(52) U.S. Cl.
CPC ....... *A61N 1/36139* (2013.01); *A61N 1/0553* (2013.01); *A61N 1/36157* (2013.01); *A61N 1/36171* (2013.01); *A61N 1/36175* (2013.01); *A61N 1/37247* (2013.01)

(58) Field of Classification Search
CPC .............. A61N 1/36139; A61N 1/0553; A61N 1/36157; A61N 1/36171; A61N 1/36175; A61N 1/37247
See application file for complete search history.

(56) References Cited

U.S. PATENT DOCUMENTS

| 7,305,268 | B2 | 12/2007 | Gliner et al. | |
|---|---|---|---|---|
| 9,855,423 | B2 | 1/2018 | Jiang et al. | |
| 11,123,555 | B2 | 9/2021 | Su et al. | |
| 2010/0274315 | A1* | 10/2010 | Alataris | A61N 1/06 |
| | | | | 607/46 |

(Continued)

FOREIGN PATENT DOCUMENTS

AU    2023263572 A1    1/2024

OTHER PUBLICATIONS

Carolin Otto et al; Targeting Transcutaneous Spinal Cord Stimulation Using a Supervised Machine Learning Approach Based on Mechanomyography; Sensors 2024, 24(2).

*Primary Examiner* — Eugene T Wu
(74) *Attorney, Agent, or Firm* — Caldwell Intellectual Property Law

(57) ABSTRACT

Systems, apparatuses, and methods described herein facilitate the placement of spinal cord stimulator (SCS) electrode in relationship to neural tissue of the spinal cord based on electromyography (EMG) data. The systems, apparatuses, and methods are designed to assist physicians and surgeons target specific neurophysiological locations through stimulation and subsequent visualization of EMG activity in response to stimulation to more precisely identify the location of the SCS electrodes that will maximize the intended therapeutics effects of SCS.

28 Claims, 21 Drawing Sheets

(56) References Cited

U.S. PATENT DOCUMENTS

| | | | |
|---|---|---|---|
| 2017/0281959 A1* | 10/2017 | Serrano Carmona | ........................ A61N 1/36071 |
| 2019/0134383 A1* | 5/2019 | Brill | ........................ A61B 5/407 |
| 2019/0275333 A1* | 9/2019 | O'Brien | ............. A61N 1/36062 |
| 2022/0330878 A1 | 10/2022 | Seshan et al. | |
| 2022/0331591 A1 | 10/2022 | Seshan et al. | |
| 2022/0331593 A1 | 10/2022 | Seshan et al. | |

* cited by examiner

SYSTEMS, APPARATUSES, AND METHODS FOR FACILITATING ELECTRODE PLACEMENT FOR SPINAL CORD STIMULATION

CROSS-REFERENCE TO RELATED APPLICATIONS

This application claims the benefit of priority of U.S. Provisional Application Ser. No. 63/545,132, filed on Oct. 20, 2023, and entitled "SYSTEMS, APPARATUSES, AND METHODS FOR FACILITATING ELECTRODE PLACEMENT FOR SPINAL CORD STIMULATION", the entirety of which is incorporated herein by reference.

FIELD OF THE INVENTION

The present disclosure generally relates to the field of medical devices. In particular, the present disclosure relates to systems, apparatuses, and methods for optimizing electrode placement for spinal cord stimulation (SCS) applications.

BACKGROUND

Spinal Cord Stimulation (SCS) involves electrically stimulating tissue near the spinal cord to modulate nerve signaling to the brain. SCS systems are mainly used for the management of chronic pain and may provide relief for chronic pain resulting from a variety of causes such as, without limitation injury, surgical complications, neuropathy, complex regional pain syndrome, and/or arachnoiditis, among others. SCS systems typically include implantable electrodes that are positioned near a location along the spinal cord associated with one or more afflicted regions of the body (e.g., one or more regions at which a patient is perceiving pain). The electrodes may be programmed to generate current pulses to block pain signals from reaching the brain, thereby reducing or eliminating perceived pain in the one or more afflicted regions of the body. Proper positioning of the implanted electrodes may directly impact patient outcomes, as placement failures may result in inadequate pain relief or compounded discomfort. In current positioning methods, practitioners may partially sedate a patient, implant the electrodes using a fluoroscope to monitor their location with respect to the spinal column, and then wake the patient to gather verbal feedback regarding the quality of the placement. Electrodes are often temporarily placed for a trial period, during which patients may provide feedback about the efficacy of the therapeutic stimulation before undergoing permanent placement. Such feedback may often be qualitative and/or subjective. Therefore, current positioning methods may result in sub-optimal placement of the electrodes and potential complications due to a lack of accurate information or assessment pertaining to the location of the electrodes relative to the neural tissue of the spine. There are no existing apparatus and methods that provide a practitioner with sufficiently quantitative information to facilitate efficient and effective placement of electrodes of an SCS system.

SUMMARY OF THE DISCLOSURE

In an aspect, an apparatus for facilitating electrode placement is described. The apparatus includes a stimulation device. The stimulation device includes an electrode lead having a plurality of electrodes, wherein each electrode of the plurality of electrodes is configured to transmit an electrical impulse towards a target location. The apparatus further includes a plurality of sensors, wherein each sensor of the plurality of sensors is configured to detect electrical activity data. The apparatus further includes a computing device communicatively connected to the stimulation device and the plurality of sensors. The computing device includes a processor; and a memory communicatively connected to the processor, wherein the memory contains instructions configurating the processor to implement a first stimulation protocol. The first stimulation protocol includes one or more stimulation parameters pertaining to at least an electrode of the plurality of electrodes. The processor is further configured to receive the electrical activity data from at least a sensor of the plurality of sensors in response to the stimulation protocol. The processor is further configured to analyze the electrical activity data as a function of one or more predefined criteria. The processor is further configured to generate, using a user interface, a visual representation as a function of the analyzed electrical activity data.

In another aspect, a method for facilitating electrode placement is described. The method includes implementing, by a processor, a first stimulation protocol, wherein the first stimulation protocol includes one or more stimulation parameters pertaining to at least an electrode of a plurality of electrodes, wherein each electrode of the plurality of electrodes is configured to transmit an electrical impulse towards a target location. The method further includes receiving, by the processor, electrical activity data from at least a sensor of the plurality of sensors in response to the stimulation protocol. The method further includes analyzing, by the processor, the electrical activity data as a function of one or more predefined criteria. The method further includes generating, by the processor using a user interface, a visual representation as a function of the analyzed electrical activity data.

In another aspect, another method for facilitating electrode placement is described. The method includes placing one or more sensors at a target location, wherein the one or more sensors are configured to detect electrical activity data. The method further includes implementing, using a processor, and a stimulation protocol using one or more electrodes positioned at a target spinal cord site. The method further includes receiving, by the processor, electrical activity data from the one or more sensors. The method further includes generating, by the processor, a visualization as a function of the electrical activity data. The method further includes adjusting, by the processor, a functional positioning of the one or more electrodes as a function of the electrical activity. The method further includes setting up a neurostimulation therapy as a function of the adjusted functional positioning.

These and other aspects and features of nonlimiting embodiments of the present invention will become apparent to those skilled in the art upon review of the following description of specific nonlimiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1A:
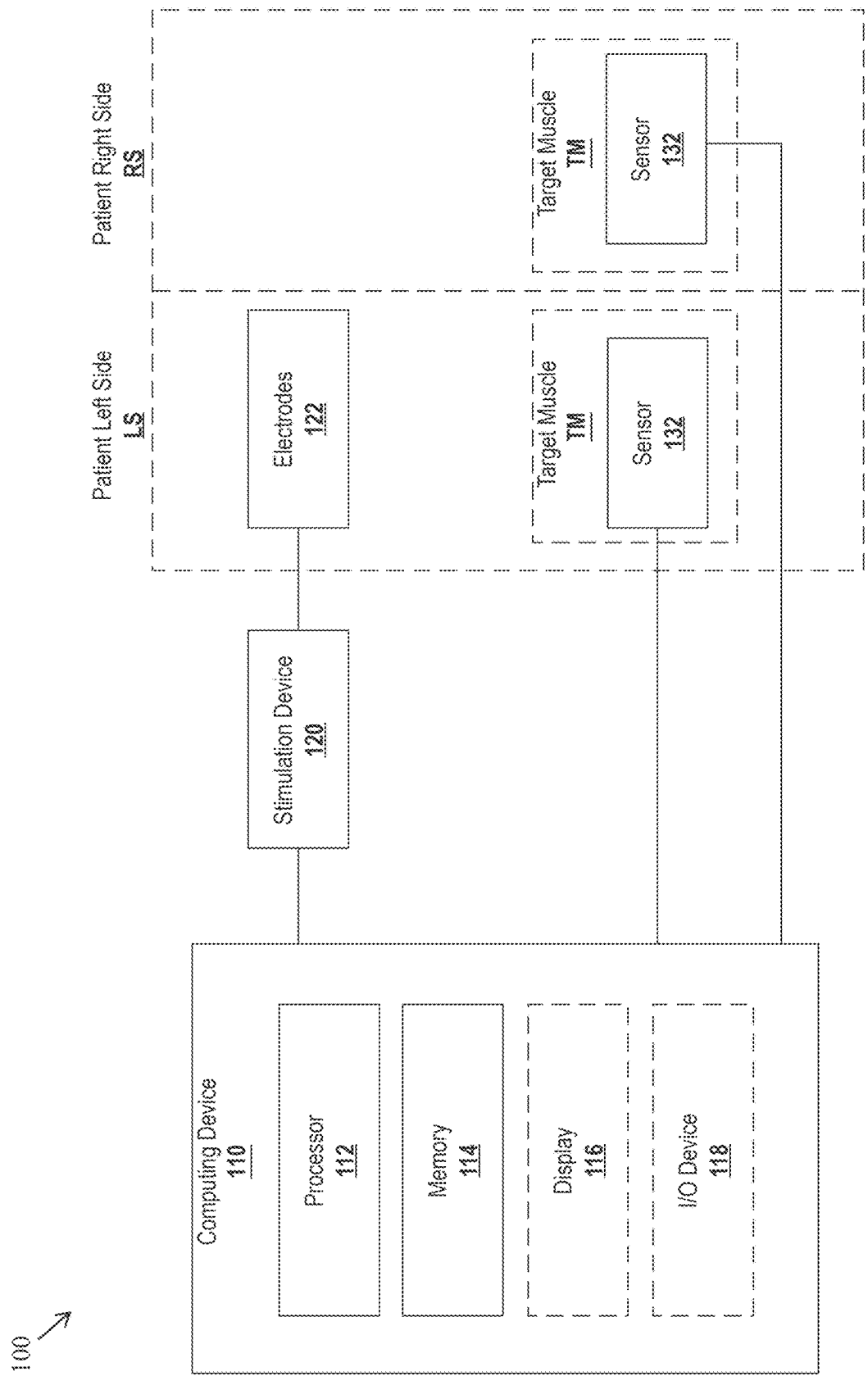
FIG. 1A is a schematic block diagram illustrating an exemplary embodiment of an apparatus for facilitating a placement of electrodes using electromyography (EMG) data.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Systems, apparatuses, and methods described herein relate to optimizing electrode placement for spinal cord stimulation applications. In particular, the systems, apparatuses, and methods described herein provide a practitioner with feedback related to electrode placement to aid the practitioner in positioning the electrodes in an effective location for subsequent spinal cord stimulation therapy.

Current methods for placing spinal cord stimulation devices often rely on qualitative feedback from a patient gathered during an implantation surgery and/or fluoroscopy data to indicate the location of these devices with respect to the vertebral column of the patient. However, determining electrode placement based on subjective feedback from a patient while the patient is undergoing a procedure may not provide an accurate representation of sensations the patient may perceive after the procedure. Additionally, a practitioner may only use fluoroscopy data as an approximate guide to position electrodes based on their relative location with respect to bone rather than to neural tissue, the actual targets of stimulation.

All individuals have a vertebral midline (ML) and a functional midline (FML). For the purposes of this disclosure, a "vertebral midline (ML)" is the central line running vertically along a spine, formed by an alignment of the vertebrae in a vertebral column. An ML may act as a key anatomical reference point for spinal alignment and symmetry in medical, surgical, and diagnostic contexts, among others. An ML may help guide procedures involving a spine and may be important in evaluating conditions including without limitation scoliosis or spinal deformities, where a deviation from the ML may indicate a misalignment or abnormal curvature of the spine. For the purposes of this disclosure, a "functional midline (FML)" is a location along the nerve tissue of a spinal cord where activation of the nerve tissue results in equal or substantially equal bilateral activation of myotomes on both the left side (LS) and the right side (RS) of the body. The concept of FML may often be used in physical therapy and spinal assessments. An FML may be considered an ideal central alignment or axis through a vertebral column that allows for optimal movement, balance, and/or load distribution in the body. An FML may refer to locations along the nerve tissue of a spinal cord that represent a midline based on functionality of nerve tissue rather than the structure of spine. In other words, an FML may represent a theoretical line along which forces are distributed evenly during movement, which ensures that a spine functions properly without excessive strain on any particular region. A deviation from FML may lead to postural imbalances, muscle strain, and/or spinal issues including without limitation scoliosis and/or kyphosis, among others. In some cases, an FML may also coincide with the posterior median sulcus of a spinal cord. The ML and FML of the same individual may or may not be aligned, as described in further detail in this disclosure.

An ML and a FML may not have the same coordinates, as the ML may not directly correspond to the location that results in equal activation of the left-side and right-side myotomes or muscles. In some cases, the ML and FML of the spine may not align. This misalignment may be due to one or more reasons such as, without limitation, a torsion of the spinal cord, a misaligned location of the spinal cord relative to the spinal canal within a vertebral column, an uneven distribution of nerve tissue, a presence of scar tissue, an uneven synaptic strength, and/or an uneven muscle composition, among others. In such cases, positioning electrodes relative to the bone of a spine (i.e., the vertebrae) may not yield the most efficacious therapeutic results.

For the purposes of this disclosure, a "myotome" is a group of muscles that are innervated by the motor fibers of a specific spinal nerve root. Each myotome corresponds to a particular segment of the spinal cord and is responsible for controlling movements in specific muscle groups. Myotomes are crucial for diagnosing nerve injuries or diseases affecting motor function. Understanding the distribution and function of myotomes may help clinicians pinpoint spinal cord or nerve damage based on muscle weakness or paralysis patterns.

For the purposes of this disclosure, a "practitioner" is a medical professional trained in electrode implantation. A practitioner may refer to a surgeon, a physician/pain physician, a clinician, a technician, or any other personnel authorized to perform electrode implantation and/or interact with the invention described herein.

The embodiments described herein address the challenges of existing methods by providing at least the following benefits: (1) provide near real-time feedback to a practitioner without waking a patient during implantation; (2) provide quantitative information relating to electrode placement; (3) compatible with a variety of stimulation and recording electrodes; (3) increase the accuracy of electrode placement; (4) reduce electrode placement errors and associated complications; (5) potentially reduce the need to program high current amplitude for therapy stimulation due to proper positioning of electrodes; and (6) enable quantitative tracking of electrode migration over time.

In one or more embodiments, the system/apparatus described herein may be capable of facilitating a placement of electrodes in relation to the neural tissue of a spinal cord. Such capability may be achieved based on electromyography (EMG) data. For the purposes of this disclosure, electromyography (EMG) is a clinical and diagnostic technique used to evaluate the electrical activity produced by skeletal muscles and the motor neurons that control them. An EMG procedure often involves insertion of fine-needle electrodes into muscle tissue and/or placement of surface electrodes on the skin. EMG records the electrical signals generated during muscle contraction and rest, aiding in diagnosing neuromuscular disorders, nerve dysfunctions, and conditions such as, without limitation, neuropathy, myopathy, carpal tunnel syndrome, or motor neuron diseases (e.g., amyotrophic lateral sclerosis and/or the like), among others. EMG may be essential for analyzing nerve-to-muscle signal transmission and muscle response integrity, which may help clinicians determine underlying neuromuscular issues.

In one or more embodiments, the system/apparatus described herein may be used to provide clinical decision support for a neurostimulation therapy. For the purposes of this disclosure, a neurostimulation therapy is a medical treatment that involves delivering electrical stimulation to specific nerves, spinal cord regions, and/or brain areas to modulate neurological activity. A neurostimulation therapy may work by applying a controlled electrical pulse through an implanted or external device, which stimulates nerve pathways to alleviate symptoms associated with chronic pain, neurological disorders, and/or other medical conditions. Such stimulation may alter pain signals, restore motor functions, and/or regulate abnormal neurological activity, among others, offering therapeutic effects for conditions such as, without limitation, chronic pain, epilepsy, and/or Parkinson's disease, among others.

In one or more embodiments, the system/apparatus described herein may be designed to assist practitioners in targeting specific neurophysiological locations through spinal cord stimulation (SCS) and visualization of EMG activity. This design may help precisely identify the location that will maximize intended therapeutic effects of SCS and aid in a placement of electrodes over such location.

In one or more embodiments, the system/apparatus described herein may be configured as an open-loop system in which the system/apparatus may process and/or analyze EMG responses and output a visual representation of the analyzed EMG data to a practitioner in a real-time or substantially real-time manner.

In one or more embodiments, a practitioner may glean information relating to the location of the FML of a spine based on the outputs and/or visual representation of the analyzed EMG data. In one or more embodiments, the system/apparatus described herein may be configured as a closed-loop system in which adjustments are made to stimulation parameters as a result of EMG activation analysis and processing.

Suitable examples of systems, apparatus, and devices for placement of electrodes may be consistent with details disclosed in U.S. Patent Application Publication No. 2022/0331593, filed on Apr. 18, 2022, U.S. Patent Application Publication No. 2022/0330878, filed on Apr. 18, 2022, and U.S. Patent Application Publication No. 2022/0331591, filed on Apr. 18, 2022, the entirety of each of which is incorporated herein by reference.

For purposes of description herein, relating terms, including "top", "bottom", "left", "right", "front", "back", "vertical", "horizontal", and derivatives thereof are defined from the perspective of a hypothetical person using or interacting with the invention described herein.

Referring now to FIG. 1A, FIG. 1A is a schematic block diagram illustrating an exemplary embodiment of an apparatus 100 for facilitating electrode placement. Apparatus 100 includes a computing device 110. Computing device 110 may include any analog or digital control circuit, including without limitation an operational amplifier circuit, a combinational logic circuit, a sequential logic circuit, an application-specific integrated circuit (ASIC), a field programmable gate arrays (FPGA), or the like. Computing device 110 may include any computing device as described in this disclosure, including without limitation a microcontroller, microprocessor, digital signal processor, and/or system on a chip, as described elsewhere in this disclosure. Computing device 110 may include, be included in, and/or communicate with a mobile device such as without limitation a mobile telephone, smartphone, or tablet. Computing device 110 may include a single computing device operating independently, or may include two or more computing devices operating in concert, in parallel, sequentially, or the like; two or more computing devices may be included together in a single computing device or in two or more computing devices. Computing device 110 may interface or communicate with one or more additional devices, as described below in further detail, via a network interface device. A network interface device may be utilized for connecting computing device 110 to one or more of a variety of networks and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from computing device 110. Computing device 110 may include without limitation a first computing device or cluster of computing devices in a first location and a second computing device or cluster of computing devices in a second location. Computing device 110 may include one or more computing devices dedicated to data storage, security, distribution of traffic for load balancing, and the like. Computing device 110 may distribute one or more computing tasks as described below across a plurality of computing devices of computing device, which may operate in parallel, in series, redundantly, or in any other manner used for distribution of tasks or memory between computing devices. Computing device 110 may be implemented, as a nonlimiting example, using a "shared nothing" architecture.

With continued reference to FIG. 1A, computing device 110 may be designed and/or configured to perform any method, method step, or sequence of method steps in any embodiment described in this disclosure, in any order and with any degree of repetition. For instance, computing device 110 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 110 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. A person of ordinary skill in the art, upon reviewing the entirety of this disclosure, will be aware of various ways in which steps, sequences of steps, processing tasks, and/or data may be subdivided, shared, or otherwise dealt with using iteration, recursion, and/or parallel processing. More details regarding computing devices will be described below.

With continued reference to FIG. 1A, apparatus 100 and/or computing device 110 includes a processor 112. Processor 112 may include any suitable processing device(s) configured to run and/or execute a set of instructions or code. As nonlimiting examples, processor 112 may be and/or may include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data and/or power transfer), and/or the like. As further nonlimiting examples, processor 112 may include a general-purpose processor, a central processing unit (CPU), a microprocessor, a microcontroller, a Field Programmable Gate Array (FPGA), an Application Specific Integrated Circuit (ASIC), a processor board, a virtual processor, and/or the like. Processor 112 may be configured to run and/or execute or implement software application processes and/or other modules, processes, and/or functions, as described in further detail below.

With continued reference to FIG. 1A, apparatus 100 and/or computing device 110 includes a memory 114 communicatively connected to processor 112, wherein the memory 114 contains instructions configuring the processor 112 to perform any processing steps described herein. For the purposes of this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example, and without limitation, through wired or wireless electronic, digital, or analog, communication, either directly or by way of one or more intervening devices or components. Further, a communicative connection may include electrically coupling or connecting at least an output of one device, component, or circuit to at least an input of another device, component, or circuit, for example, and without limitation, using a bus or other facility for intercommunication between elements of a computing device. A communicative connection may also include indirect connections via, for example, and without limitation, wireless connection, radio communication, low-power wide-area network, optical communication, magnetic, capacitive, or optical coupling, and the like. In some instances, the terminology "communicatively coupled" or "operatively connected" may be used in place of communicatively connected in this disclosure.

With continued reference to FIG. 1A, memory 114 may include any suitable memory device(s) configured to store data, information, computer code or instructions (such as those described herein), and/or the like. In one or more embodiments, memory 114 may include one or more of a random access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and/or the like. In one or more embodiments, memory 114 may store instructions configuring processor 112 to execute one or more modules, processes, and/or functions associated with apparatus 100. As nonlimiting examples, memory 114 may configure processor 112 to control a stimulation device and/or process data received from one or more sensors. In one or more embodiments, memory 114 may store a suite of stimulation protocols including instructions describing a sequence by which a stimulation device will move through stimulation parameters. Additionally, and/or alternatively, in one or more embodiments, memory 114 may be configured to at least temporarily store EMG data, parameter data, patient notes, data visualizations, graphics, etc. In some cases, memory 114 may store such information locally. In some other cases, processor 112 may send such information to a remote server. In one or more embodiments, computing device 110 may be communicatively coupled to a remote server configured to securely store relevant data, such as data related to electrode implantation. In one or more embodiments, computing device 110 may retrieve relevant information from a remote server when needed. Additional details will be provided below in this disclosure.

With continued reference to FIG. 1A, apparatus 100 and/or computing device 110 may include or be communicatively connected to a data repository. For the purposes of this disclosure, a "data repository" is a centralized storage location where large volumes of data are collected, managed, and/or maintained for future retrieval, analysis, or distribution. A data repository may be a physical or virtual location used to store structured, semi-structured, or unstructured data. Data repositories are commonly used in scientific research, healthcare, business, and IT for securely storing data from various sources, making it easily accessible for analysis, reporting, or sharing. Nonlimiting examples of data repositories may include databases, data warehouses, and/or cloud storage solutions, among others. For the purposes of this disclosure, a "database" is an organized collection of data or a type of data store based on the use of a database management system (DBMS), the software that interacts with end users, applications, and the database itself to capture and analyze the data. A database may be implemented, without limitation, as a relational database, a key-value retrieval database such as a NoSQL database, or any other format or structure for use as database that a person of ordinary skill in the art would recognize as suitable upon review of the entirety of this disclosure. A database may alternatively, or additionally, be implemented using a distributed data storage protocol and/or data structure, such as a distributed hash table or the like. A database May include a plurality of data entries and/or records as described in this disclosure. Data entries in a database may be flagged with or linked to one or more additional elements of information, which may be reflected in data entry cells and/or in linked tables such as tables related by one or more indices in the database or another relational database. A person of ordinary skill in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1A, in some cases, processor 112 may be configured to query a database by searching within the database for a match. As a nonlimiting example, when a database includes a SQL database, processor 112 may be configured to submit one or more SQL queries to interact with the database. To retrieve data, a "SELECT" statement may be used to specify one or more columns, rows, table names, and/or the like, and optional conditions may be applied using WHERE clauses. In some cases, a DBMS may use indexes, if available, to quickly locate relevant rows and columns, ensuring accurate and efficient data retrieval. Once SQL queries are executed using a DBMS interface or code, results may be returned for further steps.

With continued reference to FIG. 1A, apparatus 100 and/or computing device 110 may include and/or be communicatively connected to a server, such as, without limitation, a remote server, a cloud server, a network server, and/or the like. In one or more embodiments, computing device 110 may be configured to transmit one or more processes to be executed by a server. In one or more embodiments, a server may contain additional and/or increased processor power wherein one or more processes as described below may be performed by server. As a nonlimiting example, one or more processes associated with data processing may be performed by a network server, wherein data are transmitted to the network server, processed, and transmitted back to computing device. In one or more embodiments, a server may be configured to perform one or more processes as described below to allow for increased computational power and/or decreased power usage by computing device 110. In one or more embodiments, computing device 110 may transmit processes to a server to conserve power or energy.

With continued reference to FIG. 1A, in one or more embodiments, apparatus 100 and/or computing device 110 may include or be communicatively connected to a central server, as described above. As a nonlimiting example, a central server may be implemented via node.js and/or connected to a cloud network server or cloud network system, including, without limitation, Amazon Web Services, wherein the cloud network server or cloud network system is configured to manage and analyze data using at least an application programming interface (API), as described below. In one or more embodiments, a central server may be communicatively connected to a third-party cloud network system, such as the Things Network, wherein data are handled and preprocessed before reaching at least an application programming interface.

With continued reference to FIG. 1A, in one or more embodiments, apparatus 100 and/or computing device 110 may include or be communicatively connected to one or more application programming interfaces. For the purposes of this disclosure, an "application programming interface" is a way for two or more computer programs or components to communicate with each other. It is a type of software interface that offers one or more services to other pieces of software. An application programming interface may be written in programming languages such as C++, Java, Pascal, JavaScript, CFML, PHP, Ruby, Python, or the like. A document or standard that describes how to build or use such a connection or interface is called an application programming interface specification. A computer system that meets this standard is said to implement or expose an application programming interface. The term application programming interface may refer either to the specification or to the implementation. Whereas a system's user interface, as described below, dictates how its end users interact with the system in question, its application programming interface dictates how to write code that takes advantage of that system's capabilities. In contrast to a user interface, which connects a computer to an end user, an application programming interface connects computers or pieces of software to each other. It is not intended to be used directly by an end user other than a programmer who is incorporating it into the software. An application programming interface is often made up of different parts which act as tools or services that are available to a programmer. A program or programmer that uses one of these parts is said to call that portion of the application programming interface. Calls that make up the application programming interface are also known as subroutines, methods, requests, or endpoints. An application programming interface specification defines these calls and explains how to use or implement them. One purpose of application programming interfaces is to hide the internal details of how a system works, exposing only those parts that a programmer will find useful, and keeping them consistent even if the internal details change later. Application programming interface may be custom-built for a particular pair of systems, or it may be a shared standard allowing interoperability among many systems. A person of ordinary skill in the art will recognize how to implement one or more application programming interfaces for and/or computing device 110 upon reviewing the entirety of this disclosure.

With continued reference to FIG. 1A, in one or more embodiments, apparatus 100 may include or be communicatively connected to a display 116. In some cases, display 116 may be configured to provide an interface for presenting information to a practitioner. In some cases, display 116 may be configured to present one or more visual representations of physiological data and biosignals (e.g., electromyogram data, electroencephalogram data, electrocardiogram data, temperature, blood pressure, respiratory rate, oxygen saturation, and/or the like) of a patient. In some cases, display 116 may be controlled by processor 112 of computing device 110. In some cases, display 116 may include a built-in display of computing device 110. In some other cases, display 116 may include a separate display device that is communicatively linked or operatively coupled to computing device 110. In some cases, display 116 may be controlled by processor 112 to display real-time or near real-time feedback related to positioning of electrodes, as described in further detail below. In some cases, display 116 may display a visual representation of the magnitude and/or level of symmetry of muscle activation measured by one or more sensors; accordingly, such visual representation may inform a practitioner regarding the direction in which the one or more sensors should be moved. As a nonlimiting example, processor 112 of computing device 110 may receive signals indicative of muscle activity measured from one or more sensors and determine a magnitude of activation for muscles corresponding to each sensor. Accordingly, processor 112 may then display a graphical interpretation using display 116 to show a practitioner whether any adjustment to one or more electrodes may be needed. In one or more embodiments, processor 112 may process data and then display using display 116 the processed data. Such processed data may be overlaid, upon display, with data collected from other diagnostic imaging modalities, such as, without limitation, MRI and/or fluoroscopy, among others.

With continued reference to FIG. 1A, for the purposes of this disclosure, a "display" or "display device" is a device configured to show visual information. In some cases, display 116 may include a liquid crystal display (LCD), a cathode ray tube (CRT), a plasma display, a light emitting diode (LED) display, and any combinations thereof. Display 116 may include, but is not limited to, a smartphone, tablet, laptop, monitor, tablet, and the like. Display 116 may include a separate device that includes a transparent screen configured to display computer-generated images and/or information. In one or more embodiments, display 116 may be configured to visually present data through a user interface or a graphical user interface (GUI) to at least a user, wherein the user may interact with the data through the user interface or GUI, as described in further detail below. In one or more embodiments, a user may view GUI through display 116. In one or more embodiments, display 116 may be located on a remote device, as described in further detail below.

With continued reference to FIG. 1A, display 116 may include a remote device. For the purposes of this disclosure, a "remote device" is a computer device separate and distinct from apparatus 100. For example, and without limitation, a remote device may include a smartphone, a tablet, a laptop, a desktop computer, or the like. In one or more embodiments, a remote device may be communicatively connected to apparatus 100 such as, for example, through network communication, through Bluetooth communication, and/or the like. In one or more embodiments, processor 112 may receive data from a user or practitioner and/or initiate one or more subsequent steps through a remote device. In one or more embodiments, one or more inputs from one or more users may be submitted through a user interface, such as a GUI, that is displayed using a remote device, as described below.

With continued reference to FIG. 1A, in one or more embodiments, apparatus 100 and/or computing device 110 may further include a user interface. For the purposes of this disclosure, a "user interface" is a means by which a user and a computer system interact, for example, using input devices and software. A user interface may include a graphical user interface (GUI), command line interface (CLI), menu-driven user interface, touch user interface, voice user interface (VUI), form-based user interface, any combination thereof, or the like. In one or more embodiments, a user may interact with a user interface using computing device distinct from and communicatively connected to apparatus 100, computing device 110, and/or processor 112, such as a smartphone, tablet, or the like operated by the user. A user interface may include one or more graphical locator and/or cursor facilities allowing user to interact with graphical models and/or combinations thereof, for instance using a touchscreen, touchpad, mouse, keyboard, and/or other manual data entry device. For the purposes of this disclosure, a "graphical user interface (GUI)" is a type of user interface that allows end users to interact with electronic devices through visual representations. In one or more embodiments, a GUI may include icons, menus, other visual indicators or representations (graphics), audio indicators such as primary notation, display information, and related user controls. A menu may contain a list of choices and may allow users to select one from them. A menu bar may be displayed horizontally across the screen as a pull-down menu. A menu may include a context menu that appears only when a user performs a specific action. Files, programs, web pages, and the like may be represented using a small picture within a GUI. In one or more embodiments, a GUI may include a graphical visualization of a user profile and/or the like. In one or more embodiments, processor 112 may be configured to modify and/or update a GUI as a function of at least an input or the like by populating a user interface data structure and visually presenting data through modification of the GUI.

With continued reference to FIG. 1A, in one or more embodiments, a GUI may contain one or more interactive elements. For the purposes of this disclosure, an "interactive element" is an element within a GUI that allows for communication with processor 112 by one or more users. For example, and without limitation, interactive elements may include a plurality of tabs wherein selection of a particular tab, such as for example, by using a fingertip, may indicate to apparatus 100 to perform a particular function and display the result through a GUI. In one or more embodiments, an interactive element may include tabs within a GUI, wherein the selection of a particular tab may result in a particular function. In one or more embodiments, interactive elements may include words, phrases, illustrations, and/or the like, to indicate a particular process that one or more users would like a system to perform. A person of ordinary skill in the art, upon reviewing the entirety of this disclosure, will be aware of various ways in which user interfaces, GUIs, and/or elements thereof may be implemented and/or used as described in this disclosure.

With continued reference to FIG. 1A, in one or more embodiments, apparatus 100, computing device 110, display 116, and/or a remote device communicatively connected thereto may be configured to display at least an event handler graphic corresponding to at least an event handler. For the purposes of this disclosure, an "event handler graphic" is a graphical element with which user interacts using a device to enter data. An event handler graphic may include, without limitation, a button, a link, a checkbox, a text entry box and/or window, a drop-down list, a slider, or any other event handler graphic deemed suitable by a person of ordinary skill in the art upon reviewing the entirety of this disclosure. For the purposes of this disclosure, an "event handler" is a module, data structure, function, and/or routine that performs an action on a device in response to one or more user inputs. For instance, and without limitation, an event handler may record data corresponding to user selections of previously populated fields such as drop-down lists, text auto-complete, and/or default entries, data corresponding to user selections of checkboxes, radio buttons, or the like, potentially along with automatically entered data triggered by such selections, user entry of textual data using a keyboard, touchscreen, speech-to-text program, and/or the like. An event handler may generate prompts for further information, may compare data to validation rules such as requirements that the data in question be entered within certain numerical ranges, and/or may modify data and/or generate warnings to a user in response to such requirements. An event handler may convert data into expected and/or desired formats, for instance such as date formats, currency entry formats, name formats, or the like. An event handler may transmit data from a remote device to apparatus 100, computing device 110, processor 112, and/or display 116.

With continued reference to FIG. 1A, in one or more embodiments, an event handler may include a cross-session state variable. For the purposes of this disclosure, a "cross-session state variable" is a variable recording data entered on remote device during a previous session. Such data may include, for instance, previously entered text, previous selections of one or more elements as described above, or the like. For instance, cross-session state variable data may represent a search that user entered in a past session. Cross-session state variable may be saved using any suitable combination of client-side data storage on a remote device and server-side data storage on a computing device; for instance, data may be saved wholly or in part as a "cookie" which may include data or an identification of remote device to prompt provision of cross-session state variable by the computing device, which may store the data on the computing device. Alternatively, or additionally, computing device 110 may use login credentials, device identifier, and/or device fingerprint data to retrieve cross-session state variable, which the computing device 110 may transmit to a remote device. Cross-session state variable may include at least a prior session datum. A prior session datum may include any element of data that may be stored in cross-session state variable. An event handler graphic may be further configured to display at least a prior session datum, for instance, and without limitation, by auto-populating user query data from previous sessions.

With continued reference to FIG. 1A, in one or more embodiments, apparatus 100, computing device 110, and/or processor 112 may configure display 116 and/or remote device to generate a graphical view. For the purposes of this disclosure, a "graphical view" is a data structure that results in display of one or more graphical elements on a screen. A graphical view may include at least a display element. For the purposes of this disclosure, a "display element" is an image that a program and/or data structure cause to be displayed. Display elements may include, without limitation, windows, pop-up boxes, web browser pages, display layers, and/or any other display element deemed relevant by a person of ordinary skill in the art upon reviewing the entirety of this disclosure. A graphical view may include at least a selectable event graphic corresponding to one or more selectable event handlers. For the purposes of this disclosure, a "selectable event graphic" is a graphical element that, upon selection, will trigger an action to be performed. Selection may be performed using a cursor or other locator as manipulated using a locator device such as a mouse, touchscreen, track pad, joystick, or the like. As a nonlimiting example, a selectable event graphic may include a redirection link. For the purposes of this disclosure, a redirection link is a hyperlink, button, image, portion of an image, and/or other graphic containing or referring to a uniform resource locator (URL) and/or other resource locator to another graphical view including without limitation buttons, and/or to a process that performs navigation to such URL and/or other resource locator upon selection of a selectable event graphic. Redirection may be performed using any event handler, including without limitation event handlers detecting the click of a mouse or other locator, access of redirection link using a touchscreen, the selection of any key, mouseover events, and/or the like.

With continued reference to FIG. 1A, in one or more embodiments, apparatus 100 and/or computing device 110 may include or be communicatively connected to one or more input output (I/O) devices 118. For the purposes of this disclosure, an input/output (I/O) device is a hardware component or peripheral that facilitates an exchange of data between a computing device and external entities. An I/O device may be configured to receive input signals (such as, without limitation, from a sensor) and/or provide output signals (such as, without limitation, to display 116). An I/O device typically operates by transmitting electrical signals that are processed by a computing device, thereby allowing interaction with external systems or users in a controlled manner. I/O device 118 may include any suitable device configured to receive input from a practitioner or communicate an output to the practitioner. In some cases, I/O device 118 may include an activation mechanism and/or a user actuated element (e.g., a touch button, a push button, a switch, a touchpad, keyboard, and/or the like) to control computing device 110 and/or a stimulation device. In one or more embodiments, I/O device 118 may allow a practitioner to enter information or request information (e.g., patient information or the like), to adjust stimulation parameters for stimulation, to create, update, delete, or otherwise modify a stimulation protocol, and/or to initiate the stimulation protocol. In some cases, I/O device 118 may optionally include or be operatively coupled to a touchscreen, a keyboard, or other input device for receiving information from a practitioner. Display 116 and/or other I/O device(s) 118 may each be configured to interface with a practitioner and relay information to and from processor 112 and memory 114 of computing device 110. Additional details will be provided below.

With continued reference to FIG. 1A, apparatus 100 further includes a stimulation device 120 communicatively connected to processor 112. For the purposes of this disclosure, a stimulation device is a device configured to deliver one or more electrical stimuli, mechanical stimuli, thermal stimuli, and/or the like to one or more targeted tissues and/or nerves to achieve one or more therapeutic effects and/or diagnostic outcomes. A stimulation device is often configured to generate controlled stimulation signals, which may be used to modulate nerve activity, promote muscle function, manage pain, and/or stimulate tissue regeneration. A stimulation device typically incorporates sensors for feedback control, thereby ensuring that precise and safe stimulation parameters are maintained based on physiological conditions and/or pre-programmed protocols.

With continued reference to FIG. 1A, stimulation device 120 may include or be electrically connected to one or more electrodes 122 and is configured to control an electrical output (e.g., current pulses) from the one or more electrodes 122. The target location of electrode 122 with respect to a spine may be determined by a practitioner prior to implantation, based on factors such as, without limitation, symptoms, physiology, and/or diagnosis of the patient. The position of one or more electrodes 122 with respect to an FML and the parameters associated with their implementation may be collectively referred to as the "functional positioning" of the one or more electrodes 122, as described in further detail below. In one or more embodiments, electrode 122 may include a paddle electrode. In one or more embodiments, electrode 122 may include a percutaneous electrode. Specifically, for a paddle electrode, larger, flat electrodes 122 may often be arranged bilaterally; whereas for percutaneous electrodes, thin, column-like electrodes 122 may be typically inserted as two individual electrodes 122 on either side of a spinal cord. For the purposes of this disclosure, an electrode is a conductive device, often used to interface with biological tissues, that enables a delivery and/or detection of electrical signals and/or electrical activity. An electrode may be configured to transmit an electrical impulse to tissues, such as, without limitation, nerves or muscles, or to detect bioelectrical activity for diagnostic purposes. As a nonlimiting example, one or more electrodes may be integrated into a medical device for therapeutic applications, such as, without limitation, electrical stimulation, and/or for monitoring physiological parameters, consistent with details described above. Nonlimiting types of electrodes may include surface electrodes, which may be placed on the skin for monitoring or stimulation of biological activities; needle electrodes, which may be inserted into tissues to record or stimulate electrical activity; microelectrodes, which may have a relatively small surface area and be used for detecting activity in a localized or region (e.g., neural recording and/or the like); and implantable electrodes, which may be used for long-term placement in tissues (e.g., pacemakers, deep brain stimulators, and/or the like). An electrode is typically constructed using a biocompatible material or a combination of biocompatible materials to ensure safe and effective contact with tissues. The choice of material for an electrode may further depend on various factors such as, without limitation, the desired durability, conductivity, flexibility, and/or antifouling properties of the electrode, among others, and such choice may vary based on the exact use case. An electrode (or one or more parts thereof) may be constructed using inorganic/metallic materials such as, without limitation, platinum, gold, titanium, stainless steel, iridium, and/or silver and silver-containing compounds (e.g., AgCl and/or the like), among others. An electrode (or one or more parts thereof) may be constructed using one or more carbon-based materials, such as, without limitation, glassy carbon, carbon paste, graphite, graphene, carbon fiber, carbon nanotube, and/or the like. An electrode (or one or more parts thereof) may be constructed using one or more conductive polymers, such as, without limitation, polyphenylenevinylene (PPV), poly(3,4-ethylenedioxythiophene (PEDOT), polypyrrole (PPy), polythiophene (PT), polyacetylene (PA), etc. A person of ordinary skill in the art, upon reviewing the entirety of this disclosure, will be able to recognize suitable materials not disclosed herein but with satisfactory biocompatibility and conductivity that may be used for construction of an electrode.

With continued reference to FIG. 1A, as a nonlimiting example, a plurality of electrodes 122 may be deployed using an electrode lead and configured to be implanted in tissue in proximity to the spinal cord of the patient. Exemplary types of electrode leads may include without limitation percutaneous cylindrical electrode leads, paddle electrode leads, or the like, as deemed suitable by a person of ordinary skill in the art, upon reviewing the entirety of this disclosure. For the purposes of this disclosure, an electrode lead is a conductive wire or cable that connects an electrode to a medical device, facilitating the transmission of electrical signals between the electrode and the medical device. An electrode lead may be essential in delivering electrical impulses to tissues or recording electrical activity from the body (such as, without limitation, in pacemakers, defibrillators, or neurostimulators, among others). Typically, an electrode lead is constructed using biocompatible materials, consistent with details described above, and is designed to ensure secure and accurate signal transmission within a medical system.

With continued reference to FIG. 1A, apparatus 100 further includes one or more sensors 132 communicatively connected to computing device 110. In one or more embodiments, sensor 132 may include one or more EMG sensors configured to detect EMG signals and/or record EMG data, consistent with details described above. In some cases, a plurality of sensors 132 may be deployed or positioned over one or more target muscles (TM) on the LS of the patient and over one or more target muscles TM on the RS of the patient. Plurality of sensors 132 may be configured to measure EMG data and then send them to computing device 110 for downstream processing and/or analysis. In one or more embodiments, plurality of sensors 132 may be implemented as a sensor array. Computing device 110 may be configured accordingly to process and/or analyze the EMG data and output information corresponding to the analyzed EMG data (e.g., via a display). The output information may then aid a practitioner in placing one or more electrodes 122 over a target location in order to facilitate a stimulation of desired nerve roots and an activation of desired myotomes associated thereto. For the purposes of this disclosure, a sensor is a device designed and/or configured to detect and measure specific physiological or environmental parameters and convert these signals into electrical or digital data for monitoring, analysis, or control. A sensor may measure variables such as, without limitation, temperature, pressure, glucose levels, heart rate, oxygen saturation, among others, and is typically integrated into a device to provide real-time feedback. A sensor may operate within predefined accuracy and sensitivity thresholds, ensuring reliable, safe, and precise data for diagnostic or therapeutic purposes.

With continued reference to FIG. 1A, for the purposes of this disclosure, a "signal" is an intelligible representation of data that is often transmitted from one device to another. A signal may include an optical signal, a hydraulic signal, a pneumatic signal, a mechanical signal, an electric signal, a digital signal, an analog signal, and the like. In some cases, a signal may be used to communicate with a computing device, such without limitation computing device 110, for example by way of one or more ports. In some cases, a signal may be transmitted and/or received by a computing device for example by way of an input/output port. An analog signal may be digitized, for example by way of an analog to digital converter. In some cases, an analog signal may be processed, for example by way of any analog signal processing steps described in this disclosure, prior to digitization. In some cases, a digital signal may be used to communicate between two or more devices, including without limitation computing devices. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 128 [printer port]), and the like. Specifically, signals detected by one or more sensors 132 may include physiological data and/or biosignals, such as without limitation electromyogram data, electroencephalogram data, electrocardiogram data, temperature, blood pressure, respiratory rate, oxygen saturation, and/or the like, consistent with details described elsewhere in this disclosure.

With continued reference to FIG. 1A, a signal detected by sensor 132 may first be processed before being used by apparatus 100 and/or computing device 110 for downstream tasks. For instance, apparatus 100 and/or computing device 110 may analyze, modify, and/or synthesize a signal representative of data in order to improve the signal, for instance by improving transmission, storage efficiency, or signal to noise ratio. Exemplary methods of signal processing may include analog, continuous time, discrete, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, and phase-locked loops. Continuous-time signal processing may be used, in some cases, to process signals which vary continuously within a domain, for instance time. Nonlimiting examples of continuous time processes may include time domain processing, frequency domain processing (Fourier transform), and/or complex frequency domain processing, among others. Discrete time signal processing may be used when a signal is sampled non-continuously or at discrete time intervals (i.e., quantized in time). Analog discrete-time signal processing may process a signal using the following exemplary circuits, such as without limitation sample and hold circuits, analog time-division multiplexers, analog delay lines, and/or analog feedback shift registers, among others. Digital signal processing may be used to process digitized discrete-time sampled signals. Commonly, digital signal processing may be performed by a computing device or other specialized digital circuits, such as, without limitation, an application specific integrated circuit (ASIC), a field-programmable gate array (FPGA), or a specialized digital signal processor (DSP). Digital signal processing may be used to perform any combination of typical arithmetical operations, including without limitation fixed-point and floating-point, real-valued and complex-valued, multiplication and addition, etc. Digital signal processing may additionally operate circular buffers and lookup tables. Further nonlimiting examples of algorithms that may be performed according to digital signal processing techniques include fast Fourier transform (FFT), finite impulse response (FIR) filter, infinite impulse response (IIR) filter, and adaptive filters such as without limitation the Wiener and Kalman filters. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal.

With continued reference to FIG. 1A, in one or more embodiments, processor 112 may be configured to communicate one or more signals to or from memory 114, display 116, stimulation device 120, one or more sensors 132, and/or one or more other elements of apparatus 100 to activate and/or control an operation of such element(s). In one or more embodiments, processor 112 may be configured to execute modules, processes, and/or functions associated with activating one or more electrodes 122, processing and/or analyzing data from one or more sensors 132, and/or the like. Processor 112 may be configured to receive information input by a user via I/O device 118 to generate instructions for stimulating tissue and send the generated instructions to stimulation device 120. As a nonlimiting example, processor 112 may be configured to control and/or modify various stimulation parameters. Additional details will be provided below in this disclosure.

With continued reference to FIG. 1A, processor 112 may be configured to control stimulation device 120 to provide stimulation via electrodes 122, consistent with details described above. Additionally, processor 112 may be configured to process and/or analyze EMG data collected by one or more sensor(s) 132, consistent with details described above. The underlying device technologies pertaining to apparatus 100 may be provided in a variety of component types, such as metal-oxide semiconductor field-effect transistor (MOSFET) technologies including without limitation complementary metal-oxide semiconductor (CMOS), bipolar technologies including without limitation generative adversarial network (GAN), polymer technologies including without limitation silicon-conjugated polymer and metal-conjugated polymer-metal structures, mixed analog and digital technologies, and/or the like. Additional details will be provided below in this disclosure.

With continued reference to FIG. 1A, in one or more embodiments, computing device 110 may include I/O channels for sending information to stimulation device 120 and/or one or more electrodes 122 and/or for receiving information from one or more sensors 132. In one or more embodiments, computing device 110 may include up to 32 I/O channels for connecting to electrodes 122, which may include one or more recording electrodes (e.g., the reference electrodes) and/or one or more stimulating electrodes (e.g., the active or working electrode). In one or more embodiments, computing device 110 may include greater than 32 I/O channels for connecting to recording electrodes and/or stimulating electrodes. In one or more embodiments, computing device 110 may include I/O channels for connecting to EMG inputs. In one or more embodiments, computing device 110 may include 8 or more I/O channels for connecting to one or more sensors 132. In one or more embodiments, computing device 110 may include a total of 40 or more I/O channels for connecting to one or more electrodes 122 and/or one or more sensors 132.

With continued reference to FIG. 1A, processor 112 is configured to instruct stimulation device 120 to implement a stimulation protocol. For the purposes of this disclosure, a stimulation protocol is a set of activation instructions that, once executed by processor 112, specifies how stimulation device 120 implements a stimulation procedure and one or more relevant parameters associated thereto. "Stimulation protocol" and "stimulation scheme" may be used interchangeably throughout this disclosure. In one or more embodiments, stimulation protocol may include a plurality of stimulation parameters. For the purposes of this disclosure, a stimulation parameter is a parameter describing one or more aspects of how a stimulation procedure is performed. In one or more embodiments, a stimulation parameter may include without limitation a pulse amplitude including peak amplitude, average amplitude, and/or the like; a pulse width including without limitation a full width at half maximum (FWHM) and/or the like; a pulse duration; a pulse shape including without limitation a Gaussian, Lorentzian, exponential, sinusoidal, rectangular, triangular, exponential, Sawtooth, Hamming, or Ricker shape, among others; a pulse sequence; a pulse frequency; a repetition rate; energy delivered per pulse; and/or a duty cycle, among others. In one or more embodiments, a stimulation parameter may include or specify an initial positioning of stimulation device 120 and/or one or more electrodes 122 disposed therein or communicatively connected thereto. In one or more embodiments, a stimulation parameter may include one or more inter-pulse parameters, such as, without limitation, how a first pulse generated by a first electrode 122 spatially and/or temporally correlates to a second pulse generated by a second electrode 122.

With continued reference to FIG. 1A, in one or more embodiments, a stimulation protocol may include instructions for incrementally stepping through values within a predetermined range for each stimulation parameter. In one or more embodiments, a stimulation protocol may include instructions to cycle through each stimulation parameter for an electrode 122, or a pair of electrodes 122, before repeating this process for a subsequent electrode or pair of electrodes. In some cases, processor 112 may be configured to instruct stimulation device 120 to generate pulses for a first activated electrode 122 that incrementally ramp up in current amplitude while holding all other parameters (e.g., frequency, duty cycle, and active electrode pair) constant. Then, processor 112 may be configured to sweep through the next parameter such as, without limitation, frequency, while holding the remaining parameters constant. As a nonlimiting example, processor 112 may be configured to instruct stimulation device 120 to sweep through current amplitudes between approximately 0 mA and approximately 200 mA, with a step size of between approximately 0.1 mA and approximately 2 mA. Alternatively, the step size may be between approximately 0.5 mA to approximately 1 mA. Similarly, as another nonlimiting example, processor 112 may instruct stimulation device 120 to sweep through frequencies between approximately 1 Hz to approximately 1000 Hz, with a step size between approximately 0.1 Hz and approximately 10 Hz. As another nonlimiting example, stimulation device 120 may be instructed to sweep through frequencies between approximately 1 Hz and approximately 10 Hz with a step size between approximately 0.5 Hz and approximately 1 Hz. As another nonlimiting example, the pulse width used may be between approximately 0.001 milliseconds (ms) and approximately 500 ms. As another nonlimiting example, the pulse width may be held at approximately 200 ms. In one or more embodiments, the parameters may be ramped up linearly. In one or more embodiments, the parameters may be ramped up non-linearly according to a predetermined function. In one or more embodiments, only a subset of the stimulation parameters may be adjusted. In one or more embodiments, processor 112 may instruct stimulation device 120 to only cycle through current amplitude values and/or frequency values.

With continued reference to FIG. 1A, in one or more embodiments, a predetermined range for testing each stimulation parameter may be chosen beforehand based on safety considerations and/or common ranges that achieve a myotome or muscle response. In one or more embodiments, stimulation parameters used in apparatus 100 for placement of electrodes may be different than the stimulation parameters used for therapeutic stimulation. As a nonlimiting example, the amplitude and frequency of the current pulses used to facilitate a placement of electrodes may be lower than the corresponding stimulation parameters used in therapeutic stimulation in order to increase the likelihood of isolated myotome activation for positioning feedback.

With continued reference to FIG. 1A, in one or more embodiments, stimulation may occur using electrode pairs including one active electrode 122 and one reference electrode 122, consistent with details described above. In one or more embodiments, processor 112 may be configured to assign electrodes 122 on an implanted electrode lead as an active electrode or a reference electrode. After stimulation device 120 cycles through stimulation parameters for a given active/reference electrode pair, processor 112 may be configured to activate the next electrode pair on the electrode lead.

With continued reference to FIG. 1A, in one or more embodiments, processor 112 may control stimulation device 120 to activate one or more electrodes 122 or electrode pairs in a rostral-to-caudal direction. In one or more embodiments, processor 112 may be configured to control stimulation device 120 to activate a plurality of electrodes 122 in pairs, quadrants, and/or other types of groupings, consistent with details described above.

With continued reference to FIG. 1A, stimulation device 120 is configured to control an electrical output of one or more electrodes 122. In one or more embodiments, stimulation device 120 may include or be communicatively connected to an amplifier. In one or more embodiments, stimulation device 120 may be configured as a pulse generator. Stimulation device 120 may generate electrical pulses through one or more electrodes 122 with predetermined parameters based on preset protocols and/or based on information input by a practitioner to computing device 110. In one or more embodiments, stimulation device 120 may generate current pulses based on parameters according to instructions from processor 112. Parameters that may be controlled include without limitation amplitude, frequency, duty cycle, pulse width, and/or repetition rate, among others, consistent with details described elsewhere in this disclosure. In one or more embodiments, the position of one or more electrodes 122 may also be an adjustable parameter. In one or more embodiments wherein an electrode lead is implanted, a combination of multiple electrodes 122 that are activated for stimulation may also be an adjustable parameter for controlling the electric field generated by stimulation device 120.

With continued reference to FIG. 1A, one or more electrodes 122 may be configured to provide electrical stimulation to tissue in proximity to a spinal cord. In one or more embodiments, one or more electrodes 122 may be disposed on a percutaneous cylindrical lead. In one or more embodiments, one or more electrodes 122 may be deployed on a percutaneous paddle lead. In one or more embodiments, one or more electrodes 122 may include or be implemented using a commercially available implantable lead. In one or more embodiments, an electrode lead may include between 2 electrodes 122 and 32 electrodes 122. In one or more embodiments, an electrode lead may include 8 electrodes 122.

With continued reference to FIG. 1A, in one or more embodiments, apparatus 100 may include an even number of sensors 132 such that they may be positioned symmetrically over muscles on the LS of the patient and the RS of the patient. In one or more embodiments, a plurality of sensors 132 may be positioned over predetermined myotomes and/or muscles on the LS of the body and the RS of the body. As a nonlimiting example, a plurality of sensors 132 may be placed bilaterally over the psoas, the quadriceps (quads), the tibialis anterior (TA), the vastus lateralis (VL), and/or the abductor hallucis (AH). In one or more embodiments, apparatus 100 may include from 2 sensors 132 to 16 sensors 132. In one or more embodiments, apparatus 100 may include 8 or more sensors 132. In one or more embodiments, apparatus 100 may include 2 sensors 132, 4 sensors 132, or 8 sensors 132. In one or more embodiments, the target muscles TM over which one or more sensors 132 are positioned may depend on a region of the body in which the patient is experiencing pain. It is worth noting that sensor(s) 132 described herein may not be limited to EMG sensors only, as one or more alternative sensors 132 may be utilized to measure a response of a nerve, muscle, and/or myotome to an applied stimulation. As a nonlimiting example, one or more recording electrodes 122 configured to measure action potentials (AP) of downstream nerves and/or compound muscle activation potentials (cMAP) may be used. For the purposes of this disclosure, an action potential is a rapid change in voltage across a cell membrane, or membrane potential, that serves as an electrical signal. For the purposes of this disclosure, a compound motor action potential (cMAP) is the sum of APs from multiple muscle fibers that are stimulated by a single nerve impulse. cMAPs are often used in electrodiagnostic medicine to assess muscle function and may be used as an indicator of muscle strength and hypertrophy. cMAPs are often recorded during a motor nerve conduction study, where stimulation of the motor nerve activates muscle fibers. A cMAP may provide information pertaining to the neuromuscular junction, descending motor axons, and/or muscle fibers that were activated and accordingly detect and assess a disease or condition in such regions.

With continued reference to FIG. 1A, in one or more embodiments, prior to running a stimulation protocol, processor 112 may be configured to perform a test protocol to test the placement of one or more sensors 132, thereby ensuring adequate surface contact, location, and/or signal quality. In one or more embodiments, processor 112 may be configured to optimize the biosignals to ensure that signal data with an improved or optimized quality can be collected prior to implementing the stimulation protocol and interpreting the biosignals. For instance, a signal-to-noise ratio (SNR) may be calculated and used to evaluate the quality regarding the placement of one or more sensors 132. In some embodiments, electrode noise, motion artifacts, and other types of interference may be reduced during a signal pre-processing step. In one or more embodiments, if the SNR is below a predetermined threshold, the one or more sensors 132 may be re-adhered and/or repositioned. In one or more embodiments, processor 112 may be configured to process and/or analyze EMG data received from one or more sensors 132 and to use display 116 to display information related to the processed and/or analyzed EMG data, as described in further detail below with respect to FIG. 2.

With continued reference to FIG. 1A, in one or more embodiments, computing device 110 may include universal connectors to allow seamless integration with existing electrode systems and/or sensor(s) 132. While not depicted, computing device 110 may also include an onboard power supply or be operatively coupled to a power supply (e.g., via a cable) that may be configured to supply electrical power to any components of the computing device 110. Suitable power sources pertaining to apparatus 100 may include, without limitation, a wall outlet, a generator, a photovoltaic device, a fuel cell such as without limitation a hydrogen fuel cell, direct methanol fuel cell, and/or solid oxide fuel cell, or an electric energy storage device. An electric energy storage device may include without limitation a battery, capacitor, and/or inductor. A power source and/or energy storage device may include at least a battery, a battery cell, and/or a plurality of battery cells connected in series, in parallel, or in a combination of series and parallel connections such as series connections into modules that are connected in parallel with other like modules. A battery and/or battery cell may include elements such as, without limitation, lithium nickel cobalt aluminum oxides, nickel manganese cobalt oxide, lithium iron phosphate, and lithium manganese oxide cathodes, which may be mixed with one another or with another cathode material to provide more specific power as required by the application. A battery and/or battery cell may include lithium metal anodes that provide high power on demand. A battery and/or battery cell may include silicon or titanite anode. In one or more embodiments, a battery or battery cell may include, without limitation, a battery using nickel-based materials such as nickel cadmium or nickel metal hydride, a battery using lithium ion battery materials such as a nickel cobalt aluminum oxide, nickel manganese cobalt oxide, lithium iron phosphate, lithium cobalt oxide, and/or lithium manganese oxide, a battery using lithium polymer technology, lead-based batteries such as without limitation lead acid batteries, metal-air batteries, or any other suitable alternative. A person of ordinary skill in the art, upon reviewing the entirety of this disclosure, will be aware of various devices of components that may be used as power source.

Figure 1B:
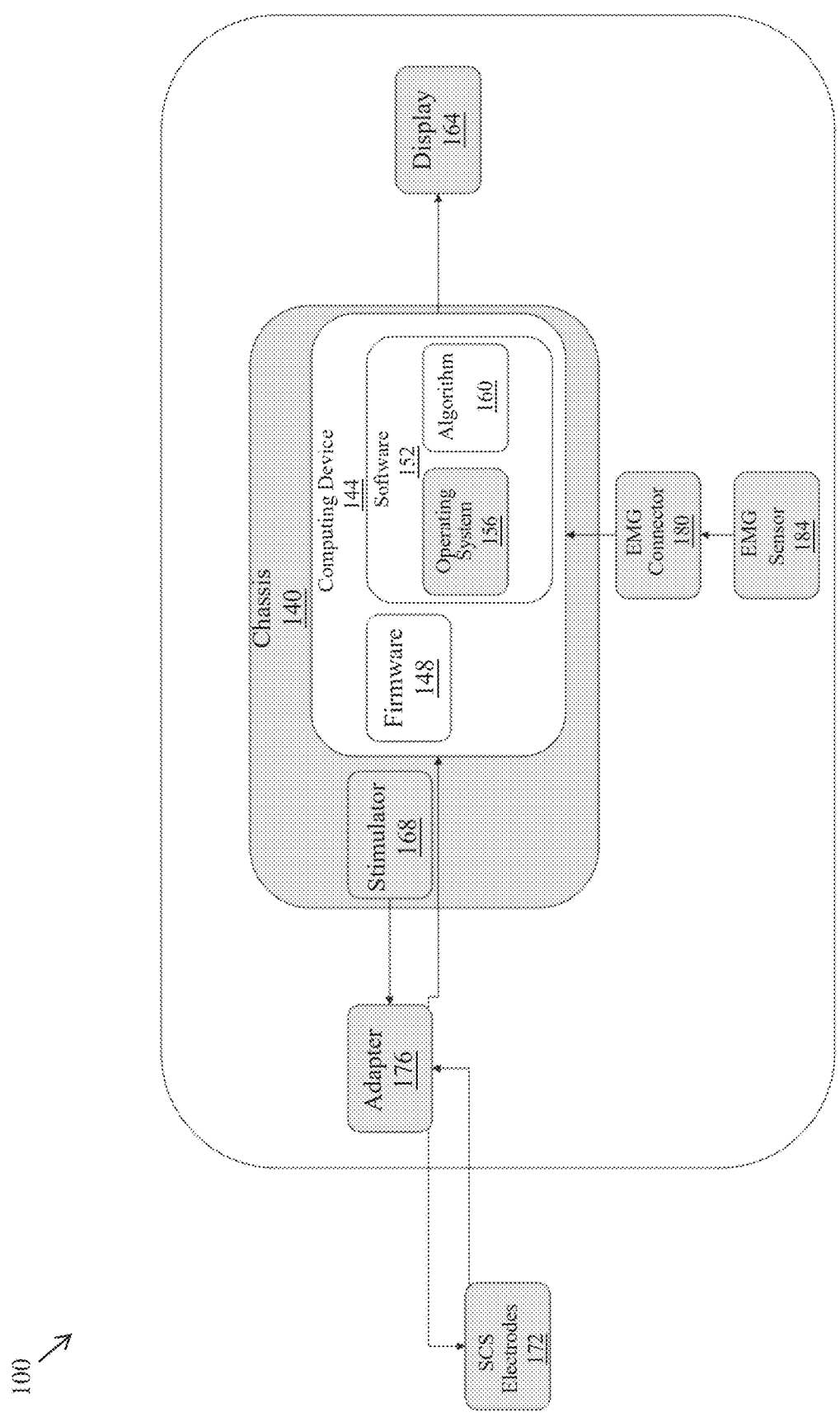
FIG. 1B is a schematic block diagram illustrating an exemplary embodiment of a detailed organizational structure of the apparatus described in FIG. 1A.

Referring now to FIG. 1B, FIG. 1B is a schematic block diagram illustrating an exemplary embodiment of a detailed organizational structure of apparatus 100 described in FIG. 1A. Apparatus 100 may include a chassis 140, wherein a computing device 144 is enclosed within the chassis 140. For the purposes of this disclosure, a (computer) chassis, also known as a computer case, is the physical structure that supports a computer's internal components and protects them from damage. Computing device 144 may include firmware 148 configured to operate hardware within the computing device 144. Computing device 144 may include software 152 such as without limitation an operation system 156 and/or one or more algorithms 160 that may be used to implement one or more aspects of the invention described herein. Chassis 140 may be communicatively connected to a display 164, wherein a user may interact with display 164 using a graphical user interface. In some cases, display 164 may include a touch screen. In some embodiments, chassis 140 may include a stimulator 168 communicatively connected to computing device 144. One or more spinal cord stimulator (SCS) electrodes 172 may be communicatively connected to computing device 144 through an adapter 176. Chassis 140 may be communicatively connected to one or more EMG sensors 180, such as without limitation through one or more EMG connectors 184.

Figure 2:
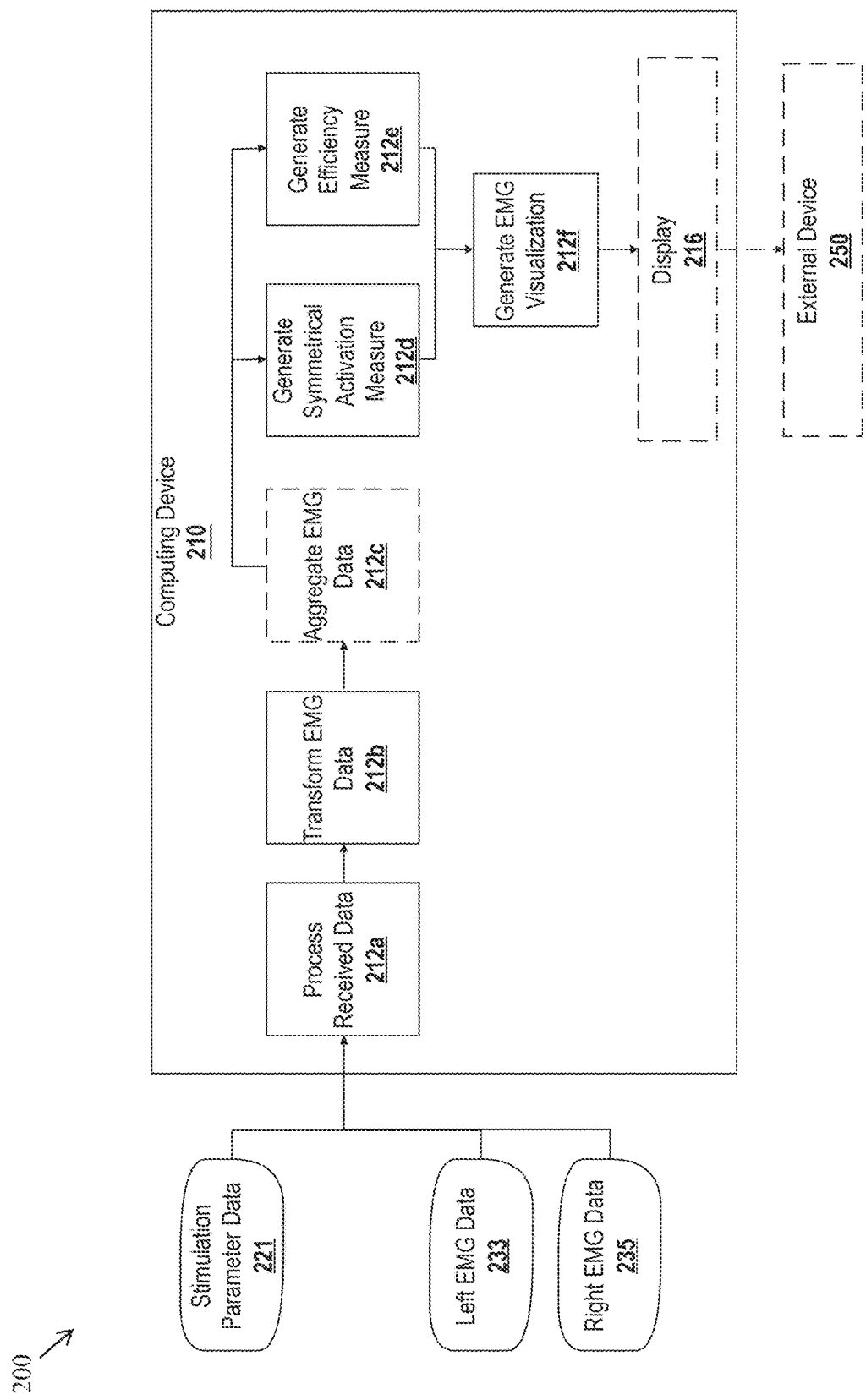
FIG. 2 is a schematic block diagram illustrating an exemplary embodiment of a workflow for processing stimulation data and/or EMG data to guide electrode placement.

Referring now to FIG. 2, FIG. 2 includes a schematic block diagram describing an exemplary embodiment of a workflow 200 pertaining to apparatus 100. Specifically, workflow 200 contains steps to be completed by a computing device 210 in order to process and display EMG data for guiding electrode placement. Computing device 210 may include any structural and/or functional feature or features described above pertaining to computing device 110 without limitation. In one or more embodiments, computing device 210 may be configured to receive stimulation parameter data 221. Stimulation parameter data 221 may include any data pertaining to a stimulation procedure, such as, without limitation, data related to one or more stimulation parameters used, timing of stimulation, etc., among others, consistent with details described above. In one or more embodiments, stimulation parameter data 221 may include one or more waveforms output by stimulator device 120, consistent with details described above. In one or more embodiments, stimulation parameter data 221 may include one or more parameter values used, such as, without limitation, in a .csv file, a .txt file, or the like.

With continued reference to FIG. 2, in one or more embodiments, stimulation parameter data 221 may include metadata. For the purposes of this disclosure, metadata are structured data that provides detailed information about another set of data. Metadata may include descriptors such as, without limitation, the source, format, creation date, context, etc., of medical records, imaging files, lab results, and/or patient health information, among others. Metadata may help categorize and manage clinical data for efficient retrieval, integration, and analysis and may be critical for maintaining data integrity, ensuring compliance with regulations (e.g., HIPAA), and supporting interoperability among different healthcare systems or devices. In one or more embodiments, metadata may include data pertaining to the timing of a stimulation output. In one or more embodiments, metadata may include data pertaining to the timing of one or more EMG recordings such that the EMG data may be aligned with a stimulation waveform. In one or more embodiments, metadata may include information corresponding to one or more myotomes over which one or more sensors 132, such as, without limitation, one or more EMG sensors, were placed.

With continued reference to FIG. 2, in one or more embodiments, computing device 210 may be configured to receive left EMG data 233 and right EMG data 235. For the purposes of this disclosure, left or left-side EMG data are EMG data collected from the LS of a patient. Accordingly, for the purposes of this disclosure, right or right-side EMG data are EMG data collected from the RS of a patient. In one or more embodiments, left EMG data 233 may include EMG sensor data from one or more myotomes on the LS of the body of a patient. Accordingly, in one or more embodiments, right EMG data 235 may include EMG sensor data from one or more myotomes on the RS of the body of the patient.

With continued reference to FIG. 2, upon receiving the data described above, at step 212a, workflow 200 includes processing the received data. Step 212a may be performed using one or more processors 112 consistent with details described above. In one or more embodiments, the EMG data may be cleaned and/or smoothed. In one or more embodiments, one or more filters may be applied to the data, consistent with details described above. As a nonlimiting example, one or more of a low-pass filter, a high-pass filter, and/or a notch filter may be applied. In one or more embodiments, at step 212a, processing the received data may include processing EMG data by amplifying one or more EMG signals, removing noise artifacts from the EMG signals, and/or performing any other suitable processing steps to prepare the EMG data for further downstream analysis, as recognized by a person of ordinary skill in the art, upon reviewing the entirety of this disclosure. In some cases, filtering EMG data may include extracting one or more features or events from the EMG data and improving the signal-to-noise ratio thereof.

With continued reference to FIG. 2, at step 212b, workflow 200 further includes transforming EMG data using computing device 210. In one or more embodiments, the EMG data may be transformed into a frequency domain. As nonlimiting examples, one or more of a Fast Fourier Transform (FFT), a Short Time Fourier Transform (STFT), a Wavelet Transform (WT), among others, may be applied to transform the EMG data.

With continued reference to FIG. 2, optionally, in one or more embodiments, at step 212c, workflow 200 may further include aggregating the EMG data from multiple target myotomes or muscles using computing device 210. As a nonlimiting example, the processed and transformed EMG data collected at each myotome on the LS of a patient's body may be aggregated and averaged, and accordingly, the processed and transformed EMG data collected at each myotome on the RS of the patient's body may be aggregated and averaged. In one or more embodiments, the EMG data may be aggregated based on other criteria, such as, without limitation, one or more regions of the body, the size of a muscle or myotome, one or more most relevant muscles or myotomes, among others.

With continued reference to FIG. 2, an analysis of EMG signals may occur in the frequency or temporal domain to (1) determine a level of muscle or myotome activation that is occurring in response to an electrical stimulation; (2) to determine a degree of symmetry or asymmetry of muscle or myotome activation between the LS and RS of a patient; and (3) to determine a magnitude of stimulation required to activate a muscle or myotome. Accordingly, at step 212d, workflow 200 may further include generating a symmetrical activation measure. Similarly, at step 212e, workflow 200 may further include generating an efficiency measure. Additional details will be provided below in this disclosure. In one or more embodiments, an EMG signal may be analyzed by calculating one or more of a maximum amplitude of the signal, an average amplitude of the signal, a median amplitude of the signal, a root mean square (RMS) amplitude of the signal, a spectral density of the signal, a slope between certain points of the signal, a first derivative of the signal, a curvature of the signal, and/or a second derivative of the signal, among others.

With continued reference to FIG. 2, in one or more embodiments, a strength of muscle activation may be calculated, such as, without limitation, as an activation ratio. For the purposes of this disclosure, an "activation ratio" is a measure regarding how a signal measured under an active state of a subject compares to the same signal measured under a resting state of the same subject. The subject may include one or more muscles, myotomes, or the like, consistent with details described above. As a nonlimiting example, an activation ratio may be calculated by finding the ratio between a first EMG response during a stimulation procedure and a second EMG response without any externally applied stimulation. The first EMG response may include without limitation a maximum amplitude, an average amplitude, a median amplitude, an RMS amplitude, and/or the like, measured during a time period/at a timepoint when a stimulation is applied to one or more muscles or myotomes. In contrast, as another nonlimiting example, the second EMG response may include without limitation a signal amplitude measured during a time period/at a timepoint with no applied stimulation (e.g., before a stimulation period, after a stimulation period, or between two adjacent stimulation periods). As another nonlimiting example, an activation ratio may be calculated as a ratio between a first RMS amplitude of an EMG signal during a time period when a stimulation is applied, and a second RMS amplitude of the EMG signal when it is at a baseline level.

With continued reference to FIG. 2, at step 212d, workflow 200 further includes generating a symmetrical activation measure using computing device 210. For the purposes of this disclosure, a "symmetrical activation measure" is an indication that describes a relative level of activation by comparing a first activation of one or more muscles/myotomes on the LS of the body and a second activation of one or more muscles/myotomes on the RS of the body. As a nonlimiting example, if a plurality of EMG sensors measures equal or substantially equal levels of activation on the RS of the body versus the LS of the body, then a symmetrical activation measure may indicate a bilateral activation. In contrast, if a plurality of EMG sensors measures a substantially stronger or weaker activation on the RS of the body with respect to the LS of the body, then a symmetrical activation measure may indicate a strong right activation or left activation, respectively. A symmetrical activation measure may indicate to a practitioner, such as a physician, a relative placement of one or more electrodes 122 with respect to the FML of a patient, consistent with details described above in this disclosure. Similarly, additionally, and/or alternatively, in some cases, at step workflow 200 may further include generating an asymmetrical activation measure using computing device 210 instead of, or in addition to, a symmetrical activation measure.

With continued reference to FIG. 2, at step 212*e*, workflow 200 further includes generating an activation efficiency measure using computing device 210. For the purposes of this disclosure, an activation efficiency is a measure describing the magnitude of a stimulation that needs to be applied before an activation occurs. An efficiency measure may indicate how easy or difficult it is for a muscle or myotome to be activated. As a nonlimiting example, if a myotome or muscle is activated in response to a low-amplitude stimulation, the myotome or muscle may accordingly have a high activation efficiency measure. In contrast, if a higher amplitude of stimulation (i.e., a stronger stimulation) is required to activate a muscle or myotome, then the muscle or myotome may have a low activation efficiency measure. In other words, an activation efficiency measure may describe how sensitive a muscle or myotome is.

With continued reference to FIG. 2, in one or more embodiments, lateralization of an electrode lead may be completed. For the purposes of this disclosure, lateralization is a process that involves stimulating one side or region of the body to result in a motor or sensory response primarily on the corresponding side of the body. Lateralization typically involves selectively targeting specific nerves or pathways to achieve asymmetric effects, such as left or right-sided muscle contractions or sensory responses. Lateralization may be particularly important in spinal cord stimulation devices, where a controlled lateralization may be used for therapeutic purposes, such as, without limitation, pain management and/or motor function restoration, among others. In some cases, a lateralization process may include measuring an RMS value of the EMG data for each myotome and in response to each electrode 122 in an electrode lead. A lateralization ratio may then be calculated between the RMS value of a specific electrode 122 in the array and the RMS values of other electrodes 122 in the array. In some cases, a lateralization ratio may be calculated by dividing an EMG response within a given time period by an EMG signal from the same time period for a corresponding muscle/myotome on the opposite side of the body. In some cases, a lateralization process may further include designating an electrode 122 as a left contact based on a lateralization ratio being less than 1. Accordingly, in some cases, a lateralization process may further include designating an electrode 122 as a right contact based on a lateralization ratio being less than 1. Accordingly, in some cases, lateralization may further include designating an electrode 122 as a midpoint contact based on a lateralization ratio being equal to or substantially equal to 1. In some cases, computing device 210 may be configured to connect the coordinates of contact points that are designated as the midpoint contacts to define an FML. In one or more embodiments, the FML may subsequently be output to an external device 250. Additional details will be provided below in this disclosure.

With continued reference to FIG. 2, at step 212*f*, workflow 200 further includes generating and/or outputting a visualization of EMG data, consistent with details described above pertaining to FIGS. 1A-B. In one or more embodiments, such visualization may include a functional map of a spinal cord. In one or more embodiments, such visualization may include a graphical representation of an activation ratio, a symmetrical activation measure, and/or an activation efficiency measure, consistent with details described above. In one or more embodiments, such visualization may include a chart visualizing an activation ratio, a symmetrical activation measure, and/or an efficiency measure. The visualization of EMG data will be described in further detail with respect to FIGS. 6-9. In one or more embodiments, apparatus 100 may be configured to calculate and/or display one or more metrics of interest. As a nonlimiting example, such metrics of interest may include without limitation one or more absolute metrics, such as without limitation one or more coordinates describing one or more specific regions of a patient's body. As another nonlimiting example, such metrics of interest may include one or more comparative metrics, such as without limitation the relative position of one or more electrodes 122 with respect to one or more target locations, consistent with details described elsewhere in this disclosure.

With continued reference to FIG. 2, in one or more embodiments, computing device 210 may be configured to store and/or retrieve, via a memory or data repository as described above, current and/or historical information collected during an electrode placement procedure. In one or more embodiments, a practitioner such as a physician may refer to both current and/or historical information to reach an intended target site for stimulation device 120 and/or one or more electrodes 122 integrated therein or communicatively connected thereto. In one or more embodiments, computing device 210 may be configured to display a generated EMG visualization via a display 216. Display 216 may be implemented in any manner consistent with details described above pertaining to display 116 without limitation. As a nonlimiting example, display 216 may be configured to display information related to current electrode positioning as well as prior electrode positioning.

With continued reference to FIG. 2, in one or more embodiments, computing device 210 may be configured to send information related to an electrode placement procedure to an external device 250. For the purposes of this disclosure, an "external device" is a device that is independent from computing device 110/210 and configured to perform one or more functions related to apparatus 100 and/or workflow 200. In some cases, external device 250 may include or function as a data repository. As a nonlimiting example, computing device 210 may transfer raw EMG data, processed EMG data, aggregated EMG data, visual representations of the EMG data, stimulation parameter data, patient information, practitioner notes, among others, to external device 250 for storage and/or further downstream processing. In one or more embodiments, computing device 210 may be configured to retrieve the information stored in external device 250 when needed.

Placement Procedure

Figure 3:
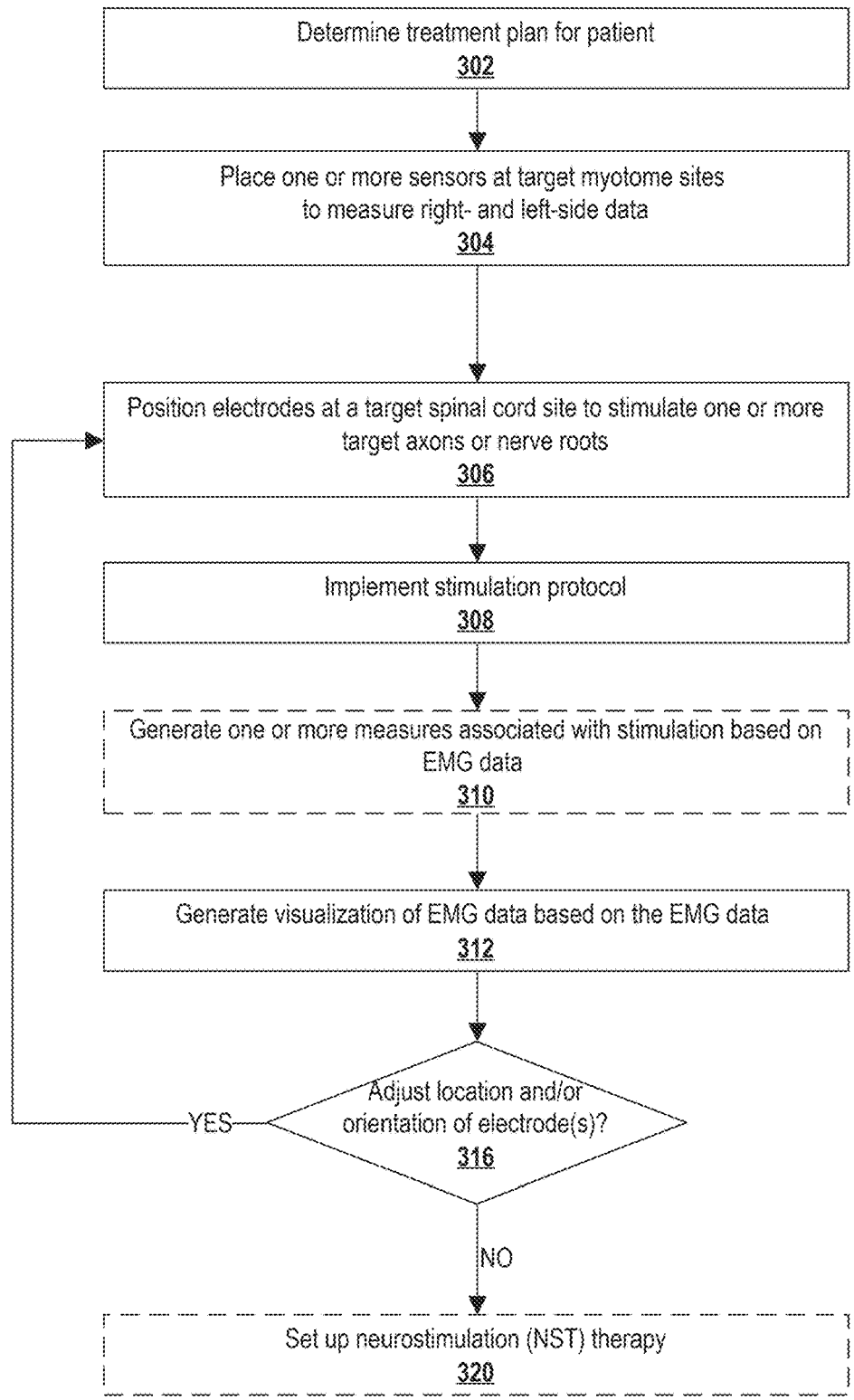
FIG. 3 is a flow diagram illustrating an exemplary embodiment of a method of using the apparatus of FIGS. 1A and 1B for electrode placement.

Referring now to FIG. 3, FIG. 3 is a flow diagram illustrating an exemplary embodiment of a method 300 of using apparatus 100 for optimizing electrode placement. At step 302, method 300 includes determining a treatment plan for a patient. As a nonlimiting example, a practitioner may determine a target location for one or more electrodes 122 based on a diagnosis of a patient and/or a region at which the patient experiences pain. At step 304, method 300 includes placing one or more sensors 132, such as, without limitation, one or more EMG sensors, at one or more target myotome sites to measure LS and RS data, such as, without limitation, EMG data. In one or more embodiments, an equal number of EMG sensors may be placed on the LS and the RS of a patient's body at one or more corresponding myotomes. As a nonlimiting example, 8 EMG sensors may be placed on the patient, with 4 EMG sensors placed on the LS and 4 EMG sensors placed on the RS. As another nonlimiting example, 16 EMG sensors may be placed on the patient, with 8 EMG sensors placed on the LS and 8 EMG sensors placed on the RS. In one or more embodiments, one or more dense electrode arrays may be used to collect EMG data such that greater than 8 EMG sensors may be positioned on each side of a patient's body. In one or more embodiments, the quality of signal from each of the EMG sensors may be tested and validated. As a nonlimiting example, one or more EMG sensors may optionally be reattached, re-adhered, and/or or repositioned if the quality of signal is determined to be below a predefined threshold.

With continued reference to FIG. 3, at step 306, method 300 includes positioning one or more electrodes 122 at a target spinal cord site to stimulate one or more target axons or nerve roots. In one or more embodiments, a fluoroscope may be used to guide one or more electrodes 122 to an initial position for stimulation. For the purposes of this disclosure, a fluoroscope is an imaging device that provides real-time, continuous X-ray images of one or more internal structures of the body. The medical imaging technique involving a use of fluoroscope is accordingly termed fluoroscopy. A fluoroscope functions by sending X-rays through the body and capturing one or more resulting images on a fluorescent screen or digital detector. Fluoroscopes are often used in procedures requiring live imaging, such as catheter insertions, orthopedic surgeries, and gastrointestinal tract evaluations, among others, allowing physicians to monitor the movement of an internal organ and/or guide an instrument during a medical intervention.

With continued reference to FIG. 3, at step 308, method 300 further includes implementing a stimulation protocol, consistent with details described above. In one or more embodiments, implementing a stimulation protocol may include cycling through a predetermined sequence of stimulation parameters and electrode pairs. As a nonlimiting example, a first electrode pair (e.g., an electrode pair at a rostral position on an electrode lead) may be activated, and stimulation device 120 may cycle through a predetermined sequence of electrode parameters. Once all stimulation parameters have been cycled through for the first electrode pair, a subsequent (second) electrode pair on the electrode lead may be activated, and stimulation device 120 may begin cycling through the same predetermined sequence as the first electrode pair. In one or more embodiments, this process may be repeated until all electrode pairs have cycled through the stimulation parameters. In one or more embodiments, the values of stimulation parameters may be held constant in general and only allowed to change one at a time. Accordingly, method 300 may include sequentially cycling through all electrode pairs using a first stimulation parameter before moving on to a second stimulation parameter. In one or more embodiments, stimulation device 120 may stop cycling through stimulation parameters and/or electrode pairs when a desired myotome activation is achieved. In one or more embodiments, stimulation device 120 may continue cycling through stimulation parameters and/or electrode pairs, even if a sufficient level of myotome activation has already been achieved, such that all possible configurations for stimulation parameters and electrode pairs are tested.

With continued reference to FIG. 3, in one or more embodiments, at step 310, method 300 may optionally include generating one or more measures associated with stimulation based on EMG data and/or an analysis thereof, consistent with details described above. In one or more embodiments, an activation ratio, a symmetrical activation measure, and/or an activation efficiency measure for each electrode pair may be generated. In one or more embodiments, an activation ratio, a symmetrical activation measure, and/or an activation efficiency measure may be determined for each muscle or myotome. In one or more embodiments, measurements corresponding to myotomes on the LS of the body and measurements corresponding to myotomes on the RS of the body may be aggregated respectively. Accordingly, an activation ratio, a symmetrical activation measure, and/or an activation efficiency measure may be generated based on such aggregated data. In one or more embodiments, an activation ratio, a symmetrical activation measure, and/or an activation efficiency measure for each electrode pair may be directly displayed to a practitioner, such as a physician. In one or more embodiments, an activation ratio, a symmetrical activation measure, and/or an activation efficiency measure may be used to generate a visual representation of the measurements, such that a practitioner may easily and efficiently interpret the data.

With continued reference to FIG. 3, at step 312, method 300 further includes generating a visualization of the EMG data based on the EMG data and/or the analysis thereof. In one or more embodiments, a visual representation of a symmetrical activation measure and/or an activation efficiency measure may be displayed to a practitioner. In one or more embodiments, EMG response data may be overlayed on an image collected using another imaging device or modality, such as, without limitation, magnetic resonance imaging (MRI) and/or fluoroscopy, consistent with details described above. In one or more embodiments, a visual representation of the FML of a spine may be generated for and/or displayed to a practitioner.

With continued reference to FIG. 3, at step 316, method 300 further includes deciding whether the location and/or orientation of one or more electrodes 122 should be adjusted. If the location and/or orientation of one or more electrodes 122 should be adjusted according to the EMG data and/or analysis (YES), then step 306 is repeated, and the one or more electrodes 122 may be repositioned based on the EMG data. As a nonlimiting example, a practitioner may aim to achieve an equal, bilateral activation of both the left-side and the right-side myotomes of a patient, but the visual representation of the EMG data may indicate that only the left-side myotomes are being strongly activated. In this nonlimiting example, the FML may be located further to the right relative to the current placement of the one or more electrodes 122, and the one or more electrodes 122 should be moved further toward the right side of the patient to achieve a desired activation. Once the position of the one or more electrodes 122 is updated, steps 306-316 of method 300 may be repeated until the EMG data indicate a desired pattern of myotome activation.

With continued reference to FIG. 3, once a placement over the target site is achieved (i.e., a response of NO is achieved at step 316), method 300 may optionally include, at step 320, setting up a neurostimulation therapy (NST), consistent with details described above.

Figure 4:
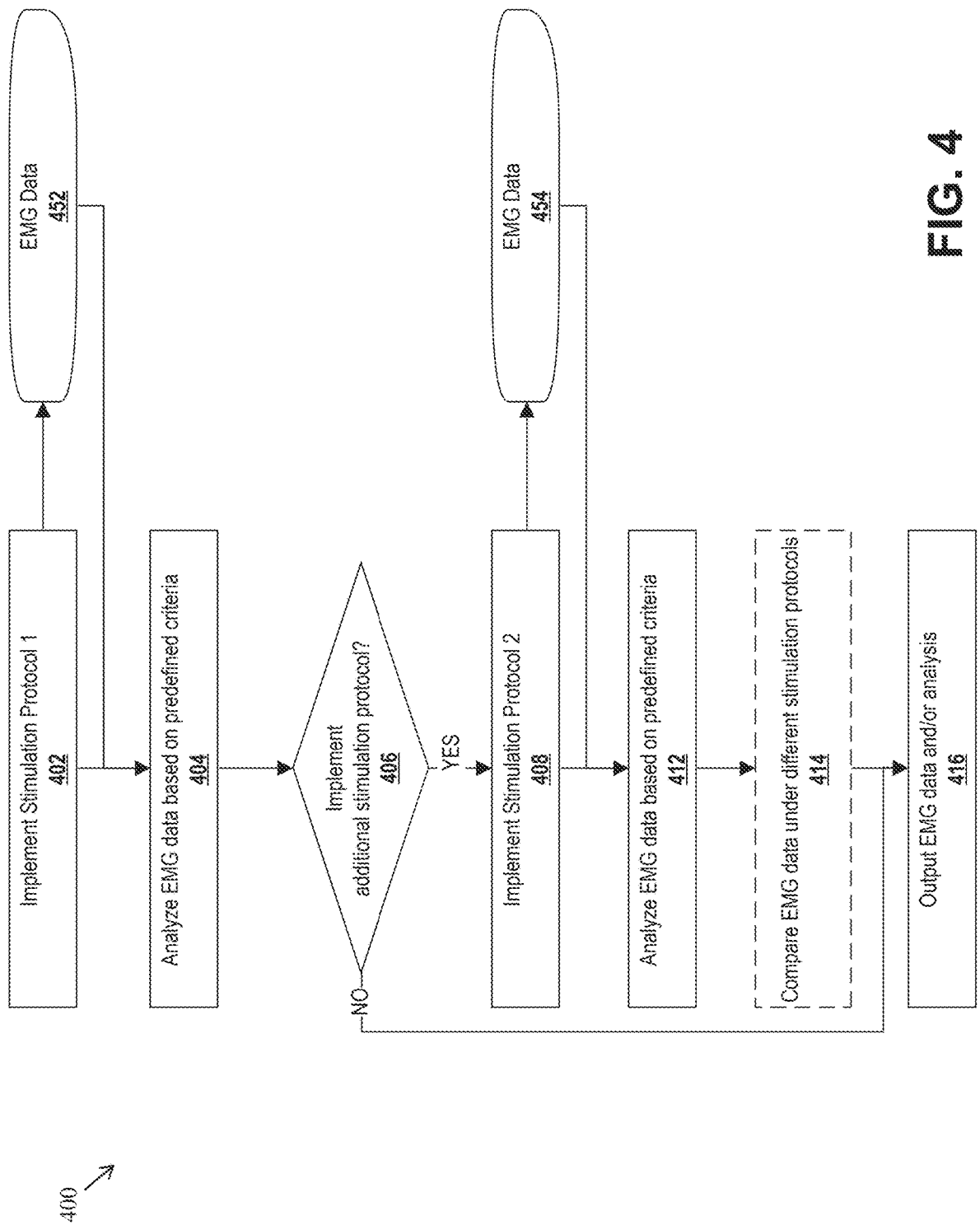
FIG. 4 is a flow diagram illustrating another exemplary embodiment of a method of using the apparatus of FIGS. 1A and 1B for electrode placement.

Referring now to FIG. 4, FIG. 4 includes an exemplary embodiment of a flow diagram illustrating a method 400 that may be used during electrode placement. While method 400 is described with reference to apparatus 100, it should be noted that this method may be performed using any other suitable SCS positioning systems, as recognized by a person of ordinary skill in the art, upon reviewing the entirety of this disclosure. At step 402, stimulation method 400 includes implementing a first stimulation protocol. In one or more embodiments, the first stimulation protocol may include a set sequence of stimulation parameters generated by stimulation device 120, consistent with details described above. As a nonlimiting example, implementing the first stimulation protocol may include incrementally adjusting each stimulation parameter, such as, without limitation, current amplitude, frequency, pulse width, repetition rate, and/or duty cycle, among others, consistent with details described elsewhere in this disclosure. In one or more embodiments, each stimulation parameter may be ramped up in isolation. In one or more embodiments, one or more stimulation parameters may be ramped up simultaneously. In one or more embodiments, one or more stimulation parameters may be ramped up linearly. In one or more embodiments, the one or more stimulation parameters may be ramped up non-linearly and/or according to a predetermined function, such as, without limitation, an exponential function, a logarithmic function, a sigmoid function, a quadratic function, a polynomial function, or the like. As the first stimulation protocol is implemented, EMG data 452 indicative of myotome activation is measured via sensors 132. EMG data were elaborated only as a proof of concept, as the invention described herein may be expanded to any type of physiological data and/or biosignals without limitation.

With continued reference to FIG. 4, at step 404, method 400 further includes analyzing EMG data 452 collected by one or more sensors 132 based on a predefined set of criteria. As a nonlimiting example, EMG data 452 may be analyzed for an activation threshold of each muscle or myotome (e.g., an activation efficiency measure), a level of symmetry between the one or more left-side and right-side muscles or myotomes (e.g., a symmetry activation measure), and/or a level of correlation between EMG signal corresponding to different myotomes, among others. As another nonlimiting example, analyzing EMG data 452 may include filtering the EMG data 452 data to optimize its quality and extracting the optimized EMG data 452. Accordingly, analyzing EMG data 452 may further include calculating one or more metrics as a function of the optimized EMG data 452 and identifying the target location as a function of the one or more metrics, consistent with details described above.

With continued reference to FIG. 4, at step 406, method 400 further includes conducting an assessment regarding whether an additional stimulation protocol should be implemented. In one or more embodiments, such an assessment may be done by a computing device, as described above. In some cases, this assessment may be performed automatically based on one or more predefined criteria. Additionally, and/or alternatively, at least a portion of such assessment may be performed manually by a practitioner, e.g., by viewing stimulation data and/or EMG data. If it is determined that no additional stimulation protocol should be implemented (NO), the EMG data and/or EMG analysis is output, for example and without limitation, to display 116/216 of computing device 110/210, to an external device 250, to a server, and/or the like. If it is determined that no additional stimulation protocol should be implemented (YES), a second stimulation protocol may be implemented accordingly. The first stimulation protocol may fail to generate desirable EMG response data due to reasons including but not limited to a lack of EMG response, a low response efficiency, and/or poor data quality, among others. Accordingly, for such cases, method 400 may further include implementing a second stimulation protocol at step 408.

With continued reference to FIG. 4, as the second stimulation protocol is implemented, new EMG data 454 are collected. Accordingly, at step 412, method 400 may further include analyzing new EMG data 454 based on the predefined criteria, as described above. In one or more embodiments, method 400 may optionally include comparing the EMG data under different stimulation protocols at step 414. As a nonlimiting example, EMG data 452 resulting from the first stimulation protocol may be compared to EMG data 454 resulting from the second stimulation protocol. Lastly, at step 416, EMG data 452, 454 and/or analysis from first stimulation protocol and/or second stimulation protocol may be output, for example and without limitation, to a display 116/216 of computing device 110/210, to an external device 250, to a server, or the like.

Figure 5B:
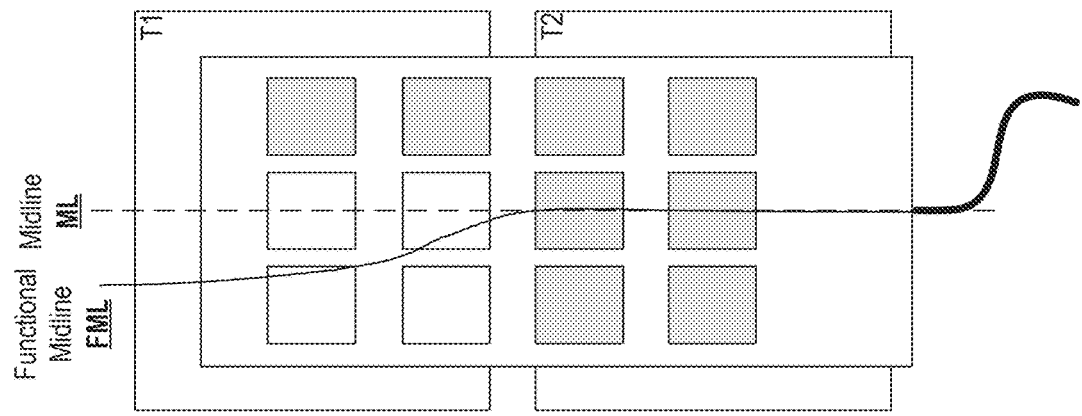
FIGS. 5A-B are schematic diagrams illustrating exemplary embodiments of placements of implantable leads relative to a functional midline (FML) or a vertebral midline (ML)
Figure 5A:
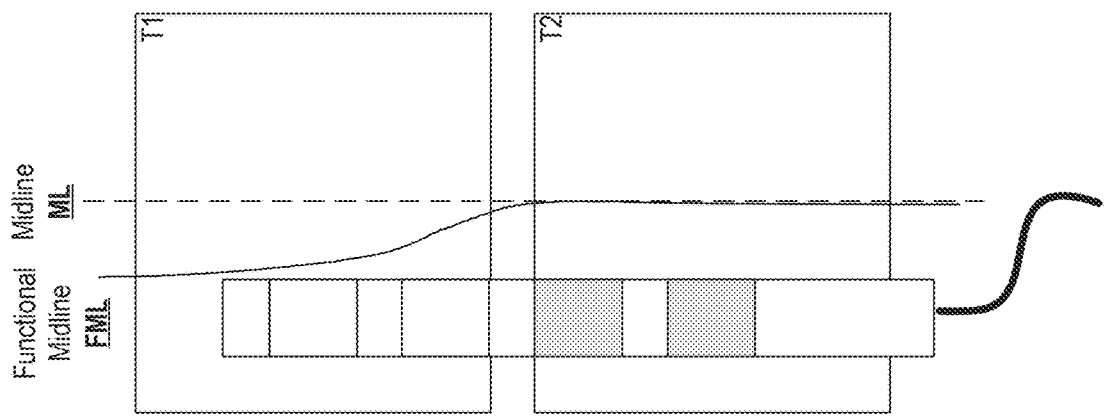

Referring now to FIGS. 5A-B, FIGS. 5A-B are exemplary embodiments of schematic diagrams 500*a-b* illustrating placement of an implantable electrode lead relative to a spinal cord, wherein the electrode lead includes a plurality of electrodes 122. Specifically, FIGS. 5A-B show the first thoracic vertebra (T1), the second thoracic vertebra (T2), the ML, and the FML. As shown, the ML lies along the center or middle (i.e., the structural center) of a vertebral column (i.e., a spine), whereas the FML may stray from the structural center of the spine. The FML corresponds to the nerve activity rather than solely the structure of the spine (e.g., structure of the vertebral column or spinal canal), consistent with details described above. Since a spinal cord stimulation relies on modulating nerve activity, determining the proximity relative to FML for positioning electrodes 122 may result in a higher chance of therapeutic success, for example and without limitation, by improving an alignment between a practitioner's intended neural target and the pain experienced by a patient.

With continued reference to FIGS. 5A-B, as shown in FIG. 5A, schematic diagram 500*a* illustrates a percutaneous cylindrical electrode lead implanted left to the ML. Percutaneous cylindrical electrode leads may be implanted using an epidural needle without the need for surgery. Therefore, implantation of a percutaneous cylindrical electrode may in some cases be performed by a pain physician rather than a surgeon. An improved accuracy in placing or implanting one or more electrodes 122 via a non-surgical procedure may greatly improve the accessibility of SCS therapy. As a nonlimiting example, a percutaneous cylindrical electrode lead may include a plurality of electrode contacts disposed linearly along the length of the electrode lead. Any two electrodes 122 on an electrode lead may constitute an electrode pair, with one electrode 122 functioning as a stimulation electrode and the other electrode 122 functioning as a reference electrode, consistent with details described above in this disclosure.

With continued reference to FIGS. 5A-B, in some cases, a practitioner may choose a target location to be directly over the FML of T1. Such configuration may be adopted for purposes including without limitation an equal activation of left-side myotomes and right-side myotomes, etc. The electrode pair shown as white squares in FIGS. 5A-B may yield successful stimulation. Stimulation using such an electrode pair may result in the highest probability of symmetrical activation of myotomes innervated by nerve roots originating from T1, whereas stimulation of other electrode pairs may result in a stronger activation of myotomes on the LS of the body with respect to the RS of the body. Similarly, target locations for other levels of the spinal canal, e.g., one or more of T2-T12, may be identified.

With continued reference to FIGS. 5A-B, as shown in FIG. 5B, schematic diagram 500b illustrates an example of a paddle electrode lead centered over the ML at T1 and T2. A paddle electrode lead includes electrode contacts in a two-dimensional array, which may allow for a wider coverage of tissue around a spinal cord and therefore lead to a higher probability of positioning electrodes 122 over a target area. However, in some cases, while a paddle electrode lead may enable larger coverage of the target area, a patient may need to undergo surgery for such an implantation. As a nonlimiting example, in the case where a practitioner chooses a target location to be directly over the FML of T1, electrode pairs chosen from the four electrodes from the top left corner of the paddle electrode lead, shown as white squares, may result in the highest probability of symmetrical activation of myotomes innervated by nerve roots originating from T1.

Data Processing and Visualization

Figure 6A:
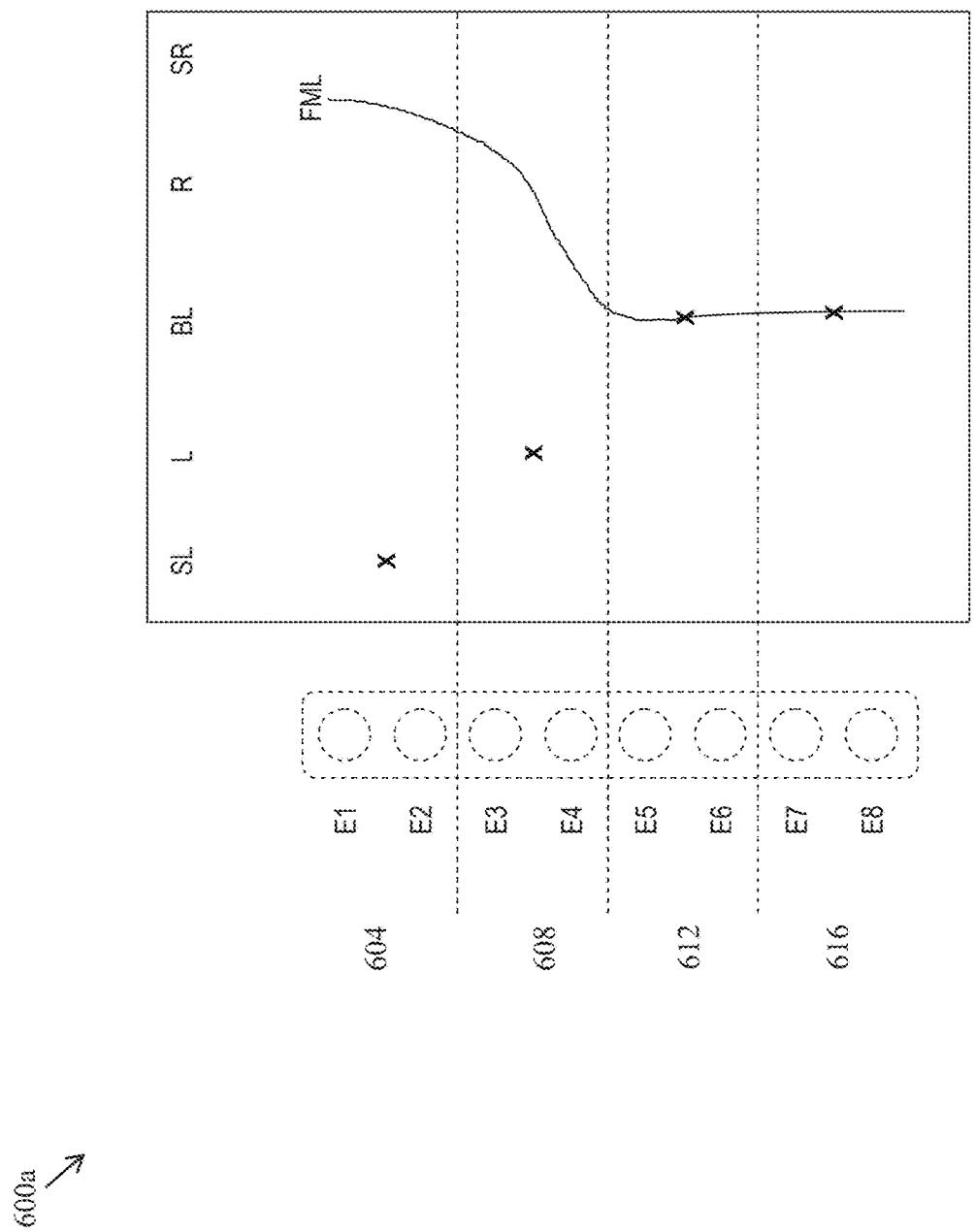
FIGS. 6A-C are schematic diagrams illustrating nonlimiting examples of a visual representation of processed EMG data.
Figure 6B:
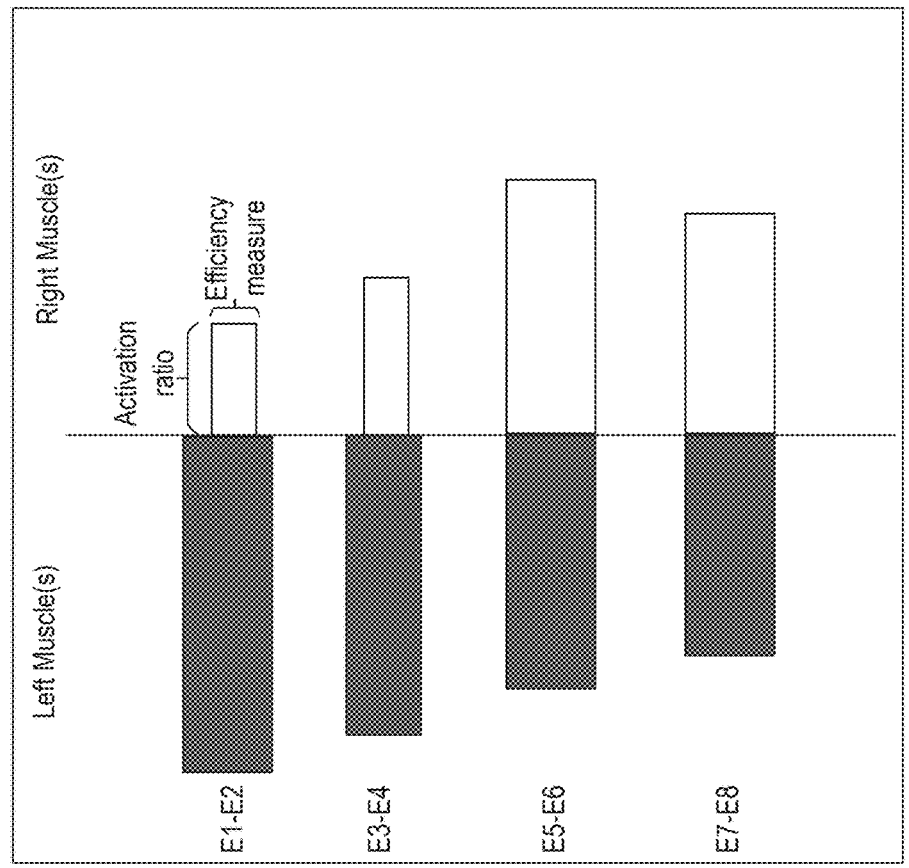
Figure 6C:
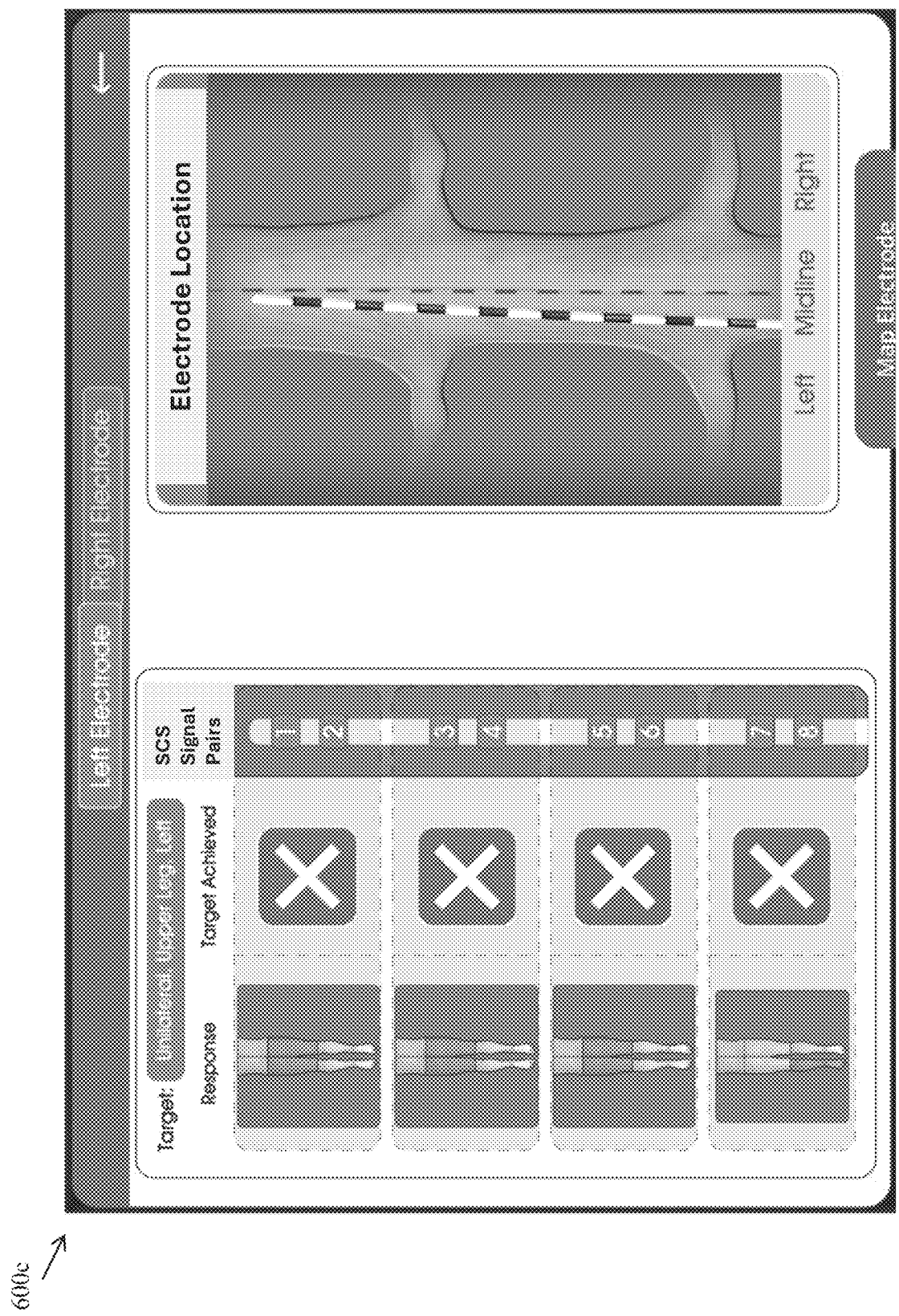

Referring now to FIGS. 6A-C, FIGS. 6A-C show exemplary embodiments of visual representations 600a-c based on processed EMG data. As shown in FIG. 6A, an estimation of FML based on analyzed EMG data is overlayed with a diagram of a percutaneous cylindrical electrode. Specifically, in a non-limiting example, the percutaneous cylindrical electrode includes 8 electrode contacts, E1, E2, E3, E4, E5, E6, E7, and E8. EMG responses are grouped into strong-left responses (SL), left responses (L), bilateral responses (BL), right responses (R), and strong-right response (SR), as shown along the horizontal axis at the top of FIG. 6A. Activation of electrode pair E1 and E2 results in a strong-left response (denoted with an X under SL), activation of electrode pair E3 and E4 results in a left response (denoted with an X under L), activation of electrode pair E5 and E6 results in a bilateral response (denoted with an X under BL), and activation of electrode pair E7 and E8 results in a bilateral response (denoted with an X under BL). An estimation of FML based on such results is overlaid with both the diagram of the electrode and the EMG responses described above. In one embodiment, the electrode contacts are grouped in pairs 604, 608, 612, and 616. It is worth noting that the pairs of electrode contacts 604, 608, 612, and 616 described above are exemplary, as any two of electrodes E1-E8 may be used as an electrode pair in order to perform one or more functions of the invention described herein. As a nonlimiting example, E1 and E2 may be used as electrode contact pair 604 in a first use case, whereas E1 and E4 may be used as another electrode pair instead in a second use case different from the first use case. As another nonlimiting example, a wide variety of permutations between a plurality of electrodes may be used on a rotating basis in order to identify and select one or more suitable configurations. As a non-limiting example, a set of eight electrodes E1-E8, as described above, may provide a set of 28 possible combinations for electrode pairs. It is also worth noting that linear arrangement of eight electrodes E1-E8 is also exemplary, as a plurality of electrodes E1-E8 may be deployed following any type of topology, such as without limitation a square lattice, rectangular lattice, an oblique lattice, a hexagonal lattice, and/or the like, that is deemed suitable by a person of ordinary skill in the art, upon reviewing the entirety of this disclosure. It is also noting that the two electrodes with an electrode pair may each be designated as an active electrode and a reference electrode, respectively, consistent with details described elsewhere in this disclosure, and such designation may be arbitrary and depend on the context of use. As a nonlimiting example, within an electrode pair E1 and E2, in some cases, E1 may be used as an active electrode, whereas E2 may be designated as a reference electrode; alternatively, in some other cases, E2 may be used as an active electrode, whereas E1 may be designated as a reference electrode.

With continued reference to FIGS. 6A-C, FIG. 6B includes a horizontal bar plot 600b generated based on the processed EMG data from FIG. 6A. For each electrode pair E1-E2, E3-E4, E5-E6, and E7-E8, an activation ratio and an activation efficiency measure are calculated based on EMG data from left-side and right-side muscles, respectively. The magnitude of an activation ratio may be represented using a bar length. In other words, a longer bar may represent a higher magnitude of activation ratio in a muscle or myotome in response to stimulation. The magnitude of an activation efficiency measure may be represented using a bar width. In other words, a wider (i.e., thicker) bar may represent a higher activation efficiency measure in a muscle or myotome in response to stimulation. Specifically, a higher efficiency measure may indicate that the muscle/myotome is activated at a lower threshold of stimulation, such as, without limitation, a lower current amplitude, etc. As shown in FIG. 6B, the left-side muscle(s) or myotome(s) shows higher activation ratios and activation efficiency measures in response to stimulations by electrode pair E1-E2 and electrode pair E3-E4, which may indicate that these electrode pairs may be positioned to the left of an FML. In contrast, the left-side and right-side muscle(s) or myotome(s) showed equal activation ratios and activation efficiency measures in response to stimulations by electrode pair E5-E6 and electrode pair E7-E8, which may indicate that these two electrode pairs may be positioned closer to or on top of an FML.

With continued reference to FIGS. 6A-C, FIG. 6C is a non-limiting example of a visual representation via user interface 600c illustrating target locations of a specific body region (e.g., unilateral, upper leg, left), SCS signal pairs (e.g., E1-E2, E3-E4, E5-E6, E7-E8), responses to stimulations made by the plurality of SCS electrode pairs, whether target location is achieved or not, and a map demonstrating electrode location with respect to left side and right side of a vertebral midline (ML) and/or a functional midline (FML). In some embodiments, immediate, real-time, or near real-time feedback via the visual representation may be provided to a physician to confirm whether response to stimulations at a target location is achieved based on inputs from one or more SCS signal pairs. In another embodiment, visual confirmation such as color change and/or error messages/alerts may indicate if a target is achieved. As a nonlimiting example, based on the response to the stimulations, a determination as to whether an active-reference electrode pair (e.g., E1-E2) is positioned on the left side, at the center, or on the right side with respect to the spinal cord may be made and visualized.

Figure 7A:
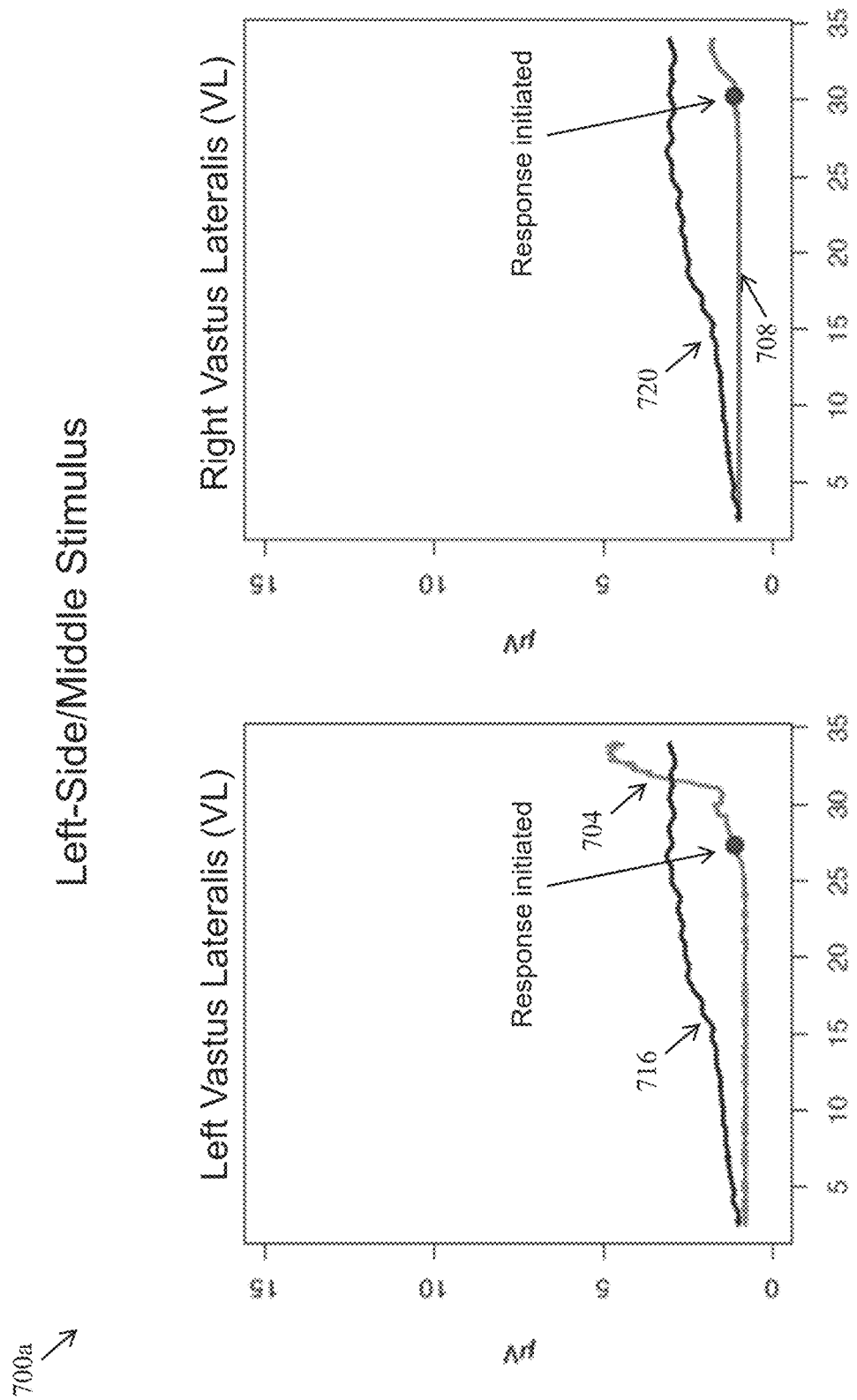
FIGS. 7A-D are exemplary results from an analysis of EMG data.

Referring now to FIGS. 7A-D, exemplary results 700a-d from an analysis of EMG data are illustrated. FIG. 7A shows EMG data from the Vastus Lateralis (VL; traces 704 and 708) and Rectus Abdominus (RA; traces 716 and 720) in response to a stimulation applied at a first location. The left panel shows an envelope of EMG response in microvolts (μV) of the left VL and RA over time, which is measured in seconds(s). The right panel shows an envelope EMG response in μV of the right VL and RA over time, which is measured in seconds(s). Traces 716 and 720 conceptually represent the amplitude of the stimulus as derived from the RA, which is a muscle in proximity to the stimulating electrodes, and record a time-dependent stimulus input due to an artifact caused by the EMG electrodes. As shown in FIG. 7A, the amplitude of the stimulus is incrementally increased over time. In response to stimulation applied at the first location, the left VL begins responding at approximately 27 seconds (see left panel), whereas the right VL begins responding at about 30 seconds (see right panel). The time in seconds is not measured relative to when the stimulation was turned on or off but instead calibrated to a larger temporal window of data extracted from experimental results containing both on and off periods for two different electrodes. In one or more embodiments, the amplitude of the current pulse and the time at which a response is induced may be recorded. The stimulus signal-to-noise ratio (SNR) versus the muscle activation signal-to-noise ratio (SNR) may be calculated (not shown). When a stimulus is applied at the first location, the left VL shows a larger muscle activation SNR than the right VL, which aligns with the response traces in the left and right panels. Both the left VL and the right VL respond when the stimulus SNR is approximately 3.0. These results demonstrate that the left VL may have a higher strength of activation (e.g., a higher activation ratio), whereas the left VL and the right VL have a similar activation efficiency ratio, which may indicate that the stimulation may be targeting a location to the left of an FML (left-side/middle).

Figure 7B:
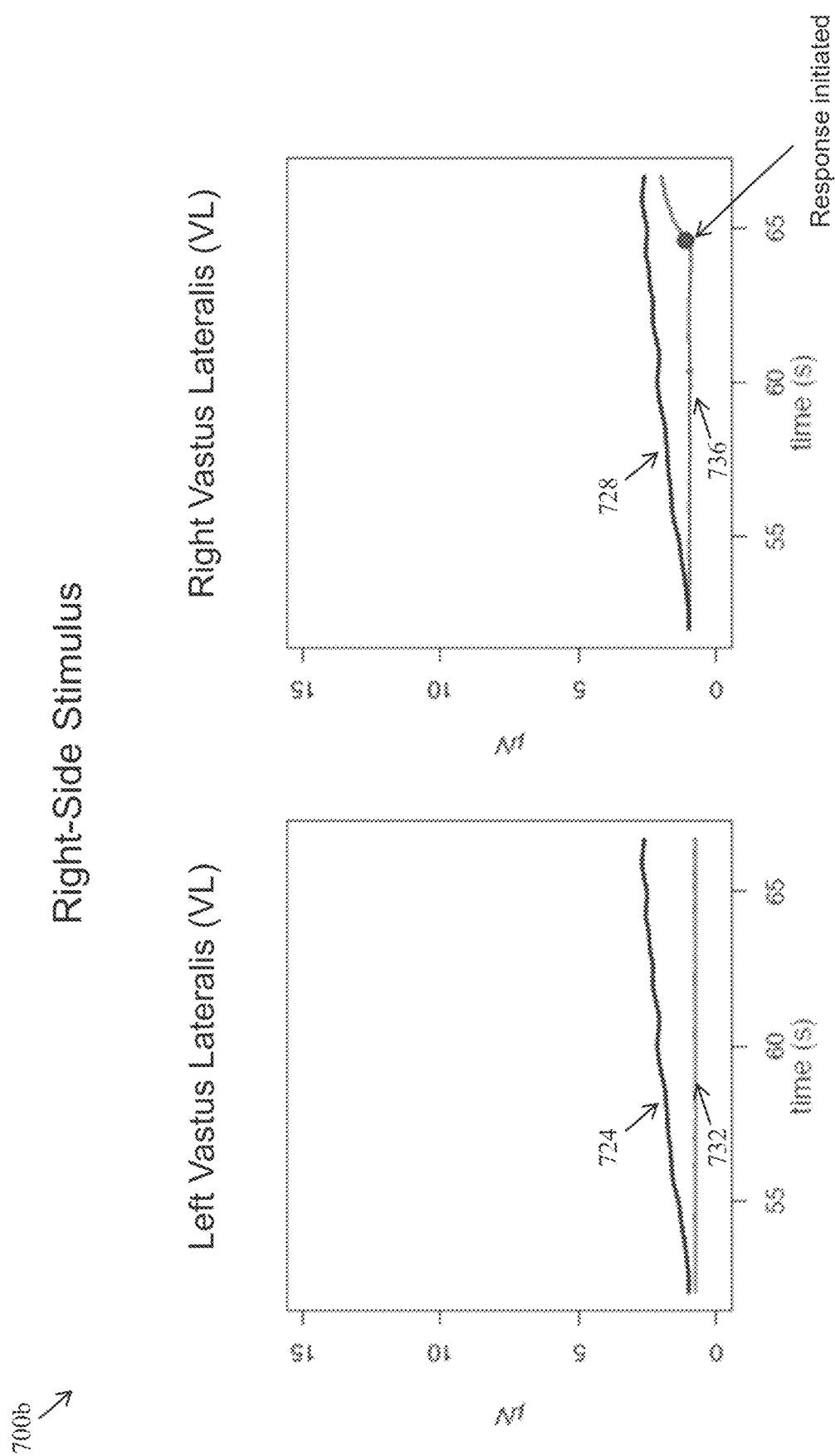
Figure 7C:
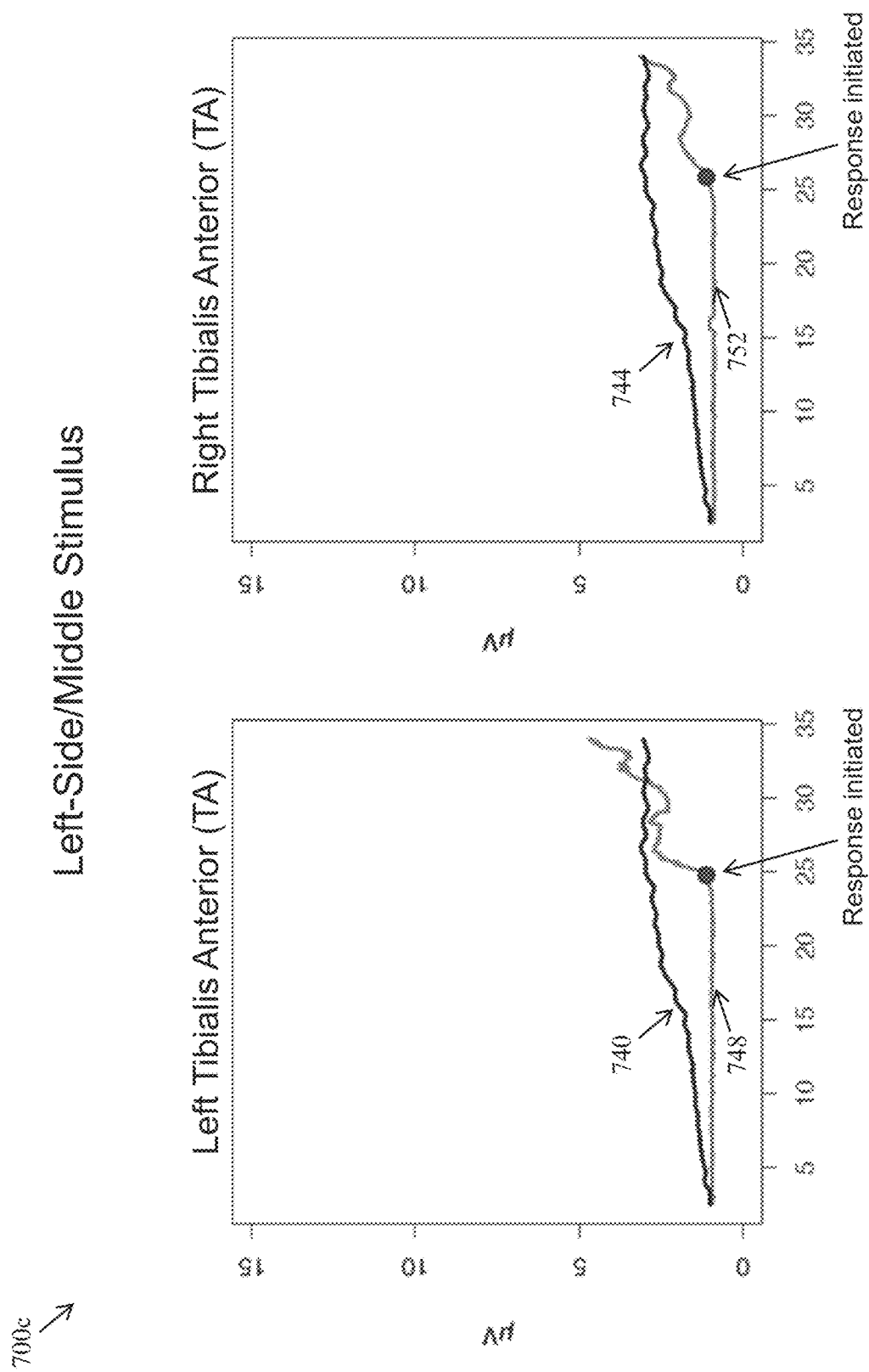
Figure 7D:
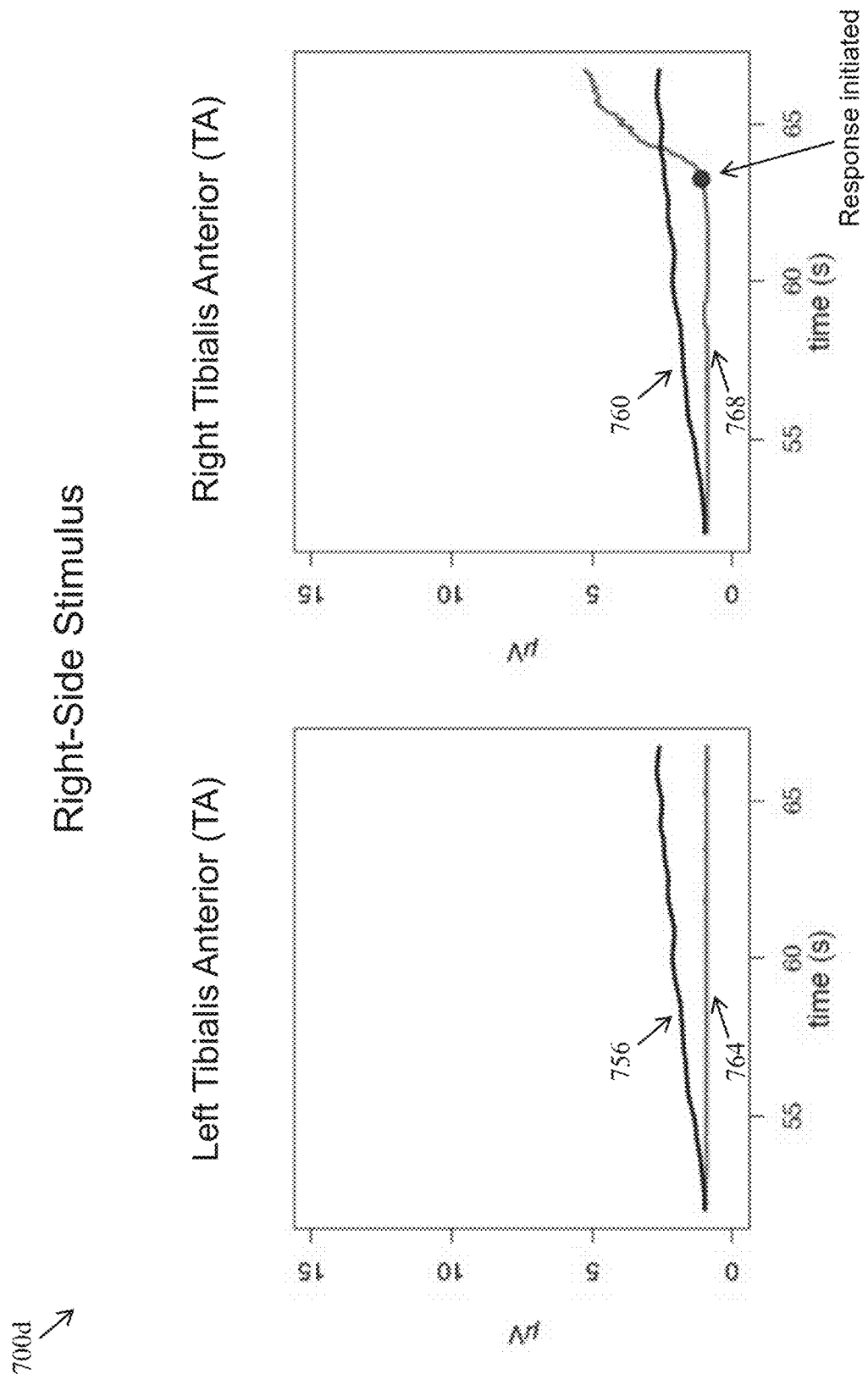

With continued reference to FIGS. 7A-D, FIG. 7B shows analyzed EMG data (traces 724, 728, 732 and 736) from the VL and RA in response to a stimulation applied to a second location, consistent with details described above pertaining to FIG. 7A. The left VL does not show a response, whereas the right VL shows a response at 65 seconds. The left VL SNR equals zero since no response occurred, whereas the right VL responds when the stimulus SNR is approximately 2.5 (not shown). These results indicate that the stimulation may be targeting a location to the right of an FML (right-side).

With continued reference to FIGS. 7A-D, FIG. 7C shows analyzed EMG data (traces 740, 744, 748 and 752) from the Tibialis Anterior (TA) and RA in response to a stimulation applied at a first location, consistent with details described above pertaining to FIGS. 7A-B. Traces 740 and 744 conceptually represent the amplitude of the stimulus as previously described. In response to stimulation applied at the first location, the left TA begins responding at approximately 25 seconds (see left panel), and the right TA begins responding at about 26 seconds (see right panel). The stimulus signal-to-noise ratio (SNR) versus the muscle activation signal-to-noise ratio (SNR) is determined accordingly (not shown). The left TA shows a larger SNR than the right TA. Therefore, the left TA has a higher strength of activation (e.g., a higher activation ratio) than the right TA. Both the left TA and the right TA show a response when the stimulus SNR is approximately 3.0. Therefore, both the left TA and the right TA respond to a similar stimulus amplitude (e.g., the left TA and the right TA have a similar activation efficiency). These results indicate that the stimulation may be targeting a location to the left of the FML (left-side/middle).

With continued reference to FIGS. 7A-D, FIG. 7D shows analyzed EMG data (traces 756, 760, 764, and 768) from the TA and RA in response to stimulation applied at the second location, consistent with details described above pertaining to FIGS. 7A-C. The left TA does not respond (left panel), whereas the right TA shows a response at about 63 seconds. The right TA shows a significantly larger SNR than the left TA (not shown). Additionally, the right TA response to stimulation on the right side of the spine has a higher SNR than the right TA response to stimulation on the left/middle of the spine. These results indicate that the stimulation may be targeting a location to the right of the functional midline.

Figure 8A:
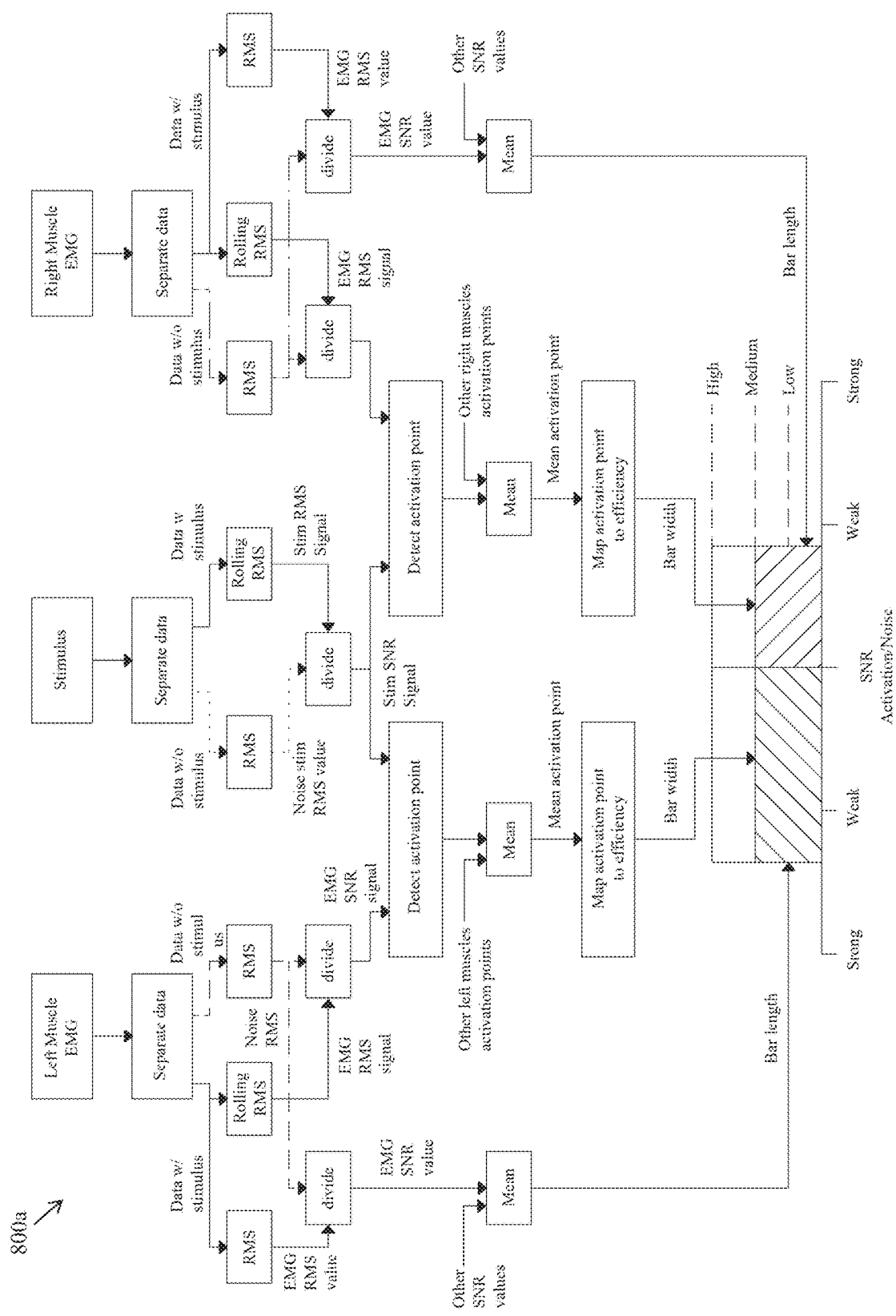
FIGS. 8A-C are flow diagrams illustrating exemplary embodiments of a method for processing and analyzing EMG data to generate a visual representation therefrom.
Figure 8B:
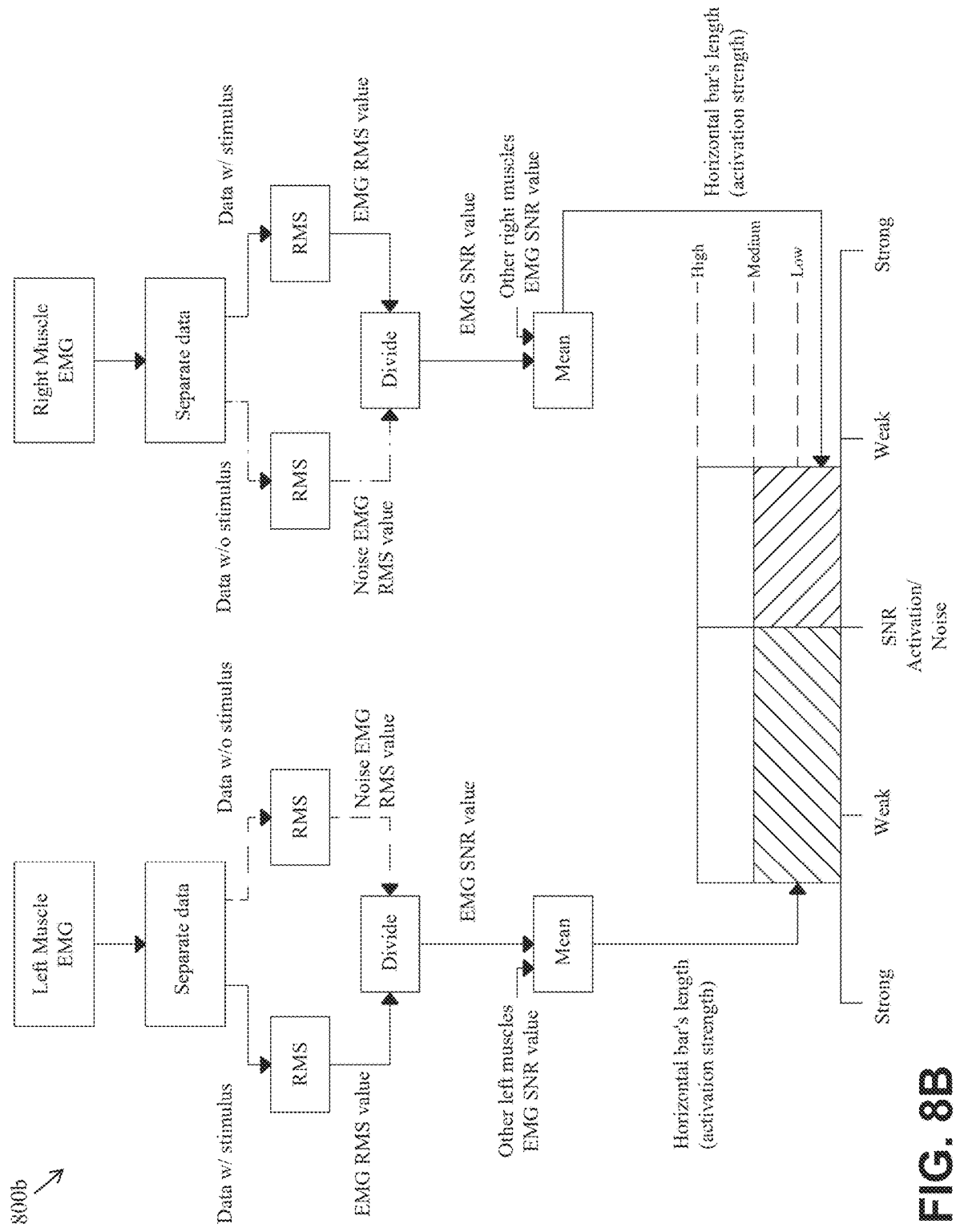
Figure 8C:
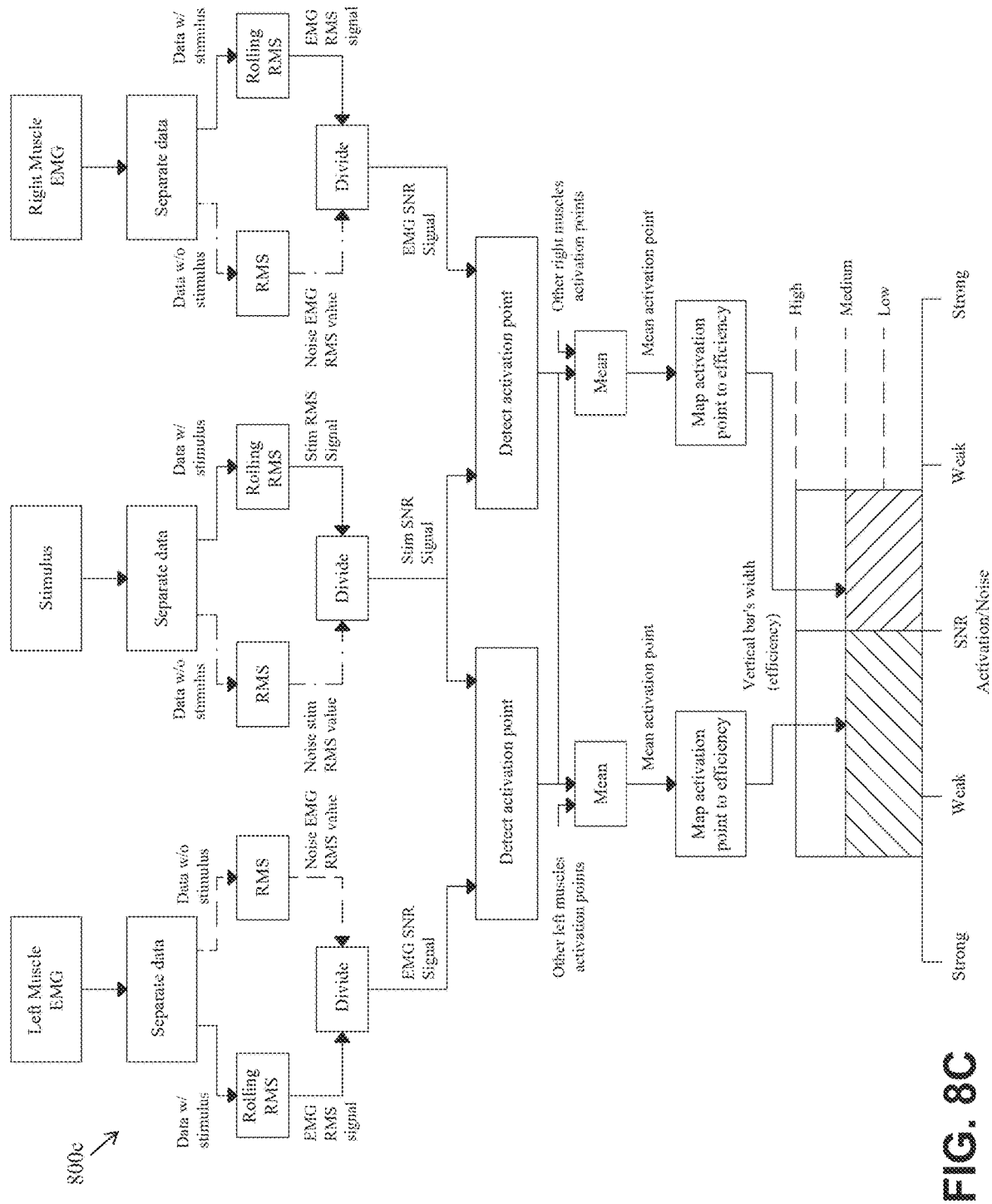

Referring now to FIGS. 8A-C, FIGS. 8A-C include exemplary embodiments of flow diagrams 800a-c illustrating a method for processing and analyzing EMG data to generate a visual representation therefrom. FIG. 8A includes a flow diagram of an exemplary algorithm for determining a strength (e.g., activation ratio) and efficiency of muscle activation. Terms used in this diagram include:

RMS: the square root of the mean of the squared values of a signal.

SNR: signal to noise ratio, which is calculated by dividing the RMS value during stimulation by the RMS value without stimulation.

EMG RMS value: the RMS value of the EMG signal while the stimulus is active. The EMG RMS value is a scalar.

Noise EMG RMS value/Noise RMS: the RMS value of the EMG signal while the stimulus is inactive. The Noise EMG RMS value is a scalar.

Noise stimulus RMS value: the RMS value of the stimulus signal while the stimulus is inactive. The noise stimulus RMS value is a scalar.

EMG RMS signal: the vector obtained by taking the RMS value for each position of a rolling window through the EMG signal. The EMG RMS signal is a vector.

Stimulus (Stim) RMS signal: the vector obtained by taking the RMS value for each position of a rolling window through the stimulus signal. The stimulus RMS signal is a vector.

EMG SNR value: the EMG RMS value divided by noise EMG RMS value. Specifically, it is equal to the RMS value of the EMG signal while the stimulus is active divided by the RMS value of the EMG signal while the stimulus is inactive. The EMG SNR value is a scalar.

EMG SNR signal: the vector obtained by dividing the EMG RMS signal by the noise EMG RMS value. In other words, it is the vector obtained dividing the RMS for each position of the window by the RMS obtained when the stimulus is inactive. The EMG SNR signal is a vector.

Stimulus SNR signal: the vector obtained by dividing the stimulus RMS signal by the noise stimulus RMS value. Specifically, it is the vector obtained by dividing RMS for each position of the window in the stimulus signal by the RMS obtained in the stimulus signal when the stimulus is inactive. The stimulus SNR signal is a vector.

Activation point: under the experimental setting with a stimulus increasing its amplitude, the specific value for a stimulus SNR signal, during a stimulation phase, when the EMG SNR signal passes a predetermined SNR threshold for the first time. In one or more embodiments, the predetermined SNR threshold may be set to 1.1. When the activation point is low, the efficiency of activation is high, and vice versa. In order to estimate an activation efficiency, the activation point may be scaled accordingly.

With continued reference to FIGS. 8A-C, in one or more embodiments, the SNR threshold may be set as 1.1 for weak muscle activation detection (e.g., weak SNR threshold), and the SNR threshold may be set as 1.5 for strong muscle activation detection (e.g., strong SNR threshold). In one or more embodiments, when the total SNR value is between 1.1 and 1.5, the muscle activation may be considered a weak muscle activation. In one or more embodiments, when the total SNR value is greater than 1.5, the muscle activation may be considered a strong muscle activation. In one or more embodiments, an activation efficiency may be characterized as low, medium, or high, depending on the exact activation point value. If an activation point is below a first activation threshold (e.g., 2), the activation efficiency may be considered high. If an activation point is above a second threshold (e.g., 3), the activation efficiency may be considered low. If an activation point falls between the first activation threshold and the second activation threshold (e.g., between 2 and 3), the activation efficiency may be considered medium.

With continued reference to FIGS. 8A-C, FIG. 8B includes a flow diagram of an exemplary algorithm for determining the strength of muscle activation. In one or more embodiments, to obtain the strength of the muscle activation (e.g., the activation ratio), the following steps may be used: (1) separate the EMG data in two parts, one for data when the stimulus is ON and the other for data when the stimulus is OFF; (2) determine the RMS value for these two parts; (3) determine the SNR ratio by dividing RMS value for the ON time by the RMS value for the OFF time; and (4) take the mean of SNR for the most important muscle from the side under analysis.

With continued reference to FIGS. 8A-C, FIG. 8C includes a flow diagram of an exemplary algorithm for determining the efficiency of muscle activation. In one or more embodiments, to obtain an activation efficiency, the following steps may be used: (1) separate the EMG data in two parts, one for data when the stimulus is ON and another for data when the stimulus is OFF; (2) get the RMS signal for the EMG and the stimulus while the stimulus is ON; (3) get the RMS value for the EMG and the stimulus when the stimulus is OFF (noise); (4) get the SNR signal for the stimulus and the EMG by dividing the RMS signals by the corresponding noise RMS value; (5) detect activation points by searching the SNR for the stimulus when the EMG SNR signal passes the weak SNR threshold for the first time; (6) take the mean of activation points for the selected muscles; and (7) map the activation point to an estimated efficiency.

With continued reference to FIGS. 8A-C, additionally and/or alternatively, several algorithms may be used, either in singularity or in combination, for performing one or more functions of apparatus 100. In some cases, an algorithm for spinal cord stimulator impedance check may be implemented. Such an algorithm measures the impedance between one or more electrodes 122 and the spinal cord and ensures proper contact between a spinal cord stimulator (SCS) and the spinal cord. This algorithm may be critical for effective stimulation and patient safety. Specifically, this algorithm may be configured to verify SCS electrode positioning, prevent ineffective stimulation due to poor impedance, and/or provide real-time feedback during electrode placement. Input parameters for this algorithm may include electrode configuration with specific SCS electrode setup. Input parameters for this algorithm may further include measured impedance values describing the impedance between each electrode 122 and the spinal cord. Input parameters for this algorithm may further include reference impedance range, which includes an acceptable impedance range for effective stimulation. Input parameters for this algorithm may further include signal quality metrics, which include indicators such as noise levels affecting impedance measurements.

With continued reference to FIGS. 8A-C, an algorithm for spinal cord stimulator impedance check may be implemented using certain quantitative methodology. As a non-limiting example, this algorithm may be configured to measure impedance (R) using Ohm's law and calculate the impedance (R) by applying a known current (I) and measuring the resulting voltage (V). The algorithm may then compare the measured impedance to a reference range to determine contact quality. An impedance that is too high may indicate poor contact, whereas an impedance that is too low indicates potential short circuit. The algorithm may be configured to output an impedance status, e.g., a pass/fail status or the like, for each electrode 122. The algorithm may be configured to further extract and output impedance values. The algorithm may be configured to further output error alert(s), if any, such as, without limitation, one or more notifications for out-of-range impedance.

With continued reference to FIGS. 8A-C, an algorithm for spinal cord stimulator impedance check may be implemented using one or more validation strategies. Suitable validation strategies for this algorithm may include, without limitation, bench testing using bench models, intraoperative testing during SCS implantation, postoperative follow-up to monitor long-term reliability, among others.

With continued reference to FIGS. 8A-C, an algorithm for spinal cord stimulator impedance check may be implemented using one or more error-handling strategies. Suitable error-handling strategies for this algorithm may include identifying when an impedance is outside the acceptable range, detecting inconsistencies in signal quality metrics, and/or monitoring for rapid fluctuations in impedance values (i.e., a detection strategy). Suitable error-handling strategies for this algorithm may further include generating one or more immediate visual/auditory alerts to a practitioner and/or highlighting one or more affected electrodes 122 using a graphical user interface (i.e., a notification strategy). Suitable error-handling strategies for this algorithm may further include recommending repositioning one or more electrodes 122 if impedance is too high, suggesting rechecking connections if impedance is too low, and/or offering guidance on checking for possible short circuits or other hardware issues (i.e., a strategy for suggested actions). Suitable error-handling strategies for this algorithm may further include automatically logging an error event for future analysis and/or storing details about the error event including without limitation time, electrode(s) 122 involved, impedance value, among others (i.e., a logging strategy).

With continued reference to FIGS. 8A-C, an algorithm for spinal cord stimulator impedance check may be configured to display one or more real-time impedance values using a display and/or graphical user interface. In some cases, these real-time impedance values may be color-coded based on their corresponding numerical values or ranges. Similarly, this algorithm may be configured to implement an alert system by generating visual/auditory alerts for out-of-range impedance to be displayed using a display and/or graphical user interface.

With continued reference to FIGS. 8A-C, in some cases, an algorithm for SS-SCM stimulator check may be implemented. Such an algorithm measures return current during stimulation to verify SS-SCM stimulator functionality, ensure that an SS-SCM stimulator is functioning properly, and prevent malfunction by ensuring correct current delivery. Specifically, this algorithm may utilize direct measurement techniques using current sensors. As nonlimiting examples, these current sensors may include without limitation current sensing resistors (shunt resistors) and hall effect sensors, among others, that are configured to verify the accuracy and functionality of an SS-SCM stimulator. An algorithm for SS-SCM stimulator check may be configured to confirm that an SS-SCM stimulator is delivering the correct amount of current and that the return current matches expected values, detect any discrepancies between delivered and returned current to prevent malfunctions, and/or provide immediate feedback on a stimulator's performance using reliable and non-intrusive methods of measurement. Input parameters for this algorithm may include a delivered current, i.e., the electrical current delivered by an SS-SCM stimulator to a spinal cord. Input parameters for this algorithm may further include a measured return current, i.e., the current measured, using one or more current sensors, as it returns from an electrode 122 after stimulation. Input parameters for this algorithm may further include an expected return current range, i.e., the acceptable range for the return current derived based on the delivered current.

With continued reference to FIGS. 8A-C, an algorithm for SS-SCM stimulator check may be implemented using certain quantitative methodology. As a nonlimiting example, one or more current sensing resistors (shunt resistors) may be implemented. Specifically, a small resistor may be placed in series with a return electrode or ground line. The voltage drop across this resistor may be measured using Ohm's law, consistent with details described above, and a return current may be calculated accordingly. This algorithm may then compare the measured return current to the delivered current to verify that the circuit is functioning correctly. The principle of conservation of charge and the use of Ohm's law may ensure that the measured return current is equal to the delivered current, accounting for any expected losses. A combination of shunt resistors and Hall effect sensors may provide accurate and non-intrusive current measurements. The algorithm may be configured to output a current verification status, such as, without limitation, a pass/fail status based on whether the return current is within the expected range. The algorithm may be further configured to measure and output return current values. The algorithm may be further configured to generate error alert(s), if any, such as, without limitation, one or more notifications if the return current is out of range, to indicate potential malfunctions.

With continued reference to FIGS. 8A-C, an algorithm for SS-SCM stimulator check may be implemented using one or more validation strategies. Suitable validation strategies for this algorithm may include bench testing, such as, without limitation, lab testing of hardware. Suitable validation strategies for this algorithm may further include intraoperative testing, such as, without limitation, real-time validation during SS-SCM stimulator implantation to ensure accurate performance. Suitable validation strategies for this algorithm may further include postoperative monitoring, such as, without limitation, continuous monitoring of return current in patients to verify long-term functionality.

With continued reference to FIGS. 8A-C, an algorithm for SS-SCM stimulator check may be implemented using one or more error-handling strategies. Suitable error-handling strategies for this algorithm may include identifying when a return current is outside an acceptable range and/or detecting inconsistencies in signal integrity that may affect measurements (i.e., a detection strategy). Suitable error-handling strategies for this algorithm may further include generating one or more immediate visual/auditory alerts to a practitioner, if a return current deviates from expected values, and/or highlighting one or more affected electrodes 122 using a graphical user interface (i.e., a notification strategy). Suitable error-handling strategies for this algorithm may further include recommending checking connections and electrode placement if return current is too low and/or suggesting further diagnostics if the return current is too high to indicate a possible short circuit or malfunction (i.e., a strategy for suggested actions). Suitable error-handling strategies for this algorithm may further include automatically logging an error event for future analysis and/or storing details about the error event including without limitation time, delivered current, return current, and/or system status, among others (i.e., a logging strategy).

With continued reference to FIGS. 8A-C, an algorithm for SS-SCM stimulator check may be configured to display real-time delivered and return current values using a display and/or graphical user interface. In some cases, these values may include or be presented using visual indicators to indicate range compliance. Similarly, this algorithm may implement an alert system by generating visual/auditory alerts for discrepancies in return current to be displayed using a display and/or graphical user interface.

With continued reference to FIGS. 8A-C, in some cases, an algorithm for EMG electrode impedance check may be implemented. Such an algorithm verifies individual EMG electrode impedance for accurate signal recording, ensures that each individual EMG electrode has the correct impedance to guarantee accurate and reliable signal recording, verifies the impedance of EMG electrodes across multiple muscles and/or myotomes to ensure proper sensor function for each electrode, and provides for a reliable and accurate EMG signal capture. Specifically, this algorithm may be configured to confirm that each EMG electrode is properly connected and maintains the correct impedance level, prevent signal degradation or inaccuracies caused by improper impedance in any electrode, and/or provide real-time feedback to a practitioner during sensor setup and monitoring. Input parameters for this algorithm may include an electrode configuration, i.e., a setup for EMG recording across multiple muscles or myotomes. Input parameters for this algorithm may further include one or more measured impedance values, i.e., impedance at each individual electrode placed on one or more muscles and/or myotomes. Input parameters for this algorithm may further include a reference impedance range, i.e., the acceptable impedance range for accurate EMG signal recording at each electrode.

With continued reference to FIGS. 8A-C, an algorithm for EMG electrode impedance check may be implemented using certain quantitative methodology. As a nonlimiting example, the algorithm may be configured to measure impedance at each individual EMG electrode using Ohm's law, consistent with details described above. A small current may be applied, and the resulting voltage drop across each electrode 122 may be measured to calculate the impedance. The measured impedance values may then be compared to a predefined reference range to ensure proper sensor function. Proper impedance levels at each electrode 122 may be essential for accurate EMG signal recording; a high impedance may indicate poor contact or incorrect sensor placement, whereas a low impedance may suggest a short circuit, consistent with details described above. The algorithm may be configured to output an impedance status, such as, without limitation, a pass/fail status for each individual EMG electrode based on whether the impedance falls within the acceptable range. The algorithm may be further configured to extract, measure, and output impedance values. The algorithm may be further configured to generate error alert(s), if any, such as, without limitation, one or more notifications if impedance values are out of range at any electrode 122 to indicate possible issues with sensor placement or contact.

With continued reference to FIGS. 8A-C, an algorithm for EMG electrode impedance check may be implemented using one or more validation strategies. Suitable validation strategies for this algorithm may include bench testing, such as, without limitation, initial validation using a controlled environment to simulate impedance at each EMG electrode. Suitable validation strategies for this algorithm may further include intraoperative testing, such as, without limitation, real-time validation during EMG sensor setup and monitoring to ensure accurate performance at each electrode 122. Suitable validation strategies for this algorithm may further include postoperative monitoring, such as, without limitation, continued monitoring of EMG electrode impedance during prolonged procedures to verify ongoing sensor functionality.

With continued reference to FIGS. 8A-C, an algorithm for EMG electrode impedance check may be implemented using one or more error-handling strategies. Suitable error-handling strategies for this algorithm may include identifying when an impedance is outside an acceptable range at any electrode 122 and/or detecting inconsistencies in signal integrity that may affect measurements (i.e., a detection strategy). Suitable error-handling strategies for this algorithm may further include generating one or more immediate visual/auditory alerts to a practitioner, if an impedance deviates from expected values at any electrode 122, and/or highlighting one or more affected electrodes 122 using a graphical user interface (i.e., a notification strategy). Suitable error-handling strategies for this algorithm may further include recommending repositioning one or more electrodes 122 or rechecking connections if an impedance is too high and/or suggesting further diagnostics if an impedance is too low to indicate a possible short circuit or other malfunction (i.e., a strategy for suggested actions). Suitable error-handling strategies for this algorithm may further include automatically logging an error event for future analysis and/or storing details about the error event including without limitation time, electrode location, impedance value, and/or system status, among others (i.e., a logging strategy).

With continued reference to FIGS. 8A-C, an algorithm for EMG electrode impedance check may be configured to display real-time impedance values for each electrode 122 using a display and/or graphical user interface. In some cases, these impedance values may include or be presented using visual indicators to indicate range compliance. Similarly, this algorithm may implement an alert system by generating visual/auditory alerts for discrepancies in impedance across any of the monitored electrodes 122, which may be displayed using a display and/or graphical user interface.

With continued reference to FIGS. 8A-C, an algorithm for EMG electrode signal quality verification may be implemented. Such an algorithm verifies signal quality using free-run EMG and compound motor action potential (cMAP) data, ensures that electrodes 122 provide good signal quality, and provides for accurate neuromuscular activity monitoring. This algorithm may operate through two key methodologies: the first key methodology includes implementing a free-run EMG signal analysis to measure a signal-to-noise ratio (SNR) during natural muscle activity to assess baseline signal quality; the second key methodology includes implementing a cMAP detection to verify signal quality in cMAP responses during stimulation to ensure valid neuromuscular activation. An algorithm for EMG electrode signal quality verification may be configured to confirm that electrodes are receiving high-quality signals with minimal noise, provide feedback on electrode performance during both natural muscle activity (i.e., free-run EMG) and during stimulation (i.e., cMAP detection), and/or prevent errors in monitoring caused by poor signal quality. Input parameters for this algorithm may include an electrode configuration, i.e., a setup of electrodes 122 connected to one or more muscles or myotomes of interest. Input parameters for this algorithm may further include free-run EMG data, i.e., EMG signals collected during natural muscle activity without external stimulation. Input parameters for this algorithm may further include cMAP data, i.e., recorded signals in response to electrical stimulation, including without limitation amplitude and/or latency. Input parameters for this algorithm may further include one or more signal quality metrics, such as, without limitation, a signal-to-noise ratio (SNR, i.e., a ratio of signal strength to background noise during free-run EMG) and/or one or more amplitude and latency thresholds (i.e., expected values during cMAP detection for proper neuromuscular activation).

With continued reference to FIGS. 8A-C, an algorithm for EMG electrode signal quality verification may be implemented using certain quantitative methodology. As a non-limiting example, this algorithm may be configured to implement a free-run EMG analysis. Performing a free-run EMG analysis may include continuously monitoring EMG signals without stimulation by focusing on muscle activity during a free-run mode. Performing a free-run EMG analysis may further include calculating an SNR by dividing the amplitude of an EMG signal by the level of background noise. A high SNR (e.g., >2:1) may indicate good signal quality, whereas a low SNR may suggest poor electrode contact or interference. As another nonlimiting example, this algorithm may be configured to implement cMAP detection. Specifically, after stimulation, the algorithm may analyze a cMAP response from each muscle or myotome. The algorithm may then compare the amplitude and/or latency of the cMAP signals against predefined clinical thresholds to verify correct activation. In some cases, the algorithm may detect one or more discrepancies in the response, if any, such as, without limitation, a low amplitude and/or a prolonged latency, among others, which may indicate a poor signal quality. For free-run EMG, a high SNR during free-run EMG may reflect minimal interference and strong electrode contact with a muscle or myotome. For cMAP, compound motor action potentials may be used as key indicators of neuromuscular function and provide a reliable measure of signal quality during active stimulation. The algorithm may be configured to output a signal quality status, such as, without limitation, a pass/fail status based on both free-run EMG SNR and cMAP detection thresholds. The algorithm may be further configured to measure and output SNR values during a free-run EMG mode to assess signal integrity. The algorithm may be further configured to output cMAP data, such as, without limitation, amplitude and latency values for each muscle during stimulation.

With continued reference to FIGS. 8A-C, an algorithm for EMG electrode signal quality verification may be implemented using one or more validation strategies. Suitable validation strategies for this algorithm may include bench testing, such as, without limitation, by simulating free-run EMG and cMAP detection in a controlled environment to assess signal quality. Suitable validation strategies for this algorithm may further include intraoperative testing, such as, without limitation, real-time validation during clinical procedures to verify signal quality across all electrodes 122. Suitable validation strategies for this algorithm may further include postoperative monitoring, such as, without limitation, continuous monitoring of electrode signal quality throughout the procedure to ensure long-term performance.

With continued reference to FIGS. 8A-C, an algorithm for EMG electrode signal quality verification may be implemented using one or more error-handling strategies. Suitable error-handling strategies for this algorithm may include identifying when an SNR is too low during free-run EMG or when a cMAP amplitude/latency falls outside an acceptable clinical range (i.e., a detection strategy). Suitable error-handling strategies for this algorithm may further include generating immediate visual/auditory alert if either free-run EMG or cMAP data indicate poor signal quality (i.e., a notification strategy). Suitable error-handling strategies for this algorithm may further include recommending rechecking electrode placement, adjusting connections, and/or modifying stimulation settings if signal quality issues are detected (i.e., a strategy for suggested actions). Suitable error-handling strategies for this algorithm may further include automatically logging signal quality issues, including without limitation time, electrode configuration, SNR values, and/or cMAP data discrepancies, among others (i.e., a logging strategy).

With continued reference to FIGS. 8A-C, an algorithm for EMG electrode signal quality verification may be configured to display real-time SNR values from free-run EMG and cMAP amplitude/latency data during stimulation. In some cases, these values may include or be presented using color-coded indicators to signify a pass/fail status. Similarly, this algorithm may implement an alert system by generating visual/auditory alerts for signal quality issues detected in either free-run EMG or cMAP response, which may be displayed using a display and/or graphical user interface.

With continued reference to FIGS. 8A-C, in some cases, an algorithm for EMG electrode setup verification may be implemented. Such an algorithm confirms correct electrode connections using latency and telemetry data, prevents incorrect electrode placement or connection, and ensures that electrodes 122 are connected correctly to the appropriate hardware setup and one or more muscle(s), muscle group(s), or myotomes of interest. Such an algorithm may utilize three distinct methodologies. The first methodology may include verifying the order of latencies based on hardware setup and signal propagation. The second methodology may include checking that measured latencies fall within the expected clinical values for each muscle, muscle group, or myotome. The third methodology may include using telemetry data from EMG sensors to determine the spatial orientation (left/right, rostral/caudal, etc.) and confirm that each electrode 122 is connected to the correct muscle, muscle group, or myotome. For the purposes of this disclosure, telemetry data are real-time physiological data that are remotely collected and transmitted from a patient to a central monitoring system. Telemetry data typically include vital signs such as heart rate, blood pressure, oxygen saturation, respiratory rate, and ECG readings, among others. Telemetry systems may use wireless technology to continuously transmit such data, allowing healthcare professionals to monitor a patient's health status from a distance, enabling prompt intervention if needed. An algorithm for EMG electrode setup verification may be configured to confirm that all electrodes 122 are connected to the correct muscles and aligned according to a hardware configuration, prevent errors caused by incorrect electrode placement or connection, and/or provide real-time feedback on electrode hookup to ensure proper configuration before stimulation. Input parameters for this algorithm may include data from one or more previous diagnostic or therapeutic sessions. Input parameters for this algorithm may further include one or more electrode configurations. i.e., one or more setups of active and reference electrodes 122 connected to certain muscle(s), muscle group(s), or myotomes. Input parameters for this algorithm may further include one or more defined latencies, i.e., one or more expected latencies for each muscle or muscle group based on clinical norms and electrode placement. Input parameters for this algorithm may further include telemetry data, i.e., signals from one or more EMG sensors providing information regarding electrode position (left/right, rostral/caudal, etc.) and muscle connection. Input parameters for this algorithm may further include a hardware setup map, i.e., a predefined map regarding which electrodes 122 should be connected to which muscles, including without limitation left/right and rostral/caudal orientations, among others.

With continued reference to FIGS. 8A-C, an algorithm for EMG electrode setup verification may be implemented using certain quantitative methodology. As a nonlimiting example, this algorithm may be implemented using a first methodology of latency and order verification. Specifically, the algorithm may verify that the order of latencies observed during stimulation matches the expected order based on signal propagation along the hardware setup. This method may ensure that electrodes 122 are connected in the correct sequence, confirming that signals are traveling to the appropriate muscles in the right order. As another nonlimiting example, this algorithm may be implemented using a second methodology of clinical value verification. Specifically, the algorithm may compare measured latencies from electrodes 122 against clinically expected latency values for each muscle or muscle group. Exemplary clinical latency values for muscle groups may include without limitation 10-12 ms for quadriceps (quads), 12-14 ms for psoas, 15-18 ms for tibialis anterior (TA), and 18-20 ms for abductor hallucis (AH), among others. If the latencies fall outside of these predefined clinical ranges, the algorithm may flag a connection as incorrect. As another nonlimiting example, this algorithm be implemented using a third methodology of telemetry-based verification. Specifically, EMG telemetry data may be used to identify the spatial orientation of each electrode 122 (left/right, rostral/caudal, etc.). Telemetry data may help the algorithm determine which muscle each electrode 122 is connected to confirm a correct connection based on orientation and location. If telemetry data reveals an incorrect orientation or muscle connection, the algorithm may flag an issue pertaining to the electrode connection.

With continued reference to FIGS. 8A-C, an algorithm for EMG electrode setup verification may be configured to implement one or more signal processing techniques. Cross-Correlation: Used to align EMG signals with expected cMAP waveforms from each muscle, ensuring the signals arrive in the correct order. As a nonlimiting example, the algorithm may implement a threshold detection technique; specifically, signal thresholds based on cMAP amplitude may be applied to detect when each muscle has been activated and help verify the order accordingly. As a nonlimiting example, the algorithm may implement a frequency domain analysis; specifically, frequency components of an EMG signal may be analyzed to isolate muscle activation patterns and ensure that a firing order matches expected responses. As a nonlimiting example, the algorithm may implement a time-delay estimation (TDE); specifically, time differences between EMG signals arriving from different electrodes 122 may be measured to confirm whether signal latency matches the correct muscle order. Latencies may correspond to signal travel time from stimulation to muscle response, allowing the algorithm to check connection order and verify clinical norms. EMG telemetry data may provide spatial orientation information to confirm left/right and rostral/caudal alignment, among others. The algorithm may be configured to output a connection status, such as, without limitation, a pass/fail status based on whether electrodes 122 are correctly connected according to latency order, clinical values, and telemetry data, among others. The algorithm may be further configured to generate error alert(s), if any, such as, without limitation, one or more notifications if electrodes 122 are connected to the wrong muscles, have abnormal latency values, and/or incorrect orientation, among others.

With continued reference to FIGS. 8A-C, an algorithm for EMG electrode setup verification may be implemented using one or more validation strategies. Suitable validation strategies for this algorithm may include bench testing, such as, without limitation, by simulating electrode connections and testing the algorithm's ability to detect incorrect connections based on latency, clinical values, and/or telemetry data, among others. Suitable validation strategies for this algorithm may further include intraoperative testing, such as, without limitation, real-time validation during electrode placement in a surgical environment. Suitable validation strategies for this algorithm may further include postoperative monitoring, such as, without limitation, continuous monitoring of electrode connection throughout the procedure to ensure correct ongoing placement.

With continued reference to FIGS. 8A-C, an algorithm for EMG electrode setup verification may be implemented using one or more error-handling strategies. Suitable error-handling strategies for this algorithm may include identifying when latency values or order are incorrect, when clinical latencies are outside expected ranges, and/or when telemetry data indicates one or more misaligned electrodes 122 (i.e., a detection strategy). Suitable error-handling strategies for this algorithm may further include generating one or more immediate visual/auditory alerts if any electrode 122 is incorrectly connected or oriented and/or highlighting the affected electrodes 122 on a graphical user interface (i.e., a notification strategy). Suitable error-handling strategies for this algorithm may further include recommending rechecking or repositioning of one or more electrodes 122 if flagged for incorrect connection and/or suggesting further diagnostics if telemetry data or clinical latencies are inconsistent (i.e., a strategy for suggested actions). Suitable error-handling strategies for this algorithm may further include automatically logging connection errors for future analysis and/or storing associated details including without limitation time of detection, electrode configuration, and/or discrepancies in latency or telemetry data, among others (i.e., a logging strategy).

With continued reference to FIGS. 8A-C, an algorithm for EMG electrode setup verification may be configured to display real-time electrode connections, including without limitation latency values, clinical value comparison, and/or telemetry-based orientation, with visual indicators for correct/incorrect connections. Similarly, this algorithm may implement an alert system by generating visual/auditory alerts for latency, clinical values, and/or telemetry data, sometimes with affected electrodes 122 highlighted. One or more of these elements may be displayed using a display and/or graphical user interface.

With continued reference to FIGS. 8A-C, in some cases, an algorithm for determining the laterality of active-reference electrode pairs may be implemented. Such an algorithm determines whether a specific active and reference electrode pair is on the left side, at the center, or on the right side with respect to a spinal cord and ensures precise stimulation. Specifically, this algorithm may proceed by stimulating the spinal cord using a multi-pulse paradigm and collecting either cMAPs or free-run EMG data in response. The algorithm may proceed with stimulation until an optimal stimulation is achieved (i.e., the maximum neuromuscular response is elicited without causing current spread to other areas of the spinal cord). After reaching such optimal stimulation, the algorithm may record the resulting cMAP and EMG data and apply signal processing techniques to determine the laterality (i.e., left, center, or right). The configuration will likely involve adjacent electrode pairs in a rostral-to-caudal configuration. The algorithm may be configured to determine whether a selected electrode pair (i.e., an active-reference electrode pair) is on the left side, at the center, or on right side with respect to the spinal cord, achieve optimal stimulation without causing undesired current spread to adjacent areas, and/or ensure accurate signal processing and analysis to determine laterality based on collected data. Input parameters for this algorithm may include an electrode configuration, i.e., one or more active and reference points set on adjacent electrodes 122, likely in a rostral-to-caudal configuration. Input parameters for this algorithm may further include a stimulation paradigm, i.e., a multi-pulse stimulation protocol applied to the spinal cord. Input parameters for this algorithm may further include stimulation data, i.e., cMAP data and/or free-run EMG signals collected during stimulation. Input parameters for this algorithm may further include one or more signal quality metrics, such as, without limitation, amplitude, latency, and/or SNR for optimal response detection, among others. Input parameters for this algorithm may further include one or more optimal stimulation criteria, which may be used as benchmarks for achieving maximum neuromuscular response (high cMAP amplitude and/or strong EMG signal) without current spread to undesired areas.

With continued reference to FIGS. 8A-C, for the purposes of this disclosure, laterality is a preference, dominance, or functional difference between the left and right sides of the body. Laterality may be used to describe one or more conditions or functions that are specific to one side of the body, such as without limitation left or right-handedness. Laterality may be used to diagnose and/or describe diseases or injuries that affect one side of the body more than the other. Laterality may be relevant in neurology, orthopedics, and medical imaging, among other contexts, where understanding the side-specific nature of symptoms or functions is critical for diagnosis and treatment planning.

With continued reference to FIGS. 8A-C, an algorithm for determining the laterality of active-reference electrode pairs may be implemented using certain quantitative methodology. As a nonlimiting example, for stimulation, the algorithm may be configured to apply a multi-pulse stimulation to an active-reference electrode pair, continuously monitor the response therefrom (cMAP or free-run EMG), and adjust the stimulation intensity until an optimal stimulation is achieved. As another nonlimiting example, for signal detection, the algorithm may be configured to achieve the highest cMAP amplitude or EMG signal without causing current spread to neighboring regions. As another nonlimiting example, for signal processing, once optimal stimulation is achieved, the algorithm may be configured to record the resulting cMAP and/or EMG signals. The algorithm may then apply cross-correlation or template matching techniques to compare the signal against predefined left, center, and right laterality templates, and apply signal symmetry analysis or time-delay estimation (TDE) to identify whether the response is stronger on the left side, at the center, or on the right side with respect to the spinal cord. As another nonlimiting example, for decision making, the algorithm may be configured to determine whether the active-reference electrode pair is positioned on the left side, at the center, or on the right side with respect to the spinal cord, based on a signal analysis. The algorithm may include one or more clinical values such as, without limitation, certain clinical criteria that may help a practitioner determine left, right, or center laterality based on signal amplitude, latency, and/or recruitment patterns. These values may guide how the algorithm interprets data to assign a laterality state accordingly. The algorithm may be configured to output a laterality status, such as, without limitation, a left, center, or right laterality based on the signal processing results. The algorithm may be further configured to record the stimulation intensity and duration that elicited the optimal response and output one or more optimal stimulation parameters accordingly. The algorithm may be further configured to output recorded signal data, such as, without limitation, stored cMAP and EMG data for further analysis or review. The algorithm may be further configured to generate error alert(s), if any, such as, without limitation, one or more notifications if the return current is out of range, to indicate potential malfunctions.

With continued reference to FIGS. 8A-C, an algorithm for determining the laterality of active-reference electrode pairs may be implemented using one or more validation strategies. Suitable validation strategies for this algorithm may include bench testing, such as, without limitation, by simulating stimulation and recording responses using both cMAP and EMG data in a controlled environment. Suitable validation strategies for this algorithm may further include intraoperative testing, such as, without limitation, real-time validation during actual SCS electrode placement procedures, ensuring accurate detection of laterality. Suitable validation strategies for this algorithm may further include postoperative monitoring, such as, without limitation, by monitoring stimulation during SCS use to confirm consistent laterality detection over time.

With continued reference to FIGS. 8A-C, an algorithm for determining the laterality of active-reference electrode pairs may be implemented using one or more error-handling strategies. Suitable error-handling strategies for this algorithm may include identifying when a stimulation is either suboptimal or causes current spread beyond the target area (i.e., a detection strategy). Suitable error-handling strategies for this algorithm may further include generating one or more immediate visual/auditory alerts if stimulation fails to achieve optimal response or if current spread occurs (i.e., a notification strategy). Suitable error-handling strategies for this algorithm may further include adjusting the stimulation intensity, electrode position, or switching to a different electrode pair if laterality cannot be determined (i.e., a strategy for suggested actions). Suitable error-handling strategies for this algorithm may further include automatically logging the stimulation parameters, recorded signal data, and laterality decision for further analysis (i.e., a logging strategy).

With continued reference to FIGS. 8A-C, an algorithm for determining the laterality of active-reference electrode pairs may be configured to display real-time feedback on, for example, and without limitation, stimulation intensity, cMAP/EMG signal quality, and/or laterality determination (left, center, or right), among others. Similarly, this algorithm may implement an alert system by generating visual/auditory alerts if stimulation is suboptimal or if laterality cannot be determined.

With continued reference to FIGS. 8A-C, in some cases, an algorithm for functional midline calculation of the spinal cord may be implemented. Such an algorithm determines the FML of a spinal cord using lateral electrode data and guides electrode placement. Specifically, this algorithm determines the FML of the spinal cord by systematically moving in a rostral-to-caudal and/or left-to-right pattern, such as without limitation by using data from the algorithm for determining the laterality of active-reference electrode pairs, as described above. For paddle electrodes, the algorithm may apply a line-fitting method to connect bilateral data points across the spinal cord to calculate the FML. For two single percutaneous column electrodes, the algorithm may analyze the left-side and right-side data to estimate where the FML exists, thereby drawing a physiologic centerline based on the recorded data points. The algorithm may be configured to accurately determine the FML of the spinal cord and guide electrode placement accordingly, ensure that data points collected during rostral-to-caudal and/or left-to-right movement are stored and analyzed to draw a precise FML, and/or provide real-time feedback to a practitioner regarding the positioning of electrodes 122 relative to the FML of a spinal cord. Input parameters for this algorithm may include laterality data, i.e., left, center, or right data points recorded during rostral-to-caudal and left-to-right electrode movements. Input parameters for this algorithm may further include electrode configuration, which may include without limitation the size, shape, and/or number of electrodes 122 being used. Specifically, for a paddle electrode, larger, flat electrodes 122 may often be arranged bilaterally; whereas for percutaneous electrodes, thin, column-like electrodes 122 may be typically inserted as two individual electrodes on either side of a spinal cord. Input parameters for this algorithm may further include a stimulation paradigm. Specifically, a multi-pulse stimulation protocol may be applied to stimulate and collect cMAP or EMG data. Input parameters for this algorithm may further include signal data, such as, without limitation, recorded cMAP and EMG data that may inform a laterality analysis.

With continued reference to FIGS. 8A-C, an algorithm for functional midline calculation of the spinal cord may be implemented using certain quantitative methodology. As a nonlimiting example, pertaining to data collection, the algorithm may use the algorithm for laterality of active-reference electrode pairs, as described above. Specifically, apparatus 100 may collect data as it moves one or more electrodes 122 in a rostral-to-caudal, left-to-right pattern, storing the laterality (left, center, right) at each position. As another nonlimiting example, when performing data analysis for paddle electrodes, once bilateral data points are collected (left, center, right), the algorithm may fit a line through these points to approximate the FML. The algorithm may be further configured to perform least squares linear regression or spline fitting to draw a fir line through the points and maximize the alignment between the left-side and right-side electrode data. The equation describing this fit line may represent the FML, and apparatus 100 may dynamically and/or iteratively adjust the fit as more data points are collected. As another nonlimiting example, when performing data analysis for percutaneous electrodes (such as, without limitation, two single percutaneous electrodes), the algorithm may be configured to analyze the left-side and right-side data points collected during a rostral-to-caudal movement, compute an FML by averaging the position of corresponding left-side and right-side points, and estimate the spinal cord's center based on the symmetry of the FML. A line that yields the most satisfactory fit may be calculated by minimizing the distance between the FML and the bilateral points to ensure that the calculated FML accurately reflects the center of the spinal cord (e.g., with residues randomly and symmetrically distributed across the fitting line). As another nonlimiting example, for 2D system and line fitting, the algorithm may be configured to implement a 2D coordinate system where the left-to-right axis and rostral-to-caudal axis are mapped for a spinal cord. An FML may be drawn by minimizing the error or residue between the fitted line and the collected points to ensure that the calculated FML represents the true anatomical FML. For cases where asymmetry or electrode shift occurs, the algorithm may be configured to recalculate and update an FML continuously to account for variations in the data. The algorithm may include one or more clinical values such as, without limitation, certain clinical metrics that may be used to guide the positioning of an electrode 122 relative to the FML of a spinal cord. As a nonlimiting example, such clinical metrics may include laterality metrics and/or symmetry measures, among others. The algorithm may be configured to output the position of an FML, such as, without limitation, by exacting the calculated position of the FML pertaining to a spinal cord and displaying the calculated position visually for a practitioner. The algorithm may be configured to output stored laterality data, such as, without limitation, data points recorded during the movement of one or more electrodes 122 and used for calculating an FML. The algorithm may be configured to generate and output a graphical representation, such as, without limitation, a visualization of an FML with respect to one or more paddle or percutaneous electrodes, thereby ensuring proper alignment.

With continued reference to FIGS. 8A-C, an algorithm for functional midline calculation of the spinal cord may be implemented using one or more validation strategies. Suitable validation strategies for this algorithm may include bench testing, such as, without limitation, by simulating the collection of laterality data and verifying the accuracy of the functional midline calculation using both paddle and percutaneous electrodes. Suitable validation strategies for this algorithm may further include intraoperative testing. Suitable validation strategies for this algorithm may further include postoperative monitoring, such as, without limitation, by confirming that the calculated FML remains consistent during long-term use of electrodes 122.

With continued reference to FIGS. 8A-C, an algorithm for functional midline calculation of the spinal cord may be implemented using one or more error-handling strategies. Suitable error-handling strategies for this algorithm may include identifying when collected data points are inconsistent and/or when the functional midline calculation becomes unstable (i.e., a detection strategy). Suitable error-handling strategies for this algorithm may further include generating one or more immediate visual/auditory alerts if the FML cannot be calculated accurately or if the data points suggest a level of asymmetry beyond acceptable ranges (i.e., a notification strategy). Suitable error-handling strategies for this algorithm may further include recommending adjusting electrode positioning or recalculating the FML if discrepancies are detected in the stored data (i.e., a strategy for suggested actions). Suitable error-handling strategies for this algorithm may further include automatically logging all functional midline calculation attempts and results, including without limitation electrode positions and laterality data (i.e., a logging strategy).

With continued reference to FIGS. 8A-C, an algorithm for functional midline calculation of the spinal cord may be configured to display real-time visual representation of the calculated FML with the stored laterality data points shown on either side of a spinal cord. Similarly, this algorithm may implement an alert system by generating visual/auditory alerts if the FML cannot be accurately calculated or if electrode placement deviates from the expected FML.

With continued reference to FIGS. 8A-C, in some cases, an algorithm for myotome dominance detection may be implemented using cMAP and free-run EMG. Such an algorithm identifies which myotomes are dominantly activated during stimulation and helps target specific muscle groups. Specifically, this algorithm may analyze cMAP and free-run EMG data at each point to determine which muscle(s), muscle group(s), or myotome(s) is being dominantly activated between the quadriceps (quads), tibialis anterior (TA), abductor hallucis (AH), and psoas, among others. This algorithm may use data collected from an active-reference electrode pair setup and factor in stimulation values by focusing on optimal data points to assess which muscle(s), muscle group(s), and/or myotome(s) is being stimulated most effectively. This algorithm may help a practitioner understand which neural targets are being activated during stimulation by identifying a dominant muscle, muscle group, or myotome at each stimulation point. The algorithm may be configured to help a practitioner understand which myotomes are activated during stimulation for better targeting of the spinal cord. This algorithm may be configured to provide accurate data on which muscle(s), muscle group(s), or myotome(s) (quads, TA, AH, psoas, etc.) shows the strongest response during stimulation. The algorithm may be configured to ensure the results are based on optimal stimulation data by avoiding current spread or suboptimal responses. Input parameters for this algorithm may include active-reference electrode pair data, i.e., data collected during stimulation using an active-reference electrode pair configuration. Input parameters for this algorithm may further include one or more stimulation parameters, which may include without limitation stimulation intensity, pulse width, and/or frequency used during a procedure, among others, consistent with details described above.

With continued reference to FIGS. 8A-C, an algorithm for myotome dominance detection may be implemented using certain quantitative methodology. As a nonlimiting example, for stimulation monitoring, the algorithm may be configured to continuously monitor cMAP and free-run EMG signals during stimulation for each muscle, muscle group, or myotome (quads, TA, AH, psoas). Accordingly, the algorithm may be configured to tracks stimulation intensity, frequency, and/or pulse width, among others, thereby ensuring that data collection is performed at optimal stimulation points. As another nonlimiting example, for signal analysis, the algorithm may be configured to analyze the amplitude and latency of cMAP data for each muscle to detect which muscle shows the strongest response to stimulation. The algorithm may be configured to spontaneously monitor free-run EMG data to observe baseline levels of activity for each muscle before and after stimulation. The algorithm may be configured for optimal stimulation detection, wherein the algorithm uses stimulation parameters and the strength of a recorded signal (cMAP amplitude, SNR, etc.) to ensure that the data reflects maximum neuromuscular activation without current spread. As another nonlimiting example, for dominant myotome determination, the algorithm may be configured to compare the strength and latency of cMAP signals across all muscle groups to determine which myotome is the most dominant at each stimulation point. The algorithm may be configured according to rank muscles by response strength and prioritize the one or more muscles with the highest cMAP amplitude and lowest latency. The algorithm may be further configured to incorporate free-run EMG data and validate whether the detected myotome is being actively stimulated or passively affected by other nearby stimulation. As another nonlimiting example, for stimulation optimization, the algorithm may be configured to continuously adjust the intensity of, evaluate signal responses until optimal stimulation is achieved, and record the stimulation parameters when the optimal data is collected for each muscle group. The algorithm may include one or more clinical values such as, without limitation, certain clinical metrics that may be used to determine when a myotome is dominantly activated. Such clinical metrics may include without limitation specific amplitude thresholds for each muscle group and latency cutoffs to ensure optimal targeting, among others. The algorithm may be configured to output a dominant myotome, such as, without limitation, by identifying and displaying the dominant myotome (quads, TA, AH, or psoas, among others) at each stimulation point. The algorithm may be further configured to output one or more stimulation parameters, such as, without limitation, by logging the intensity of stimulation, pulse width, and/or frequency, among others, that are used during optimal activation. The algorithm may be further configured to output record signal data, such as, without limitation, by storing cMAP and free-run EMG data for further review or analysis, including without limitation the signal strength for each muscle, muscle group, or myotome.

With continued reference to FIGS. 8A-C, an algorithm for myotome dominance detection may be implemented using one or more validation strategies. Suitable validation strategies for this algorithm may include bench testing, such as, without limitation, by simulating cMAP and free-run EMG data and verifying the algorithm's ability to accurately detect and rank dominant myotomes. Suitable validation strategies for this algorithm may further include intraoperative testing, such as, without limitation, real-time validation during clinical use, thereby ensuring that the algorithm accurately identifies dominant myotomes during stimulation. Suitable validation strategies for this algorithm may further include postoperative monitoring, such as, without limitation, by continuous assessment of electrode performance and signal accuracy over time.

With continued reference to FIGS. 8A-C, an algorithm for myotome dominance detection may be implemented using one or more error-handling strategies. Suitable error-handling strategies for this algorithm may include identifying when one or more signals are suboptimal (low amplitude, high latency, or current spread, among others), or when the algorithm cannot detect a dominant myotome (i.e., a detection strategy). Suitable error-handling strategies for this algorithm may further include generating one or more immediate visual/auditory alerts if dominant myotomes cannot be determined or if the data indicates suboptimal stimulation (i.e., a notification strategy). Suitable error-handling strategies for this algorithm may further include recommending adjusting stimulation intensity, electrode placement, and/or targeting different muscles, etc., if no dominant myotome is detected (i.e., a strategy for suggested actions). Suitable error-handling strategies for this algorithm may further include automatically logging dominant myotome detection events and/or any suboptimal signal conditions for further analysis (i.e., a logging strategy).

With continued reference to FIGS. 8A-C, an algorithm for myotome dominance detection may be configured to display real-time ranking of myotomes based on signal strength using a display and/or graphical user interface, thereby showing the most dominantly activated myotome for each stimulation point. Similarly, this algorithm may implement an alert system by generating visual/auditory alerts if suboptimal stimulation or signal spread occurs, with one or more areas highlighted where dominant myotome detection has failed. One or more of these elements may be displayed using a display and/or graphical user interface.

With continued reference to FIGS. 8A-C, in some cases, an algorithm for neural structure identification may be implemented. Such an algorithm analyzes active and reference electrode data and identifies/determines whether a dorsal column or nerve roots are being stimulated. The algorithm uses anatomical input data (e.g., data collected from T8 and T9 from a spinal cord), an activation pattern of cMAP data, and the stimulation intensity at which the response occurs to provide a practitioner with a clear understanding of the specific neural structure being targeted. This algorithm also differentiates central and peripheral targets for precise stimulation and informs a practitioner whether the stimulation is affecting the central dorsal column or the peripheral nerve roots instead. This algorithm may be configured to provide accurate identification regarding whether the stimulation is targeting the dorsal column, or the nerve roots, based on electrode placement and/or response patterns. This algorithm may be further configured to use activation patterns and stimulation thresholds to differentiate between the two types of neural structures. Accordingly, the algorithm may enable real-time decision-making for clinicians during stimulation procedures. Input parameters for this algorithm may include an anatomical input, i.e., anatomical location of one or more electrodes 122 relative to a spinal cord and nerve roots (e.g., T8 and/or T9). Input parameters for this algorithm may further include active-reference electrode data, i.e., the stimulation data from active-reference electrode pairs. Input parameters for this algorithm may further include a stimulation Intensity, i.e., the intensity (current, voltage, pulse width) at which the cMAP response is elicited. Input parameters for this algorithm may further include one or more expected neural responses, such as, without limitation, typical cMAP response patterns associated with either dorsal column stimulation or nerve root stimulation.

With continued reference to FIGS. 8A-C, an algorithm for neural structure identification may be implemented using certain quantitative methodology. As a nonlimiting example, for anatomical localization, the algorithm may be configured to use an input anatomical location (e.g., T8, T9) to estimate a proximity to either a dorsal column or nerve roots. The algorithm may be configured to reference anatomical maps of a spinal cord to estimate which neural structures are the closest to a specific electrode configuration. As another nonlimiting example, for cMAP pattern analysis, the algorithm may be configured to analyze cMAP amplitude and latency at various stimulation intensities. Dorsal column stimulation is typically characterized by longer latencies and higher thresholds for activation due to the central nature of the dorsal column, whereas nerve root stimulation is typically characterized by shorter latencies and lower thresholds for activation due to the peripheral location and proximity of the nerve roots to one or more electrodes 122. As another nonlimiting example, for stimulation intensity and threshold comparison, the algorithm may be configured to track the stimulation intensity at which a cMAP response is triggered and compare this intensity with predefined thresholds for dorsal column and nerve root activation. Higher stimulation thresholds (e.g., >20 mA) and delayed responses may suggest dorsal column activation, whereas lower stimulation thresholds (e.g., 5-10 mA) with immediate responses may suggest nerve root activation. As another nonlimiting example, for neural structure differentiation, the algorithm may be configured to classify whether an electrode 122 is stimulating the dorsal column or nerve roots based on the anatomical input (cMAP pattern, etc.). The algorithm may adjust dynamically and/or iteratively as more data points are collected, refining its classification based on signal behavior and stimulation settings. The algorithm may include one or more clinical values such as, without limitation, certain clinical thresholds and activation patterns typical of dorsal column vs. nerve root stimulation, which may guide the algorithm's classification of neural structures. The algorithm may be configured to output one or more neural structure classifications that identify whether a current stimulation is targeting a dorsal column or nerve roots. The algorithm may be further configured to output one or more activation thresholds that display the stimulation intensity required to activate the structure (e.g., threshold current/voltage or the like). The algorithm may be further configured to output cMAP and/or signal data, thereby providing real-time data on cMAP amplitude, latency, and/or signal response patterns, among others, for further review or analysis.

With continued reference to FIGS. 8A-C, an algorithm for neural structure identification may be implemented using one or more validation strategies. Suitable validation strategies for this algorithm may include bench testing, such as without by simulating both dorsal column and nerve root responses to ensure that the algorithm accurately differentiates between them. Suitable validation strategies for this algorithm may further include intraoperative testing, such as, without limitation, by validating the algorithm's performance during live procedures where both dorsal column and nerve root stimulation may occur. Suitable validation strategies for this algorithm may further include postoperative monitoring, such as, without limitation, by monitoring electrode placement and signal accuracy over time to ensure consistent neural structure identification.

With continued reference to FIGS. 8A-C, an algorithm for neural structure identification may be implemented using one or more error-handling strategies. Suitable error-handling strategies for this algorithm may include identifying when the algorithm cannot confidently classify a neural structure, due to factors such as, without limitation, conflicting signal patterns, ambiguous stimulation responses, or the like (i.e., a detection strategy). Suitable error-handling strategies for this algorithm may further include generating one or more immediate visual/auditory alerts if the algorithm cannot determine whether a dorsal column or nerve roots are being stimulated (i.e., a notification strategy). Suitable error-handling strategies for this algorithm may further include recommending adjusting electrode placement, increasing or decreasing stimulation intensity, and/or reviewing anatomical inputs if the classification fails (i.e., a strategy for suggested actions). Suitable error-handling strategies for this algorithm may further include automatically logging all neural structure classification events, along with any uncertainty in the signal data, for further review (i.e., a logging strategy).

With continued reference to FIGS. 8A-C, an algorithm for neural structure identification may be configured to display real-time visualization of neural structure classification (dorsal column vs. nerve roots) with cMAP amplitude and latency data. Similarly, this algorithm may implement an alert system by generating visual/auditory alerts to be displayed using a display and/or graphical user interface if there is uncertainty in neural structure classification and/or if the stimulation intensity falls outside expected thresholds.

With continued reference to FIGS. 8A-C, in some cases, an algorithm for target matching is implemented based on laterality, myotomes, and structure. Such an algorithm matches user-defined targets (e.g., laterality, myotomes, structure) with electrode pairs and ensures precise targeting based on user input. Specifically, this algorithm may allow a user to define a target based on criteria such as without limitation laterality (left, right, center), specific myotomes (e.g., quadriceps, tibialis anterior, abductor hallucis, psoas), and/or neural structure (dorsal column or nerve roots), among others. The algorithm may use outputs of all previously developed algorithms, including without limitation one or more algorithms for laterality determination, myotome dominance detection, and/or neural structure identification, among others, to evaluate which active-reference electrode pair matches the target. The algorithm may return one or more matching active-reference electrode pairs based on a set of matching criteria. Alternatively, the algorithm may not return any match if the criteria are not met. The algorithm may be configured to allow a user, such as a practitioner, to define specific targets based on anatomical and physiological features. The algorithm may be configured to accurately match user-defined targets to active-reference electrode pairs using data from all previous algorithms. The algorithm may be configured to provide flexibility in handling multiple matches or an absence of matches. Input parameters for this algorithm may include one or more target criteria. Such target criteria may include laterality, such as, without limitation, user-defined left, right, or center. Such target criteria may further include one or more myotomes, such without limitation one or more user-selected target myotomes from available muscle groups (quads, TA, AH, psoas, etc.). Such target criteria may include one or more structures, wherein the user specifies whether the dorsal column or nerve roots are being targeted. Input parameters for this algorithm may include one or more outputs from other algorithms described above. Such outputs may include without limitation laterality data, e.g., results from an algorithm for laterality of active-reference electrode pairs; myotome dominance data, e.g., results from an algorithm for myotome dominance detection that identify which myotomes are activated; neural structure data, e.g., results from an algorithm for neural structure identification that specify whether the dorsal column or nerve roots are being stimulated. Input parameters for this algorithm may further include active-reference electrode data, i.e., data pertaining to electrode pairs that are evaluated based on the criteria provided.

With continued reference to FIGS. 8A-C, an algorithm for target matching may be implemented using certain quantitative methodology. As a nonlimiting example, for target definition, a user may select one or more target criteria, such as, without limitation, laterality, myotomes, structure, or the like, from a predefined set of options. The algorithm may accordingly be configured to translate such criteria into search filters, thereby ensuring that only relevant active-reference electrode pairs may be considered. As another nonlimiting example, for matching processes, the algorithm may be configured to perform laterality matching by comparing the laterality output by an algorithm for laterality of active-reference electrode pairs, as described above, against a user-defined laterality target (left, right, center). Similarly, the algorithm may be configured to perform myotome matching by evaluating myotome dominance data output by an algorithm for myotome dominance detection and checking if the dominant myotome matches the user-defined target. Finally, the algorithm may be configured to perform structure matching using the neural structure data (dorsal column or nerve roots) and verify if the correct neural structure is being stimulated based on the user's input. As another nonlimiting example, for result evaluation, the algorithm may be configured to search through active-reference electrode pairs to find one or more matches based on the above criteria. Accordingly, the algorithm may be configured to identify which electrode pair or pairs meet all the user-defined criteria for laterality, myotome activation, and neural structure. The algorithm may be configured to output multiple matches if more than one active-reference electrode pair meets the criteria, or no match if none of the active-reference electrode pairs satisfy all conditions. The algorithm may include one or more clinical values defining acceptable ranges for laterality, myotome activation thresholds, and structure-based stimulation. These values may be used to ensure that the matching is clinically relevant. The algorithm may be configured to output one or more matching active-reference electrode pairs by displaying the one or more active-reference electrode pairs that match the user-defined target criteria. The algorithm may be configured to output a match count by providing a count of how many active-reference electrode pairs meet a defined target (multiple matches or no match, etc.). The algorithm may be configured to output a criteria breakdown by showing how each matching active-reference electrode pair satisfies the laterality, myotome, and structure criteria.

With continued reference to FIGS. 8A-C, an algorithm for target matching may be implemented using one or more validation strategies. Suitable validation strategies for this algorithm may include bench testing, such as, without limitation, by simulating user-defined target inputs and verifying the algorithm's ability to correctly match or return no matches based on the data. Suitable validation strategies for this algorithm may further include intraoperative testing, such as, without limitation, real-time matching during procedures, thereby ensuring that the algorithm accurately identifies one or more active-reference electrode pairs that meet the user's clinical targets. Suitable validation strategies for this algorithm may further include postoperative monitoring, such as, without limitation, by tracking electrode performance over time to ensure consistent matching based on input criteria.

With continued reference to FIGS. 8A-C, an algorithm for target matching may be implemented using one or more error-handling strategies. Suitable error-handling strategies for this algorithm may include identifying when no active-reference electrode pairs meet the user-defined criteria (i.e., a detection strategy). Suitable error-handling strategies for this algorithm may further include generating one or more immediate visual/auditory alerts if no match is found or if multiple matches occur when only one was expected (i.e., a notification strategy). Suitable error-handling strategies for this algorithm may further include recommending adjusting the user-defined target, electrode positioning, or stimulation parameters if no match is found (i.e., a strategy for suggested actions). Suitable error-handling strategies for this algorithm may further include automatically logging all match attempts, including user-defined criteria, one or more matched pairs, or no-match results (i.e., a logging strategy).

With continued reference to FIGS. 8A-C, an algorithm for target matching may be configured to display matched one or more active-reference electrode pairs in real-time, showing a user how each active-reference electrode pair meets the defined target criteria. Similarly, this algorithm may implement an alert system by generating visual/auditory alerts to be displayed using a display and/or graphical user interface if no match is found, or if multiple matches occur where a single match was expected.

Figure 9A:
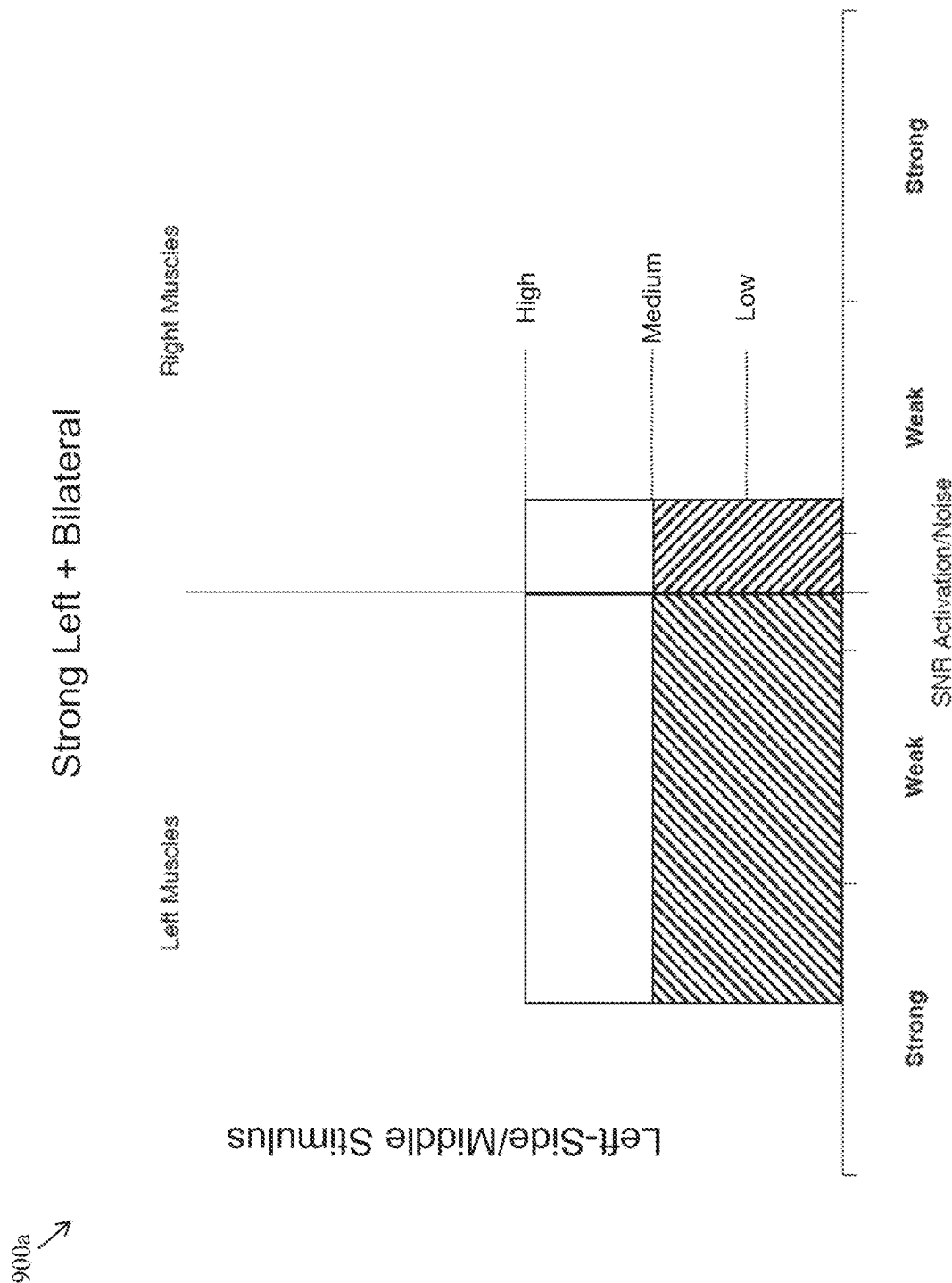
FIGS. 9A-B are exemplary visual representations of the processed EMG data from FIGS. 7A-D.
Figure 9B:
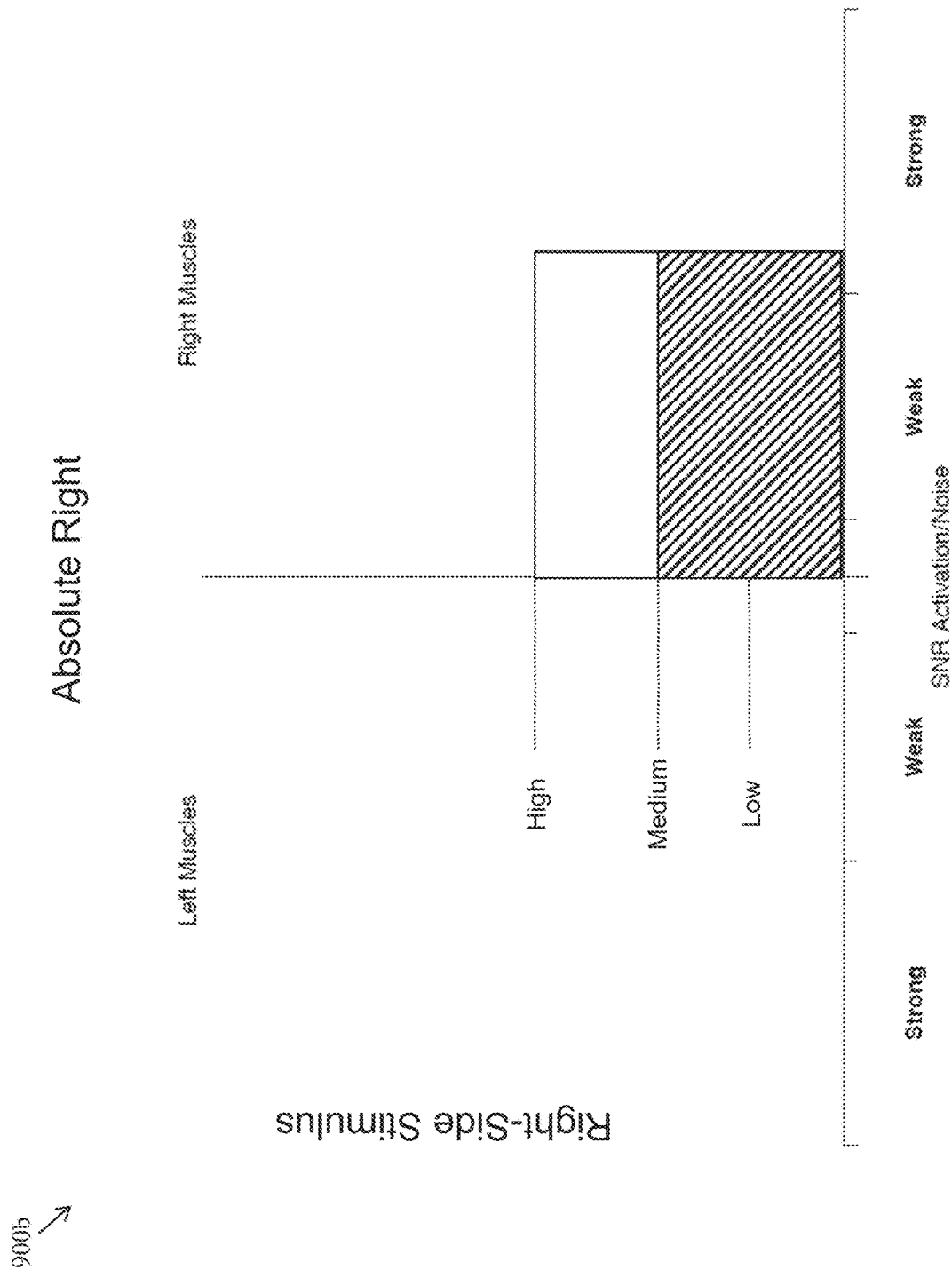

Referring now to FIGS. 9A-B, FIGS. 9A-B show exemplary outputs 900a-b generated by algorithms described herein, based on data depicted in FIGS. 7A-D. FIG. 9A includes a case of strong left and bilateral activation, whereas FIG. 9B includes a case of absolute right activation. As shown, the length of the bar represents the strength of muscle activation (e.g., the activation ratio), whereas the width of the bar represents the activation efficiency, consistent with details described above.

Clinical Tracking

Figure 10:
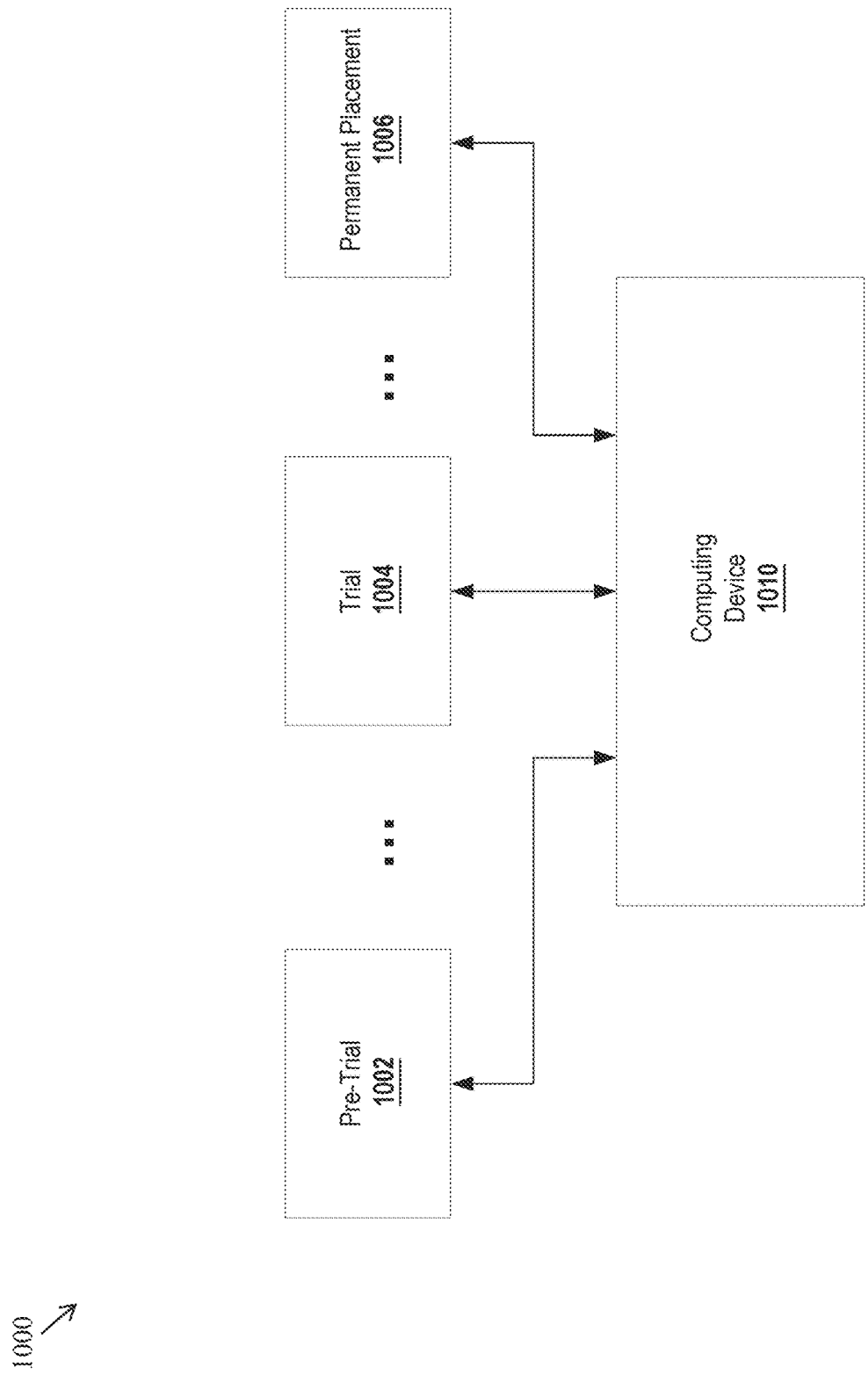
FIG. 10 is a block diagram illustrating an exemplary embodiment of the use of a computing device during a pre-trial phase, a trial phase, and a permanent placement phase of electrode placement.

Referring now to FIG. 10, FIG. 10 includes a block diagram 1000 illustrating an exemplary embodiment of the use of a computing device 1010 during a pre-trial phase 1002, a trial phase 1004, and a permanent placement phase 1006 of electrode placement. Computing device 1010 may be implemented using any means consistent with details described above pertaining to computing device 110 and computing device 210 without limitation. During pre-trial phase 1002, a patient may be partially sedated, and electrodes may be placed at a target site near the spine of the patient. Computing device 1010 may be used to facilitate electrode placement during pre-trial phase 1002, as described above with respect to FIGS. 1-9. Data collected during pre-trial phase 1002 (e.g., raw EMG data, analyzed EMG data, visual representations of EMG data, patient data, stimulation parameter data, fluoroscopy images captured during electrode placement, etc.) may be stored in a memory of the computing device 1010 (not shown). After pre-trial phase 1002, a temporary stimulation device may be programmed with instructions for therapeutic stimulation parameters and coupled to an implanted electrode lead.

With continued reference to FIG. 10, the patient then undergoes trial phase 1004, during which a therapeutic stimulation may be applied to the implanted electrode lead. Trial phase 1004 may last approximately two weeks. At the end of trial phase 1004, a practitioner may assess the efficacy of therapeutic stimulation based on patient feedback. In one or more embodiments, a practitioner may also assess the positioning of electrodes 122 using computing device 1010. As a nonlimiting example, after trial phase 1004, computing device 1010 may be used to measure EMG signals in response to a stimulation protocol to determine whether the electrode lead has migrated and/or the activation of myotomes has changed. In one or more embodiments, data collected during pre-trial phase 1002 may be compared to data collected in trial phase 1004 to determine whether any differences in myotome activation exist. In one or more embodiments, a practitioner may determine whether electrodes 122 have remained in the target site, and if so, whether stimulating the target site had any therapeutic effect. If electrodes 122 have migrated, and no therapeutic effect was observed, a practitioner may opt to reposition the electrodes 122 and potentially repeat trial phase 1004. If electrodes 122 have not migrated, but no therapeutic effect was observed, then a practitioner may opt to choose a different target site and potentially repeat trial phase 1004. If electrodes 122 have not migrated, and a therapeutic effect was observed, then a practitioner may opt to move into permanent placement phase 1006 and permanently place electrodes 122 at the target site.

With continued reference to FIG. 10, computing device 1010 may be used to facilitate permanent electrode placing based on results from trial phase 1004. In one or more embodiments, data collected during pre-trial phase 1002 and trial phase 1004 may be used to help guide permanent placement phase 1006. In one or more embodiments, a visual representation of EMG data from pre-trial phase 1002 and/or trial phase 1004 may be overlaid with an image of a patient's spine to help guide permanent placement phase 1006. In one or more embodiments, a comparison of pretrial phase 1002 EMG data and trial phase 1004 EMG data may allow a practitioner to efficiently discern the cause of issues during trial phase 1004 as well as avoid permanently placing an electrode lead in a sub-optimal position. In one or more embodiments, even after permanent placement phase 1006, a practitioner may opt to monitor migration of electrodes 122 over an extended timeline using computing device 1010. In one or more embodiments, if a patient begins experiencing complications, a practitioner may monitor migration of the electrode lead using computing device 1010. The ability of a practitioner to receive quantitative feedback regarding electrode placement in relation to an FML at each stage of the implantation process and beyond helps to improve accuracy of placement, thereby improving patient outcomes.

With continued reference to FIG. 10, it is to be noted that any one or more of the aspects and embodiments described herein may be conveniently implemented using one or more machines (e.g., one or more computing devices that are utilized as a user computing device for an electronic document, one or more server(s) devices, such as a document server, etc.) programmed according to the teachings of the present specification. Appropriate software coding may readily be prepared by skilled programmers based on the teachings of the present disclosure. Aspects and implementations discussed above employing software and/or software modules may also include appropriate hardware for assisting in the implementation of the machine executable instructions of the software and/or software module.

With continued reference to FIG. 10, such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. For the purposes of this disclosure, a machine-readable storage medium does not include transitory forms of signal transmission.

With continued reference to FIG. 10, such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

With continued reference to FIG. 10, examples of a computing device include, but are not limited to, an electronic book reading device, a computer workstation, a terminal computer, a server(s) computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 11:
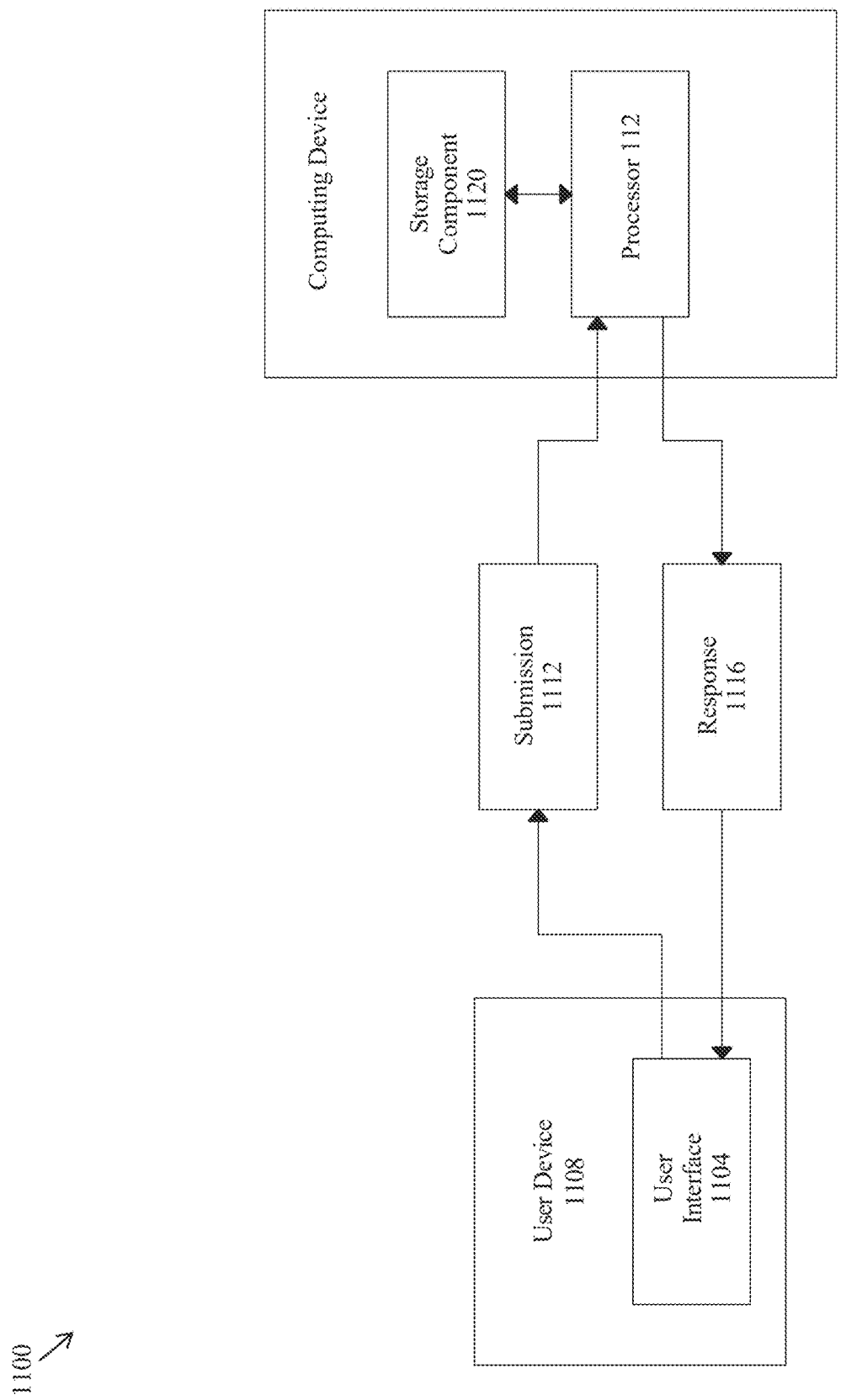
FIG. 11 is an exemplary embodiment of a chatbot system.

Referring now to FIG. 11, in one or more embodiments, apparatus 100 may perform one or more of its functions by implementing at least a chatbot system 1100, an exemplary embodiment of which is schematically illustrated. In one or more embodiments, a user interface 1104 may be communicatively connected with a computing device that is configured to operate a chatbot. In some cases, user interface 1104 may be local to a computing device. Alternatively, or additionally, in some other cases, user interface 1104 may be remote to computing device, e.g., as part of a user device 1108, and communicative with the computing device and processor 112 therein, by way of one or more networks, such as, without limitation, the internet. Alternatively, or additionally, user interface 1104 may communicate with user interface 1104 and/or computing device using telephonic devices and networks, such as, without limitation fax machines, short message service (SMS), or multimedia message service (MMS). Commonly, user interface 1104 may communicate with computing device using text-based communication, for example without limitation using a character encoding protocol, such as American Standard for Information Interchange (ASCII). Typically, user interface 1104 may conversationally interface a chatbot, by way of at least a submission 1112, from the user interface 1104 to the chatbot, and a response 1116, from the chatbot to the user interface 1104. In many cases, one or both of submission 1112 and response 1116 are text-based communication. Alternatively, or additionally, in some cases, one or both of submission 1112 and response 1116 are audio-based communication.

With continued reference to FIG. 11, submission 1112, once received by user interface 1104 and/or computing device that operates a chatbot, may be processed by processor 112. In one or more embodiments, processor 112 may process submission 1112 using one or more of keyword recognition, pattern matching, and natural language processing. In one or more embodiments, processor 112 may employ real-time learning with evolutionary algorithms. In one or more embodiments, processor 112 may retrieve a pre-prepared response from at least a storage component 1120, based upon submission 1112. Alternatively, or additionally, in one or more embodiments, processor 112 may communicate a response 1116 without first receiving a submission 1112, thereby initiating a conversation. In some cases, processor 112 may communicate an inquiry to user interface 1104 and/or computing device, wherein processor 112 is configured to process an answer to the inquiry in a following submission 1112 from the user interface 1104 and/or computing device. In some cases, an answer to an inquiry presented within submission 1112 from user interface 1104 and/or computing device may be used by the computing device as an input to another function.

Figure 12:
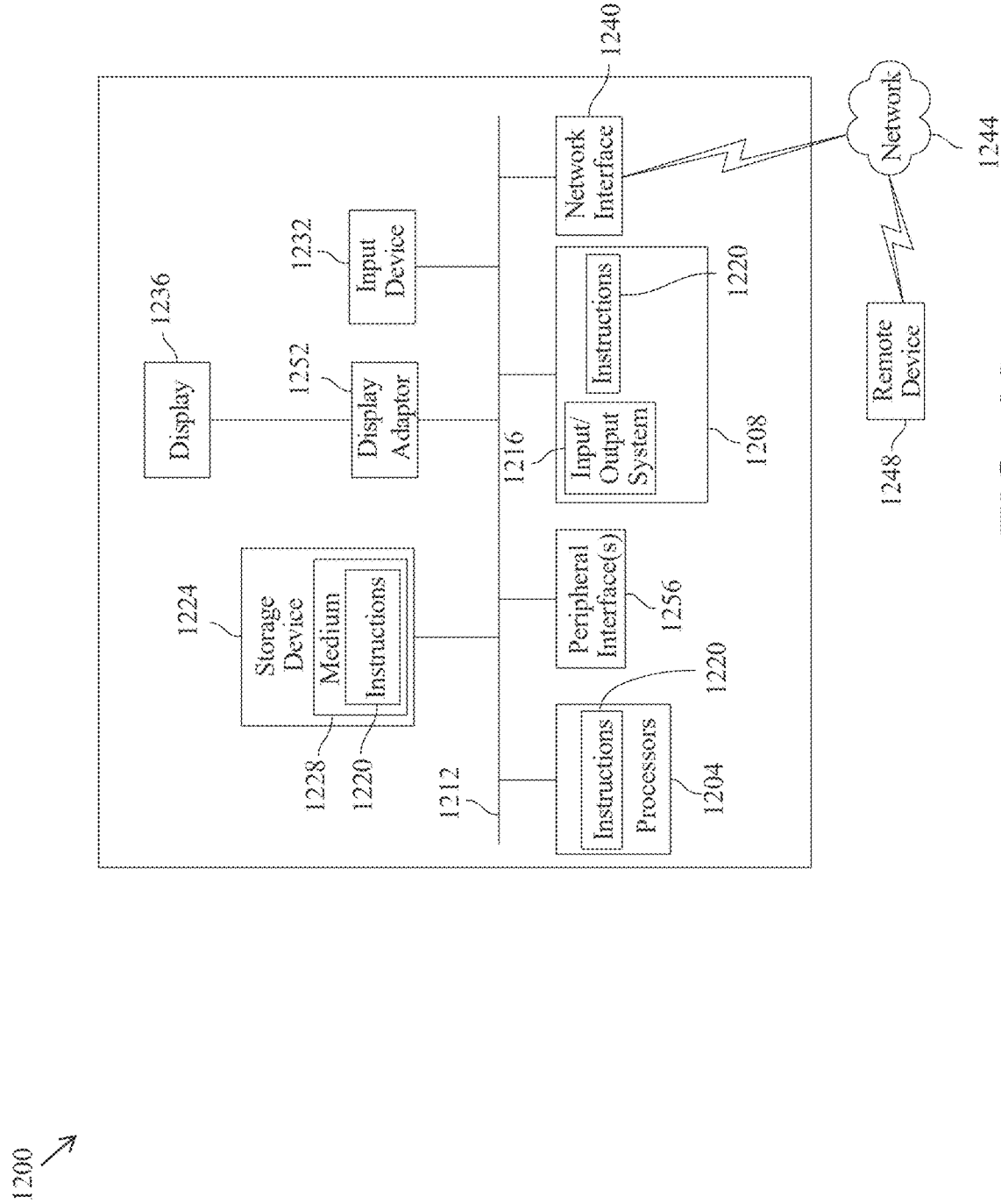
FIG. 12 is a block diagram illustrating exemplary embodiment of a computing system that can be used to implement any one or more of the methodologies disclosed herein and any one or more portions thereof.

Referring now to FIG. 12, it is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to one of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module. Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission. Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein. Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

With continued reference to FIG. 12, the figure shows a diagrammatic representation of one embodiment of a computing device in the exemplary form of a computing system 1200 within which a set of instructions for causing the computing system 1200 to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computing system 1200 may include a processor 1204 and a memory 1208 that communicate with each other, and with other components, via a bus 1212. Bus 1212 may include any of several types of bus structures including, but not limited to, a memory bus, a memory controller, a peripheral bus, a local bus, and any combinations thereof, using any of a variety of bus architectures. Processor 1204 may include any suitable processor, such as, without limitation, a processor incorporating logical circuitry for performing arithmetic and logical operations, such as an arithmetic and logic unit, which may be regulated with a state machine and directed by operational inputs from memory and/or sensors; processor 1204 may be organized according to Von Neumann and/or Harvard architecture as a non-limiting example. Processor 1204 may include, incorporate, and/or be incorporated in, without limitation, a microcontroller, microprocessor, digital signal processor, field programmable gate array, complex programmable logic device, graphical processing unit, general-purpose graphical processing unit, tensor processing unit, analog or mixed signal processor, trusted platform module, a floating-point unit, and/or system on a chip.

With continued reference to FIG. 12, memory 1208 may include various components (e.g., machine-readable media) including, but not limited to, a random-access memory component, a read only component, and any combinations thereof. In one example, a basic input/output system 1216, including basic routines that help to transfer information between elements within computing system 1200, such as during start-up, may be stored in memory 1208. Memory 1208 (e.g., stored on one or more machine-readable media) may also include instructions (e.g., software) 1220 embodying any one or more of the aspects and/or methodologies of the present disclosure. In another example, memory 1208 may further include any number of program modules including, but not limited to, an operating system, one or more application programs, other program modules, program data, and any combinations thereof.

With continued reference to FIG. 12, computing system 1200 may also include a storage device 1224. Examples of a storage device (e.g., storage device 1224) include, but are not limited to, a hard disk drive, a magnetic disk drive, an optical disc drive in combination with an optical medium, a solid-state memory device, and any combinations thereof. Storage device 1224 may be connected to bus 1212 by an appropriate interface (not shown). Example interfaces include, but are not limited to, small computer system interface, advanced technology attachment, serial advanced technology attachment, universal serial bus, IEEE 1394 (FIREWIRE), and any combinations thereof. In one example, storage device 1224 (or one or more components thereof) may be removably interfaced with computing system 1200 (e.g., via an external port connector (not shown)). Particularly, storage device 1224 and an associated machine-readable medium 1228 may provide nonvolatile and/or volatile storage of machine-readable instructions, data structures, program modules, and/or other data for computing system 1200. In one example, software 1220 may reside, completely or partially, within machine-readable medium 1228. In another example, software 1220 may reside, completely or partially, within processor 1204.

With continued reference to FIG. 12, computing system 1200 may also include an input device 1232. In one example, a user of computing system 1200 may enter commands and/or other information into computing system 1200 via input device 1232. Examples of input device 1232 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1232 may be interfaced to bus 1212 via any of a variety of interfaces (not shown) including, but not limited to, a serial interface, a parallel interface, a game port, a USB interface, a FIREWIRE interface, a direct interface to bus 1212, and any combinations thereof. Input device 1232 may include a touch screen interface that may be a part of or separate from display device 1236, discussed further below. Input device 1232 may be utilized as a user selection device for selecting one or more graphical representations in a graphical interface as described above.

With continued reference to FIG. 12, user may also input commands and/or other information to computing system 1200 via storage device 1224 (e.g., a removable disk drive, a flash drive, etc.) and/or network interface device 1240. A network interface device, such as network interface device 1240, may be utilized for connecting computing system 1200 to one or more of a variety of networks, such as network 1244, and one or more remote devices 1248 connected thereto. Examples of a network interface device include, but are not limited to, a network interface card (e.g., a mobile network interface card, a LAN card), a modem, and any combination thereof. Examples of a network include, but are not limited to, a wide-area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1244, may employ a wired and/or a wireless mode of communication. In general, any network topology may be used. Information (e.g., data, software 1220, etc.) may be communicated to and/or from computing system 1200 via network interface device 1240.

With continued reference to FIG. 12, computing system 1200 may further include a video display adapter 1252 for communicating a displayable image to a display device, such as display device 1236. Examples of a display device include, but are not limited to, a liquid crystal display (LCD), a cathode ray tube (CRT), a plasma display, a light emitting diode (LED) display, and any combinations thereof. Display adapter 1252 and display device 1236 may be utilized in combination with processor 1204 to provide graphical representations of aspects of the present disclosure. In addition to a display device, computing system 1200 may include one or more other peripheral output devices including, but not limited to, an audio speaker, a printer, and any combinations thereof. Such peripheral output devices may be connected to bus 1212 via a peripheral interface 1256. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

All combinations of the foregoing concepts and additional concepts discussed herewithin (provided such concepts are not mutually inconsistent) are contemplated as being part of the subject matter disclosed herein. The terminology explicitly employed herein that also may appear in any disclosure incorporated by reference should be accorded a meaning most consistent with the particular concepts disclosed herein.

The drawings are primarily for illustrative purposes and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

The entirety of this application (including the Cover Page, Title, Headings, Background, Summary of the Disclosure, Brief Description of the Drawings, Detailed Description, Embodiments, Abstract, Figures, Appendices, and otherwise) shows, by way of illustration, various embodiments in which the embodiments may be practiced. The advantages and features of the application are of a representative sample of embodiments only and are not exhaustive and/or exclusive. Rather, they are presented to assist in understanding and teach the embodiments and are not meant to be representative of all embodiments. As such, certain aspects of the disclosure have not been discussed herein. That alternate embodiments cannot have been presented for a specific portion of the innovations or that further undescribed alternate embodiments may be available for a portion is not to be considered to exclude such alternate embodiments from the scope of the disclosure. It will be appreciated that many of those undescribed embodiments incorporate the same principles of the innovations and others are equivalent. Thus, it is to be understood that other embodiments may be utilized and functional, logical, operational, organizational, structural and/or topological modifications may be made without departing from the scope and/or spirit of the disclosure. As such, all examples and/or embodiments are deemed to be non-limiting throughout this disclosure.

Also, no inference should be drawn regarding those embodiments discussed herein relative to those not discussed herein other than it is as such for purposes of reducing space and repetition. For example, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure.

The term "determining" encompasses a wide variety of actions and, therefore, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The phrase "based on" does not mean "based only on," unless expressly specified otherwise. In other words, the phrase "based on" describes both "based only on" and "based at least on".

The term "processor" should be interpreted broadly to encompass a general-purpose processor, a central processing unit (CPU), a microprocessor, a digital signal processor (DSP), a controller, a microcontroller, a state machine and so forth. Under some circumstances, a "processor" may refer to an application specific integrated circuit (ASIC), a programmable logic device (PLD), a field programmable gate array (FPGA), etc. The term "processor" may refer to a combination of processing devices, e.g., a combination of a DSP and a microprocessor, multiple microprocessors, one or more microprocessors in conjunction with a DSP core or any other such configuration.

The term "memory" should be interpreted broadly to encompass any electronic component capable of storing electronic information. The term memory may refer to various types of processor-readable media such as random-access memory (RAM), read-only memory (ROM), non-volatile random-access memory (NVRAM), programmable read-only memory (PROM), erasable programmable read-only memory (EPROM), electrically erasable PROM (EEPROM), flash memory, magnetic or optical data storage, registers, etc. Memory is said to be in electronic communication with a processor if the processor may read information from and/or write information to the memory. Memory that is integral to a processor is in electronic communication with the processor.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which may include, for example, the instructions and/or computer code discussed herein.

Some embodiments and/or methods described herein may be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) may be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

The indefinite articles "a" and "an," as used herein in the specification and in the embodiments, unless clearly indicated to the contrary, should be understood to mean "at least one".

The phrase "and/or", as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either", "one of", "only one of", or "exactly one of". "Consisting essentially of", when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. An apparatus for facilitating electrode placement, the apparatus comprising:
   a stimulation device, wherein the stimulation device comprises:
      an electrode lead having a plurality of electrodes, wherein each electrode of the plurality of electrodes is configured to transmit an electrical impulse towards a target location;
   a plurality of sensors, wherein each sensor of the plurality of sensors is configured to detect electrical activity data;
   a computing device communicatively connected to the stimulation device and the plurality of sensors, wherein the computing device comprises:
      a processor; and
      a memory communicatively connected to the processor, wherein the memory contains instructions configurating the processor to:
         implement a first stimulation protocol, wherein the first stimulation protocol comprises one or more stimulation parameters pertaining to at least an electrode of the plurality of electrodes;
         receive the electrical activity data from at least a sensor of the plurality of sensors in response to the stimulation protocol;
         optimize a quality of the electrical activity data;
         extract the optimized electrical activity data;
         analyze the optimized electrical activity data as a function of one or more predefined criteria, wherein analyzing the optimized electrical activity data comprises calculating a symmetrical activation measure; and
         generate, using a user interface, a visual representation as a function of the analyzed electrical activity data.

2. The apparatus of claim 1, wherein the processor is further configured to:
   assess a functional positioning of the stimulation device; and
   output the visual representation, wherein the visual representation comprises a recommended adjustment in the functional positioning as a function of the assessment.

3. The apparatus of claim 1, wherein the electrical activity data comprises one or more biosignals.

4. The apparatus of claim 3, wherein analyzing the electrical activity data comprises:
   calculating one or more metrics as a function of the optimized electrical activity data; and
   identifying the target location as a function of the one or more metrics.

5. The apparatus of claim 4, wherein the one or more metrics are selected from a group consisting of a laterality, an activation ratio, and an activation efficiency measure, and a symmetrical activation measure, as a function of the electrical activity data.

6. The apparatus of claim 4, wherein analyzing the electrical activity data comprises identifying at least a neural structure as a function of the electrical activity data.

7. The apparatus of claim 4, wherein:
   the target location comprises at least a location associated with one or more muscles, muscle groups, or myotomes; and
   analyzing the electrical activity data comprises ranking the target location as a function of the electrical activity data.

8. The apparatus of claim 1, wherein at least a stimulation parameter of the one or more stimulation parameters indicates how a first electrical impulse generated by a first electrode of the plurality of electrodes spatially relates to a second electrical impulse generated by a second electrode of the plurality of electrodes.

9. The apparatus of claim 1, wherein at least a stimulation parameter of the one or more stimulation parameters includes a current amplitude between 0.1 mA and 200 mA.

10. The apparatus of claim 9, wherein the processor is further configured to:
   receive additional electrical activity data from the at least a sensor of a plurality of sensors; and
   iteratively adjust a fit line as a function of the additional electrical activity data.

11. The apparatus of claim 1, wherein at least a stimulation parameter of the one or more stimulation parameters includes a frequency between 0.5 Hz and 1000 Hz.

12. The apparatus of claim 1, wherein at least a stimulation parameter of the one or more stimulation parameters includes a pulse width between 0.001 millisecond and 500 milliseconds.

13. The apparatus of claim 1, wherein analyzing the electrical activity data comprises approximating a functional midline with respect to a spinal cord.

14. The apparatus of claim 1, wherein the plurality of electrodes comprises at least an active-reference electrode pair.

15. A method for facilitating electrode placement, the method comprising:
implementing, by a processor, a first stimulation protocol, wherein:
the first stimulation protocol comprises one or more stimulation parameters pertaining to at least an electrode of a plurality of electrodes, wherein each electrode of the plurality of electrodes is configured to transmit an electrical impulse towards a target location;
receiving, by the processor, electrical activity data from at least a sensor of the plurality of sensors in response to the stimulation protocol;
optimizing, by the processor, a quality of the electrical activity data;
extracting, by the processor, the optimized electrical activity data;
analyzing, by the processor, the optimized electrical activity data as a function of one or more predefined criteria, wherein analyzing the optimized electrical activity data comprises calculating a symmetrical activation measure; and
generating, by the processor using a user interface, a visual representation as a function of the analyzed electrical activity data.

16. The method of claim 15, further comprising:
assessing, by the processor, a functional positioning of the at least an electrode; and
outputting, by the processor, the visual representation comprising a recommended adjustment in the functional positioning as a function of the assessment.

17. The method of claim 15, further comprising:
implementing, by the processor, at least a second stimulation protocol;
receiving, by the processor, additional electrical activity data in response to the at least a second stimulation protocol;
comparing, by the processor, the additional electrical activity data with the electrical activity data; and
outputting, by the processor, a determination in a functional positioning of the at least an electrode as a function of the comparison.

18. The method of claim 15, wherein the electrical activity data comprises one or more biosignals.

19. The method of claim 18, wherein analyzing the electrical activity data comprises:
calculating one or more metrics as a function of the optimized electrical activity data; and
identifying the target location as a function of the one or more metrics.

20. The method of claim 19, wherein the one or more metrics are selected from a group consisting of a laterality, an activation ratio, and an activation efficiency measure, as a function of the electrical activity data.

21. The method of claim 19, wherein analyzing the electrical activity data comprises identifying at least a neural structure as a function of the electrical activity data.

22. The method of claim 15, wherein at least a stimulation parameter of the one or more stimulation parameters indicates how a first electrical impulse generated by a first electrode of the plurality of electrodes spatially and temporally relates to a second electrical impulse generated by a second electrode of the plurality of electrodes.

23. The method of claim 15, wherein at least a stimulation parameter of the one or more stimulation parameters includes a current amplitude between 0.1 mA and 200 mA.

24. The method of claim 15, wherein at least a stimulation parameter of the one or more stimulation parameters includes a frequency between 0.5 Hz and 1000 Hz.

25. The method of claim 15, wherein at least a stimulation parameter of the one or more stimulation parameters includes a pulse width between 0 millisecond and 500 milliseconds.

26. The method of claim 15, wherein analyzing the electrical activity data comprises approximating a functional midline with respect to a spinal cord using a fit line.

27. The method of claim 26, further comprising:
receiving, by the processor, additional electrical activity data from the at least a sensor of a plurality of sensors; and
iteratively adjusting, using the processor, the fit line as a function of the additional electrical activity data.

28. The method of claim 15, wherein:
the target location comprises at least a location associated with one or more muscles, muscle groups, or myotomes; and
analyzing the electrical activity data comprises ranking the target location as a function of the electrical activity data.

* * * * *